(12) United States Patent
Schiffer-Mannioui

(10) Patent No.: US 10,544,201 B2
(45) Date of Patent: Jan. 28, 2020

(54) ROR1 SPECIFIC MULTI-CHAIN CHIMERIC ANTIGEN RECEPTOR

(71) Applicant: CELLECTIS, Paris (FR)

(72) Inventor: Cècile Schiffer-Mannioui, Villiers-sur-Marne (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/329,530

(22) PCT Filed: Jul. 29, 2015

(86) PCT No.: PCT/EP2015/067441
§ 371 (c)(1),
(2) Date: Jan. 26, 2017

(87) PCT Pub. No.: WO2016/016343
PCT Pub. Date: Feb. 4, 2016

(65) Prior Publication Data
US 2017/0226183 A1 Aug. 10, 2017

(30) Foreign Application Priority Data

Jul. 31, 2014 (DK) .................................. 2014 70469

(51) Int. Cl.
*C07K 14/705* (2006.01)
*C07K 14/735* (2006.01)
*C07K 16/28* (2006.01)

(52) U.S. Cl.
CPC .... *C07K 14/70535* (2013.01); *C07K 16/2803* (2013.01); *C07K 2317/56* (2013.01); *C07K 2317/565* (2013.01); *C07K 2317/622* (2013.01); *C07K 2319/00* (2013.01); *C07K 2319/03* (2013.01); *C07K 2319/33* (2013.01); *C07K 2319/70* (2013.01)

(58) Field of Classification Search
CPC ................................................ C07K 14/70535
See application file for complete search history.

(56) References Cited

U.S. PATENT DOCUMENTS

| | | | |
|---|---|---|---|
| 4,683,195 A | 7/1987 | Mullis et al. | |
| 5,037,743 A | 8/1991 | Welch et al. | |
| 5,143,830 A | 9/1992 | Holland et al. | |
| 5,225,539 A | 7/1993 | Winter | |
| 5,530,101 A | 6/1996 | Queen et al. | |
| 5,585,089 A | 12/1996 | Queen et al. | |
| 5,766,886 A | 6/1998 | Studnicka et al. | |
| 5,858,358 A | 1/1999 | June et al. | |
| 5,883,223 A | 3/1999 | Gray | |
| 6,010,613 A | 1/2000 | Walters et al. | |
| 6,352,694 B1 | 3/2002 | June et al. | |
| 6,407,213 B1 | 6/2002 | Carter et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 2003/0105000 A1* | 6/2003 | Pero ........................ | A61K 38/06 514/19.3 |
| 2005/0042664 A1 | 2/2005 | Wu et al. | |
| 2005/0048617 A1 | 3/2005 | Wu et al. | |
| 2006/0121005 A1 | 6/2006 | Berenson et al. | |

(Continued)

FOREIGN PATENT DOCUMENTS

| | | |
|---|---|---|
| EP | 0239400 | 8/1994 |
| EP | 0592106 | 11/2004 |

(Continued)

OTHER PUBLICATIONS

Hudecek et al: "Receptor Affinity and Extracellular Domain Modifications Affect Tumor Recognition by ROR1-Specific Chimeric Antigen Receptor T Cells", Clinical Cancer Research, vol. 19, No. 12, Apr. 25, 2013 (Apr. 25, 2013), pp. 3153-3164 (Year: 2013).*
Almagro & Fransson, Frontiers in Bioscience 2008; 13: 1619-33 (Year: 2008).*
Banihashemi et al. (Iranian J. Basic Medical Sciences 2018 21:455-464) (Year: 2018).*
Rudikoff et al. (PNAS USA, 1982, 79: 1979-1983) (Year: 1982).*
Coleman et al. (Research in Immunology, 1994; 145(1): 33-36 (Year: 1994).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Arimondo et al., "Exploring the cellular activity of camptothecin-triple-helix-fonning oligonucleotide conjugates," Mol. Cell Biol., 26(1):324-33, Jan. 2006.

(Continued)

Primary Examiner — Scott Long
(74) Attorney, Agent, or Firm — Fish & Richardson P.C.

(57) ABSTRACT

The present invention relates to a new generation of chimeric antigen receptors (CAR) referred to as multi-chain CARs, which are made specific to the antigen ROR1. Such CARs aim to redirect immune cell specificity and reactivity toward malignant cells expressing the tumor antigen ROR1. The alpha, beta and gamma polypeptides composing these CARs are designed to assemble in juxtamembrane position, which forms flexible architecture closer to natural receptors, that confers optimal signal transduction. The invention encompasses the polynucleotides, vectors encoding said multi-chain CAR and the isolated cells expressing them at their surface, in particularly for their use in immunotherapy. The invention opens the way to efficient adoptive immunotherapy strategies for treating cancer, especially chronic lymphocytic leukemia or solid tumors.

20 Claims, 9 Drawing Sheets

Specification includes a Sequence Listing.

(56) References Cited

U.S. PATENT DOCUMENTS

| | | |
|---|---|---|
| 2007/0231333 A1 | 10/2007 | Boghaert et al. |
| 2013/0280221 A1 | 10/2013 | Schonfeld et al. |
| 2013/0287748 A1 | 10/2013 | June et al. |
| 2014/0234348 A1 | 8/2014 | Scholler et al. |
| 2017/0283497 A1 | 10/2017 | Schiffer-Mannioui |

FOREIGN PATENT DOCUMENTS

| | | | |
|---|---|---|---|
| EP | 519596 | 2/2005 | |
| JP | 2014/510108 | 4/2014 | |
| WO | WO 91/09967 | 7/1991 | |
| WO | WO 93/17105 | 9/1993 | |
| WO | WO 2004/083379 | 9/2004 | |
| WO | WO 2012/012695 | 1/2012 | |
| WO | WO 2012/097313 | 7/2012 | |
| WO | WO 2012/138927 | 10/2012 | |
| WO | WO 2013/033626 | 3/2013 | |
| WO | WO2013/063419 | * 5/2013 | ............ A61K 48/00 |
| WO | WO 2013/123061 | 8/2013 | |
| WO | WO 2013/123061 A1 | 8/2013 | |
| WO | WO 2013/176915 | 11/2013 | |
| WO | WO 2014/031174 | 2/2014 | |
| WO | WO 2014/031687 | 2/2014 | |
| WO | WO 2014/039523 | 3/2014 | |
| WO | WO 2014/039523 A1 | 3/2014 | |

OTHER PUBLICATIONS

Atkins et al., "A case for "StopGo": reprogramming translation to augment codon meaning of GGN by promoting unconventional termination (Stop) after addition of glycine and then allowing continued translation (Go)," Rna., 13(6):803-10, Jun. 2007.

Baskar et al., "Unique cell surface expression of receptor tyrosine kinase ROR1 in human B-cell chronic lymphocytic leukemia," Clin. Cancer Res. Off. J. Am. Assoc. Cancer Res., 14(2):396-404, Jan. 2008.

Bicocca et al., "Crosstalk between ROR1 and the Pre-B cell receptor promotes survival of t (1; 19) acute lymphoblastic leukemia," Cancer Cell, 22(5):656-667, Nov. 2012.

Bierer et al., "Cyclosporin A and FK506: molecular mechanisms of immunosuppression and probes for transplantation biology," Curr. Opin. Immunol., 5(5):763-73, Oct. 1993.

Birkle et al., "Role of tumor-associated gangliosides in cancer progression," Biochimie., 85(3-4):455-463, Mar.-Apr. 2003.

Boch et al., "Breaking the code of DNA binding specificity of TAL-type III effectors," Science, 326(5959):1509-12, Dec. 2009.

Carsberg et al., "Metastasis-associated 5T4 oncofoetal antigen is concentrated at microvillus projections of the plasma membrane," J. Cell Sci., 108(8):2905-16, Aug. 1995.

Castro et al., "5T4 oncofetal antigen is expressed in high risk of relapse childhood pre-B acute lymphoblastic leukemia and is associated with a more invasive and chemotactic phenotype," Leukemia., 26(7):1487-98, Jul. 2012.

Choudhury et al., "Silencing of ROR1 and FMOD with siRNA results in apoptosis of CLL cells," Br. J. Haematol., 151(4):327-335, Nov. 2010.

Choulika et al., "Induction of homologous recombination in mammalian chromosomes by using the I-SceI system of *Saccharomyces cerevisiae*," Mol. Cell. Biol., 15(4):1968-73, Apr. 1995.

Christian et al., "Targeting DNA double-strand breaks with TAL effector nucleases," Genetics, 186(2):757-61, Oct. 2010.

Cong et al., "Multiplex genome engineering using CRISPR/Cas systems," Science, 339(6121):819-23, Feb. 2013.

Cooper, "L. Innovative T Cell-Targeted Therapy for Ovarian Cancer," Annual Report 2012 prepared for US Army medical research and Medical Command.

Cros et al., "Problems related to resistance to cytarabine in acute myeloid leukemia," Leukemia & Lymphoma, 45(6):1123-1132, Jun. 2004.

Daneshmanesh et al., "Ror1, a cell surface receptor tyrosine kinase is expressed in chronic lymphocytic leukemia and may serve as a putative target for therapy," Int. J. Cancer, 123(5):1190-5, Sep. 2008.

Daniotti et al., "Cloning, characterization and developmental expression of alpha2,8 sialyltransferase (GD3 synthase, ST8Sia I) gene in chick brain and retina," Int. J. Dev. Neurosci., 15(6):767-776, Oct. 1997.

Dave et al., "Restricted cell surface expression of receptor tyrosine kinase ROR1 in pediatric B-lineage acute lymphoblastic leukemia suggests targetability with therapeutic monoclonal antibodies," PLoS One., 7(12):e52655, Dec. 2012.

Deltcheva et al., "CRISPR RNA maturation by trans-encoded small RNA and host factor RNase III," Nature, 471(7340):602-7, Mar. 2011.

Donelly et al., "The cleavage activities of aphthovirus and cardiovirus 2A proteins," J. Gen. Virol., 78:13-21, Jan. 1997.

Donnelly and Elliott, "Nuclear localization and shuttling of herpes simplex virus tegument protein VP13/14," J. Virol., 75(6):2566-74, Mar. 2001.

Donnelly et al., "Analysis of the aphthovirus 2A/2B polyprotein 'cleavage' mechanism indicates not a proteolytic reaction, but a novel translational effect: a putative ribosomal 'skip'," J. Gen. Virol., 82:1013-1025, May 2001.

Doronina et al., "Site-specific release of nascent chains from ribosomes at a sense codon," Mol. Cell Biol., 28(13):4227-39, Jul. 2008.

Dotti et al., "Redirecting T-cell specificity by introducing a tumor-specific chimeric antigen receptor," Blood., 116(7):1035-1044, Aug. 2010.

Eisenschmidt et al., "Developing a programmed restriction endonuclease for highly specific DNA cleavage." Nucleic. Acids. Res., 33(22):7039-47, Jan. 2005.

Fukuda et al., "Antisera induced by infusions of autologous Ad-CD154-leukemia B cells identify ROR1 as an oncofetal antigen and receptor for Wnt5a," Proc. Natl. Acad. Sci. U.S.A., 105(8):3047-3052, Feb. 2008.

Gardin et al., "Postremission treatment of elderly patients with acute myeloid leukemia in first complete remission after intensive induction chemotherapy: results of the multicenter randomized Acute Leukemia French Association (ALFA) 9803 trial," Blood., 109(12):5129-5135, Jun. 2007.

Garneau et al., "The CRISPR/Cas bacterial immune system cleaves bacteriophage and plasmid DNA," Nature, 468(7320):67-71, Nov. 2010.

Gasiunas et al., "Cas9-crRNA ribonucleoprotein complex mediates specific DNA cleavage for adaptive immunity in bacteria," Proc. Natl. Acad. Sci. U.S.A., 109(39):E2579-86, Sep. 2012.

GenBank Association No. AAA53133.1, "4-1BB [*Homo sapiens*]," Nov. 27, 1994, 2 pages.

GenBank Association No. NP001139345.1, "T-cell surface glycoprotein CD8 alpha chain isoform 1 precursor [*Homo sapiens*]," Mar. 15, 2015, 3 pages.

GenBank Association No. NP001992.1, "high affinity immunoglobulin epsilon receptor subunit alpha precursor [*Homo sapiens*]," Jan. 15, 2016, 3 pages.

GenBank Association No. NP006130.1, "T-cell-specific surface glycoprotein CD28 isoform 1 precursor [*Homo sapiens*]," Mar. 15, 2015, 3 pages.

Gentile et al., "Ror1 is a pseudokinase that is crucial for Met-driven tumorigenesis," Cancer Res., 71(8):3132-3141, Apr. 2011.

Gravotta et al., "In vivo and in vitro expression of gangliosides in chick retina Müeller cells," J. Neurochem., 52(3):768-776, Mar. 1989.

Guest et al., "The role of extracellular spacer regions in the optimal design of chimeric immune receptors: evaluation of four different scFvs and antigens," J. Immunother., 28(3):203-211, May 2005.

Haraguchi et al., "Isolation of GD3 synthase gene by expression cloning of GM3 alpha-2,8-sialyltransferase cDNA using anti-GD2 monoclonal antibody," Proc. Natl. Acad. Sco. U.S.A., 91(22):10455-10459, Oct. 1994.

(56) References Cited

OTHER PUBLICATIONS

Henderson et al., "Comparison of the effects of FK-506, cyclosporin A and rapamycin on IL-2 production," Immunology, 73(3):316-21, Jul. 1991.
Hole and Stern., "A 72 kD trophoblast glycoprotein defined by a monoclonal antibody," Br. J. Cancer, 57(3):239-246, Mar. 1988.
Jena et al., "Redirecting T-cell specificity by introducing a tumor-specific chimeric antigen receptor," Blood, 116(7):1035-44, Aug. 2010.
Jinek et al., "A programmable dual-RNA-guided DNA endonuclease in adaptive bacterial immunity," Science, 337(6096):816-21, Jun. 2012.
June et al., "T cells with chimeric antigen receptors have potent antitumor effects and can establish memory in patients with advanced leukemia," Sci. Transl. Med., 3(95):95ra73, Aug. 2011.
Kalish and Glazer, "Targeted genome modification via triple helix formation," Ann. N.Y. Acad. Sci., 1058(1):151-61, Nov. 2005.
Klein et al., "Gene expression profiling of B cell chronic lymphocytic leukemia reveals a homogeneous phenotype related to memory B cells," J. Exp. Med., 194:1625-1638, Dec. 2001.
Li et al., "TAL nucleases (TALNs): hybrid proteins composed of TAL effectors and FokI DNA-cleavage domain," Nucleic. Acids. Res., 39(1):359-72, Jan. 2011.
Liu et al., "Calcineurin is a common target of cyclophilin-cyclosporin A and FKBP-FK506 complexes," Cell, 66(4):807-815, Aug. 1991.
Liu et al., "Inhibition of T cell signaling by immunophilin-ligand complexes correlates with loss of calcineurin phosphatase activity," Biochemistry., 31(16):3896-901, Apr. 1992.
Lo et al., "Anti-GD3 chimeric sFv-CD28/T-cell receptor zeta designer T cells for treatment of metastatic melanoma and other neuroectodermal tumors," Clin. Cancer Res., 16(10):2769-2780, May 2010.
Mali et al., "RNA-guided human genome engineering via Cas9," Science, 339(6121):823-6, Feb. 2013.
Mannioui et al., "Treatment of B cells malignancies with anti-CD19 CAR+, TCR−, CD52− allogeneic T cells," J ImmunoTherapy Canc., BioMed Central Ltd, London UK, 1(Suppl 1):P34, Nov. 7, 2013.
Matsuda et al., "Expression of the receptor tyrosine kinase genes, Ror1 and Ror2, during mouse development," Mech. Dev., 105(1-2):153-156, Jul. 2001.
Moscou and Bogdanove, "A simple cipher governs DNA recognition by TAL effectors," Science, 326(5959):1501, Dec. 2009.
Nakayama et al., "Expression cloning of a human GT3 synthase. GD3 and GT3 are synthesized by a single enzyme," J. Biol. Chem., 271(7):3684-91, Feb. 1996.
Padlan, "A possible procedure for reducing the immunogenicity of antibody variable domains while preserving their ligand-binding properties," Mol. Immunol., 28(4-5):489-498, Apr.-May 1991.
Paques and Duchateau, "Meganucleases and DNA double-strand break-induced recombination: perspectives for gene therapy," Curr. Gene Ther., 7(1):49-66, Feb. 2007.
Park et al., "Treating cancer with genetically engineered T cells," Trends Biotechnol., 29(11):550-7, Nov. 2011.
Peipp et al., "Efficient eukaryotic expression of fluorescent scFv fusion proteins directed against CD antigens for FACS applications," J. Immunol. Methods, 285(2):265-80, Feb. 2004.
Perrin et al., "Asymmetrical recognition and activity of the I-SceI endonuclease on its site and on intron-exon junctions," Embo. J., 12(7):2939-47, Jul. 1993.
Pingoud and Silva, "Precision genome surgery," Nat. Biotechnol., 25(7):743-4, Jul. 2007.
Poirot et al., "521 multiplex genome editing of TCR a/CD52 Genes as a platform for "Off the Shelf" Adoptive T-cell immunotherapies," 17th Annual Meeting of the American-Sciety-of-Gene-and-Cell-Therapy (ASGCT), 22(Suppl. 1):S201-S202, May 1, 2014, Washington DC., USA.
Poirot et al., "T-Cell engineering for "off-the-shelf" Adoptive Immunotherapy," Blood., 122(21):1661, Nov. 15, 2013.
Porter et al., "Chimeric antigen receptor-modified T cells in chronic lymphoid leukemia," N. Engl. J. Med., 365(8):725-733, Aug. 2011.
Porteus and Carroll, "Gene targeting using zinc finger nucleases," Nat. Biotechnol., 23(8):967-73, Aug. 2005.
Reaman et al., "Anti-GD3 monoclonal antibody analysis of childhood T-cell acute lymphoblastic leukemia: detection of a target antigen for antibody-mediated cytolysis," Cancer Res., 50(1):202-205, Jan. 1990.
Reddy et al., "Localization of the human Ror1 gene (NTRKR1) to chromosome 1p31-p32 by fluorescence in situ hybridization and somatic cell hybrid analysis," Genomics, 41(2):238-5, Apr. 1997.
Rosenwald et al., "Relation of gene expression phenotype to immunoglobulin mutation genotype in B cell chronic lymphocytic leukemia," J. Exp. Med., 194(11):1639-1647, Dec. 2001.
Rouet et al., "Introduction of double-strand breaks into the genome of mouse cells by expression of a rare-cutting endonuclease," Mol. Cell Biol., 14(12):8096-106, Dec. 1994.
Sorek et al., "CRISPR-mediated adaptive immune systems in bacteria and archaea," Annu. Rev. Biochem., Jun. 2013.
Starzynska et al., "5T4 oncofetal antigen in gastric carcinoma and its clinical significance," Eur. J. Gatrerol Heptol., 10(6):479-84, Jun. 1998.
Stoddard, "Homing endonuclease structure and function," Q. Rev. Biophys., 38(1):49-95, Feb. 2005.
Studincka et al., "Human-engineered monoclonal antibodies retain full specific binding activity by preserving non-CDR complementarity-modulating residues," Protein Eng., 7(6):805-814, Jun. 1994.
Yamaguchi et al., "NKX2-1/TITF1/TTF-1-Induced ROR1 is required to sustain EGFR survival signaling in lung adenocarcinoma," Cancer Cell, 21(3):348-361, Mar. 2012.
Yun et al., "Targeting of T lymphocytes to melanoma cells through chimeric anti-GD3 immunoglobulin T-cell receptors," Neoplasia., 2(5):449-459, Sep.-Oct. 2000.
Zhang et al., "ROR1 is expressed in human breast cancer and associated with enhanced tumor-cell growth," PLoS One, 7(3):e31127, Mar. 2012.
Zhang et al., "The onco-embryonic antigen ROR1 is expressed by a variety of human cancers," Am. J. Pathol., 181(6):1903-1910, Dec. 2012.
Darcy et al., "Redirecting Mouse CTL Against Colon Carcinoma: Superior Signaling Efficacy of Single-Chain Variable Domain Chimeras Containing TCR- vs FceRI-y," The Journal of Immunology, downloaded from http://www.jimmunol.org/, 2001, pp. 182-187.
Hudecek et al., "Receptor affinity and extracellular domain modifications affect tumor recognition by ROR1-specific chimeric antigen Receptor T-cells," Clin. Cancer Res., Jun. 2013, vol. 19(2), pp. 3153-3164.
International Search Report and Written Opinion issued in International Patent Application No. PCT/EP2015/067441 dated Nov. 10, 2015 (9 pages).
Mariuzza et al., "The structural basis of antigen-antibody recognition," Annu. Rev. Biophys. Biophys. Chem., 16(1):139-159, Jun. 1987.

* cited by examiner

Native FcεRI

Structure of the polycistronic mcCAR construct

SEQUENCE LISTING

```
<160> NUMBER OF SEQ ID NOS: 88

<210> SEQ ID NO 1
<211> LENGTH: 25
<212> TYPE: PRT
<213> ORGANISM: artificial sequence
<220> FEATURE:
<223> OTHER INFORMATION: Fc&RI-SP signal peptide

<400> SEQUENCE: 1

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 2
<211> LENGTH: 45
<212> TYPE: PRT
<213> ORGANISM: artificial sequence
<220> FEATURE:
<223> OTHER INFORMATION: CD8a hinge

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 3
<211> LENGTH: 15
<212> TYPE: PRT
<213> ORGANISM: homo sapiens
<220> FEATURE:
```

<223> OTHER INFORMATION: G4SX3Linker

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 52
<212> TYPE: PRT
<213> ORGANISM: homo sapiens
<220> FEATURE:
<223> OTHER INFORMATION: FcεRI α-TM-IC

<400> SEQUENCE: 4

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
                20                  25                  30

Arg Thr Arg Lys Gly Phe Arg Leu Leu Asn Pro His Pro Lys Pro Asn
            35                  40                  45

Pro Lys Asn Asn
    50

<210> SEQ ID NO 5
<211> LENGTH: 215
<212> TYPE: PRT
<213> ORGANISM: homo sapiens
<220> FEATURE:
<223> OTHER INFORMATION: FceR1b-DITAM

<400> SEQUENCE: 5

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
                20                  25                  30

Val Ser Ser Gly Arg Leu Leu Lys Ser Ala Ser Ser Pro Pro Leu His
            35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
                100                 105                 110

Met Leu Ser Ile Ile Ser Glu Arg Arg Asn Ala Thr Tyr Leu Val Arg
            115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
                180                 185                 190

Leu Gly Ser Ala Val Ser Leu Thr Ile Cys Gly Ala Gly Glu Glu Leu
            195                 200                 205

Lys Gly Asn Lys Val Pro Glu

<210> SEQ ID NO 6
<211> LENGTH: 42
<212> TYPE: PRT
<213> ORGANISM: homo sapiens
<220> FEATURE:
<223> OTHER INFORMATION: 41BB-IC

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 7
<211> LENGTH: 18
<212> TYPE: PRT
<213> ORGANISM: homo sapiens
<220> FEATURE:
<223> OTHER INFORMATION: FcεRI γ-SP

<400> SEQUENCE: 7

Met Ile Pro Ala Val Val Leu Leu Leu Leu Leu Leu Val Glu Gln Ala
1               5                   10                  15

Ala Ala

<210> SEQ ID NO 8
<211> LENGTH: 43
<212> TYPE: PRT
<213> ORGANISM: homo sapiens
<220> FEATURE:
<223> OTHER INFORMATION: FcεRI γ - DITAM

<400> SEQUENCE: 8

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser
        35                  40

<210> SEQ ID NO 9
<211> LENGTH: 112
<212> TYPE: PRT
<213> ORGANISM: homo sapiens
<220> FEATURE:
<223> OTHER INFORMATION: CD3ζ-IC

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 10
<211> LENGTH: 22
<212> TYPE: PRT
<213> ORGANISM: artificial sequence
<220> FEATURE:
<223> OTHER INFORMATION: GSG-P2A

<400> SEQUENCE: 10

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 11
<211> LENGTH: 21
<212> TYPE: PRT
<213> ORGANISM: artificial sequence
<220> FEATURE:
<223> OTHER INFORMATION: GSG-T2A

<400> SEQUENCE: 11

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 12
<211> LENGTH: 118
<212> TYPE: PRT
<213> ORGANISM: artificial sequence
<220> FEATURE:
<223> OTHER INFORMATION: 2A2 heavy chain variable region

<400> SEQUENCE: 12

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
            85                  90                  95

Thr Gly Tyr Tyr Asp Tyr Asp Ser Phe Thr Tyr Trp Gly Gln Gly Thr
            100                 105                 110

Leu Val Thr Val Ser Ala
        115

<210> SEQ ID NO 13
<211> LENGTH: 8
<212> TYPE: PRT
<213> ORGANISM: artificial sequence
<220> FEATURE:

<223> OTHER INFORMATION: CDR1 of 2A2 VH chain

<400> SEQUENCE: 13

Gly Tyr Thr Phe Ser Asp Tyr Glu
1               5

<210> SEQ ID NO 14
<211> LENGTH: 8
<212> TYPE: PRT
<213> ORGANISM: artificial sequence
<220> FEATURE:
<223> OTHER INFORMATION: CDR2 of 2A2 VH chain

<400> SEQUENCE: 14

Ile Asp Pro Glu Thr Gly Gly Thr
1               5

<210> SEQ ID NO 15
<211> LENGTH: 11
<212> TYPE: PRT
<213> ORGANISM: artificial sequence
<220> FEATURE:
<223> OTHER INFORMATION: CDR3 of 2A2 VH chain

<400> SEQUENCE: 15

Thr Gly Tyr Tyr Asp Tyr Asp Ser Phe Thr Tyr
1               5                   10

<210> SEQ ID NO 16
<211> LENGTH: 107
<212> TYPE: PRT
<213> ORGANISM: artificial sequence
<220> FEATURE:
<223> OTHER INFORMATION: 2A2 light chain variable region

<400> SEQUENCE: 16

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
            100                 105

<210> SEQ ID NO 17
<211> LENGTH: 6
<212> TYPE: PRT
<213> ORGANISM: artificial sequence
<220> FEATURE:
<223> OTHER INFORMATION: CDR1 of 2A2 VL chain

<400> SEQUENCE: 17

Gln Asn Val Asp Ala Ala
1               5

<210> SEQ ID NO 18

```
<211> LENGTH: 3
<212> TYPE: PRT
<213> ORGANISM: artificial sequence
<220> FEATURE:
<223> OTHER INFORMATION: CDR2 of 2A2 VL chain

<400> SEQUENCE: 18

Ser Ala Ser
1

<210> SEQ ID NO 19
<211> LENGTH: 9
<212> TYPE: PRT
<213> ORGANISM: artificial sequence
<220> FEATURE:
<223> OTHER INFORMATION: CDR3 of 2A2 VL chain

<400> SEQUENCE: 19

Gln Gln Tyr Asp Ile Tyr Pro Tyr Thr
1               5

<210> SEQ ID NO 20
<211> LENGTH: 119
<212> TYPE: PRT
<213> ORGANISM: artificial sequence
<220> FEATURE:
<223> OTHER INFORMATION: 4A5 heavy chain variable region

<400> SEQUENCE: 20

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115

<210> SEQ ID NO 21
<211> LENGTH: 8
<212> TYPE: PRT
<213> ORGANISM: artificial sequence
<220> FEATURE:
<223> OTHER INFORMATION: CDR1 of 4A5 VH chain

<400> SEQUENCE: 21

Gly Phe Thr Phe Ser Ser Tyr Ala
1               5

<210> SEQ ID NO 22
<211> LENGTH: 7
<212> TYPE: PRT
<213> ORGANISM: artificial sequence
<220> FEATURE:
<223> OTHER INFORMATION: CDR2 of  4A5 VH chain
```

```
<400> SEQUENCE: 22

Ile Ser Arg Gly Gly Thr Thr
1               5

<210> SEQ ID NO 23
<211> LENGTH: 13
<212> TYPE: PRT
<213> ORGANISM: artificial sequence
<220> FEATURE:
<223> OTHER INFORMATION: CDR3 of 4A5 VH chain

<400> SEQUENCE: 23

Gly Arg Tyr Asp Tyr Asp Gly Tyr Tyr Ala Met Asp Tyr
1               5                   10

<210> SEQ ID NO 24
<211> LENGTH: 107
<212> TYPE: PRT
<213> ORGANISM: artificial sequence
<220> FEATURE:
<223> OTHER INFORMATION: 4A5 light chain variable region

<400> SEQUENCE: 24

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105

<210> SEQ ID NO 25
<211> LENGTH: 6
<212> TYPE: PRT
<213> ORGANISM: artificial sequence
<220> FEATURE:
<223> OTHER INFORMATION: CDR1 of 4A5 VL chain

<400> SEQUENCE: 25

Pro Asp Ile Asn Ser Tyr
1               5

<210> SEQ ID NO 26
<211> LENGTH: 3
<212> TYPE: PRT
<213> ORGANISM: artificial sequence
<220> FEATURE:
<223> OTHER INFORMATION: CDR2 of 4A5 VL chain

<400> SEQUENCE: 26

Arg Ala Asn
1

<210> SEQ ID NO 27
<211> LENGTH: 9
<212> TYPE: PRT
```

<213> ORGANISM: artificial sequence
<220> FEATURE:
<223> OTHER INFORMATION: CDR3 of 4A5 VL chain

<400> SEQUENCE: 27

Leu Gln Tyr Asp Glu Phe Pro Tyr Thr
1               5

<210> SEQ ID NO 28
<211> LENGTH: 117
<212> TYPE: PRT
<213> ORGANISM: artificial sequence
<220> FEATURE:
<223> OTHER INFORMATION: D10 heavy chain variable region

<400> SEQUENCE: 28

Gln Val Gln Leu Lys Glu Ser Gly Pro Gly Leu Val Ala Pro Ser Gln
1               5                   10                  15

Thr Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Phe Thr Asn Tyr Asn Ser Ala Leu Lys
    50                  55                  60

Ser Arg Leu Ser Ile Ser Lys Asp Asn Ser Lys Ser Gln Val Leu Leu
65                  70                  75                  80

Lys Met Thr Ser Leu Gln Thr Asp Asp Thr Ala Met Tyr Tyr Cys Ala
                85                  90                  95

Arg Arg Gly Ser Ser Tyr Ser Met Asp Tyr Trp Gly Gln Gly Thr Ser
            100                 105                 110

Val Thr Val Ser Ser
        115

<210> SEQ ID NO 29
<211> LENGTH: 8
<212> TYPE: PRT
<213> ORGANISM: artificial sequence
<220> FEATURE:
<223> OTHER INFORMATION: CDR1 of D10 VH chain

<400> SEQUENCE: 29

Gly Phe Ser Leu Thr Ser Tyr Gly
1               5

<210> SEQ ID NO 30
<211> LENGTH: 7
<212> TYPE: PRT
<213> ORGANISM: artificial sequence
<220> FEATURE:
<223> OTHER INFORMATION: CDR2 of D10 VH chain

<400> SEQUENCE: 30

Ile Trp Ala Gly Gly Phe Thr
1               5

<210> SEQ ID NO 31
<211> LENGTH: 11
<212> TYPE: PRT
<213> ORGANISM: artificial sequence
<220> FEATURE:
<223> OTHER INFORMATION: CDR3 of D10 VH chain

<400> SEQUENCE: 31

```
Ala Arg Arg Gly Ser Ser Tyr Ser Met Asp Tyr
1               5                   10
```

<210> SEQ ID NO 32
<211> LENGTH: 106
<212> TYPE: PRT
<213> ORGANISM: artificial sequence
<220> FEATURE:
<223> OTHER INFORMATION: D10 light chain variable region

<400> SEQUENCE: 32

```
Glu Ile Val Leu Ser Gln Ser Pro Ala Ile Thr Ala Ala Ser Leu Gly
1               5                   10                  15

Gln Lys Val Thr Ile Thr Cys Ser Ala Ser Ser Asn Val Ser Tyr Ile
            20                  25                  30

His Trp Tyr Gln Gln Arg Ser Gly Thr Ser Pro Arg Pro Trp Ile Tyr
        35                  40                  45

Glu Ile Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
                85                  90                  95

Phe Gly Ser Gly Thr Lys Leu Glu Ile Gln
            100                 105
```

<210> SEQ ID NO 33
<211> LENGTH: 5
<212> TYPE: PRT
<213> ORGANISM: artificial sequence
<220> FEATURE:
<223> OTHER INFORMATION: CDR1 of D10 VL chain

<400> SEQUENCE: 33

```
Ser Asn Val Ser Tyr
1               5
```

<210> SEQ ID NO 34
<211> LENGTH: 3
<212> TYPE: PRT
<213> ORGANISM: artificial sequence
<220> FEATURE:
<223> OTHER INFORMATION: CDR2 of D10 VL chain

<400> SEQUENCE: 34

```
Glu Ile Ser
1
```

<210> SEQ ID NO 35
<211> LENGTH: 9
<212> TYPE: PRT
<213> ORGANISM: artificial sequence
<220> FEATURE:
<223> OTHER INFORMATION: CDR3 of D10 VL chain

<400> SEQUENCE: 35

```
Gln Gln Trp Asn Tyr Pro Leu Ile Thr
1               5
```

<210> SEQ ID NO 36
<211> LENGTH: 119
<212> TYPE: PRT
<213> ORGANISM: artificial sequence
<220> FEATURE:

<223> OTHER INFORMATION: G6 heavy chain variable region

<400> SEQUENCE: 36

Glu Val Gln Leu Gln Gln Ser Gly Pro Glu Leu Glu Lys Pro Gly Ala
1               5                   10                  15

Ser Val Lys Ile Ser Cys Lys Ala Ser Gly Phe Ala Phe Thr Gly Tyr
            20                  25                  30

Asn Met Asn Trp Val Lys Gln Thr Asn Gly Lys Ser Leu Glu Trp Ile
        35                  40                  45

Gly Ser Ile Asp Pro Tyr Tyr Gly Gly Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Lys Ser Leu Thr Ser Asp Asp Ser Ala Val Tyr Tyr Cys
                85                  90                  95

Ala Arg Ser Pro Gly Gly Asp Tyr Ala Met Asp Tyr Trp Gly Gln Gly
            100                 105                 110

Thr Ser Val Thr Val Ser Ser
        115

<210> SEQ ID NO 37
<211> LENGTH: 8
<212> TYPE: PRT
<213> ORGANISM: artificial sequence
<220> FEATURE:
<223> OTHER INFORMATION: CDR1 of G6 VH chain

<400> SEQUENCE: 37

Gly Phe Ala Phe Thr Gly Tyr Asn
1               5

<210> SEQ ID NO 38
<211> LENGTH: 8
<212> TYPE: PRT
<213> ORGANISM: artificial sequence
<220> FEATURE:
<223> OTHER INFORMATION: CDR2 of G6 VH chain

<400> SEQUENCE: 38

Ile Asp Pro Tyr Tyr Gly Gly Ser
1               5

<210> SEQ ID NO 39
<211> LENGTH: 12
<212> TYPE: PRT
<213> ORGANISM: artificial sequence
<220> FEATURE:
<223> OTHER INFORMATION: CDR3 of G6 VH chain

<400> SEQUENCE: 39

Ala Arg Ser Pro Gly Gly Asp Tyr Ala Met Asp Tyr
1               5                   10

<210> SEQ ID NO 40
<211> LENGTH: 107
<212> TYPE: PRT
<213> ORGANISM: artificial sequence
<220> FEATURE:
<223> OTHER INFORMATION: G6 light chain variable region

<400> SEQUENCE: 40

Asp Ile Lys Met Thr Gln Ser Pro Ser Ser Met Tyr Ala Ser Val Gly
1               5                   10                  15

Glu Arg Val Thr Ile Thr Cys Lys Ala Ser Gln Gly Ile Asn Ser Tyr
            20                  25                  30

Ser Gly Trp Phe Gln Gln Lys Pro Gly Lys Ser Pro Lys Thr Leu Ile
        35                  40                  45

Tyr Arg Gly Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 41
<211> LENGTH: 6
<212> TYPE: PRT
<213> ORGANISM: artificial sequence
<220> FEATURE:
<223> OTHER INFORMATION: CDR1 of G6 VL chain

<400> SEQUENCE: 41

Gln Gly Ile Asn Ser Tyr
1               5

<210> SEQ ID NO 42
<211> LENGTH: 3
<212> TYPE: PRT
<213> ORGANISM: artificial sequence
<220> FEATURE:
<223> OTHER INFORMATION: CDR2 of G6 VL chain

<400> SEQUENCE: 42

Arg Gly Asn
1

<210> SEQ ID NO 43
<211> LENGTH: 9
<212> TYPE: PRT
<213> ORGANISM: artificial sequence
<220> FEATURE:
<223> OTHER INFORMATION: CDR3 of G6 VL chain

<400> SEQUENCE: 43

Leu Gln Tyr Asp Glu Phe Pro Tyr Thr
1               5

<210> SEQ ID NO 44
<211> LENGTH: 118
<212> TYPE: PRT
<213> ORGANISM: artificial sequence
<220> FEATURE:
<223> OTHER INFORMATION: G3 heavy chain variable region

<400> SEQUENCE: 44

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Asn Phe Thr Asn Tyr
            20                  25                  30

Trp Ile Asn Trp Val Lys Leu Arg Pro Gly Gln Gly Leu Glu Trp Ile
        35                  40                  45

Gly Glu Ile Tyr Pro Gly Ser Gly Ser Thr Asn Tyr Asn Glu Lys Phe
    50                  55                  60

```
Lys Ser Lys Ala Thr Leu Thr Ala Asp Thr Ser Ser Thr Ala Tyr
 65                  70                  75                  80

Met Gln Leu Ser Ser Leu Ala Ser Glu Asp Ser Ala Leu Tyr Tyr Cys
                 85                  90                  95

Ala Arg Asp Gly Asn Tyr Tyr Ala Met Asp Tyr Trp Gly Gln Gly Thr
            100                 105                 110

Ser Val Thr Val Ser Ser
        115

<210> SEQ ID NO 45
<211> LENGTH: 8
<212> TYPE: PRT
<213> ORGANISM: artificial sequence
<220> FEATURE:
<223> OTHER INFORMATION: CDR1 of G3 VH chain

<400> SEQUENCE: 45

Gly Tyr Asn Phe Thr Asn Tyr Trp
1               5

<210> SEQ ID NO 46
<211> LENGTH: 8
<212> TYPE: PRT
<213> ORGANISM: artificial sequence
<220> FEATURE:
<223> OTHER INFORMATION: CDR2 of G3 VH chain

<400> SEQUENCE: 46

Ile Tyr Pro Gly Ser Gly Ser Thr
1               5

<210> SEQ ID NO 47
<211> LENGTH: 11
<212> TYPE: PRT
<213> ORGANISM: artificial sequence
<220> FEATURE:
<223> OTHER INFORMATION: CDR3 of G3 VH chain

<400> SEQUENCE: 47

Ala Arg Asp Gly Asn Tyr Tyr Ala Met Asp Tyr
1               5                  10

<210> SEQ ID NO 48
<211> LENGTH: 108
<212> TYPE: PRT
<213> ORGANISM: artificial sequence
<220> FEATURE:
<223> OTHER INFORMATION: G3 light chain variable region

<400> SEQUENCE: 48

Asp Ile Gln Met Thr Gln Thr Thr Ser Ser Leu Ser Ala Ser Leu Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ala Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95
```

```
Tyr Thr Phe Gly Gly Gly Thr Lys Leu Glu Ile Lys
            100                 105

<210> SEQ ID NO 49
<211> LENGTH: 6
<212> TYPE: PRT
<213> ORGANISM: artificial sequence
<220> FEATURE:
<223> OTHER INFORMATION: CDR1 of G3 VL chain

<400> SEQUENCE: 49

Gln Asp Ile Asn Asn Tyr
1               5

<210> SEQ ID NO 50
<211> LENGTH: 3
<212> TYPE: PRT
<213> ORGANISM: artificial sequence
<220> FEATURE:
<223> OTHER INFORMATION: CDR2 of G3 VL chain

<400> SEQUENCE: 50

Tyr Thr Ser
1

<210> SEQ ID NO 51
<211> LENGTH: 10
<212> TYPE: PRT
<213> ORGANISM: artificial sequence
<220> FEATURE:
<223> OTHER INFORMATION: CDR3 of G3 VL chain

<400> SEQUENCE: 51

Gln Gln Gly Asn Thr Leu Pro Pro Tyr Thr
1               5                   10

<210> SEQ ID NO 52
<211> LENGTH: 118
<212> TYPE: PRT
<213> ORGANISM: artificial sequence
<220> FEATURE:
<223> OTHER INFORMATION: H10 heavy chain variable region

<400> SEQUENCE: 52

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Thr Gly Ala Ser Ala Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Ile Thr Thr Ser Thr Trp Tyr Phe Asp Val Trp Gly Ala Gly Thr
            100                 105                 110

Thr Val Thr Val Ser Ser
        115

<210> SEQ ID NO 53
```

```
<211> LENGTH: 8
<212> TYPE: PRT
<213> ORGANISM: artificial sequence
<220> FEATURE:
<223> OTHER INFORMATION: CDR1 of H10 VH chain

<400> SEQUENCE: 53

Gly Phe Thr Phe Ser Ser Tyr Ala
1               5

<210> SEQ ID NO 54
<211> LENGTH: 7
<212> TYPE: PRT
<213> ORGANISM: artificial sequence
<220> FEATURE:
<223> OTHER INFORMATION: CDR2 of H10 VH chain

<400> SEQUENCE: 54

Ile Ser Thr Gly Ala Ser Ala
1               5

<210> SEQ ID NO 55
<211> LENGTH: 12
<212> TYPE: PRT
<213> ORGANISM: artificial sequence
<220> FEATURE:
<223> OTHER INFORMATION: CDR3 of H10 VH chain

<400> SEQUENCE: 55

Ala Arg Ile Thr Thr Ser Thr Trp Tyr Phe Asp Val
1               5                   10

<210> SEQ ID NO 56
<211> LENGTH: 107
<212> TYPE: PRT
<213> ORGANISM: artificial sequence
<220> FEATURE:
<223> OTHER INFORMATION: H10 light chain variable region

<400> SEQUENCE: 56

Asp Ile Lys Met Thr Gln Ser Pro Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
                35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
                100                 105

<210> SEQ ID NO 57
<211> LENGTH: 6
<212> TYPE: PRT
<213> ORGANISM: artificial sequence
<220> FEATURE:
<223> OTHER INFORMATION: CDR1 of H10 VL chain

<400> SEQUENCE: 57

Gln Asp Ile Asn Ser Tyr
```

<210> SEQ ID NO 58
<211> LENGTH: 3
<212> TYPE: PRT
<213> ORGANISM: artificial sequence
<220> FEATURE:
<223> OTHER INFORMATION: CDR2 of H10 VL chain

<400> SEQUENCE: 58

Arg Ala Asn
1

<210> SEQ ID NO 59
<211> LENGTH: 9
<212> TYPE: PRT
<213> ORGANISM: artificial sequence
<220> FEATURE:
<223> OTHER INFORMATION: CDR3 of H10 VL chain

<400> SEQUENCE: 59

Leu Gln Tyr Asp Glu Phe Pro Tyr Thr
1               5

<210> SEQ ID NO 60
<211> LENGTH: 114
<212> TYPE: PRT
<213> ORGANISM: artificial sequence
<220> FEATURE:
<223> OTHER INFORMATION: 2A4 heavy chain variable region

<400> SEQUENCE: 60

Glu Val Lys Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Leu Gln Gly Phe Ala Tyr Trp Gly Gln Gly Thr Pro Leu Thr Val
            100                 105                 110

Ser Ser

<210> SEQ ID NO 61
<211> LENGTH: 8
<212> TYPE: PRT
<213> ORGANISM: artificial sequence
<220> FEATURE:
<223> OTHER INFORMATION: CDR1 of 2A4 VH chain

<400> SEQUENCE: 61

Gly Tyr Thr Phe Thr Glu Tyr Thr
1               5

<210> SEQ ID NO 62
<211> LENGTH: 8
<212> TYPE: PRT
<213> ORGANISM: artificial sequence

```
<220> FEATURE:
<223> OTHER INFORMATION: CDR2 of 2A4 VH chain

<400> SEQUENCE: 62

Ile Asn Pro Asn Asn Gly Gly Thr
1               5

<210> SEQ ID NO 63
<211> LENGTH: 7
<212> TYPE: PRT
<213> ORGANISM: artificial sequence
<220> FEATURE:
<223> OTHER INFORMATION: CDR3 of 2A4 VH chain

<400> SEQUENCE: 63

Ala Leu Gln Gly Phe Ala Tyr
1               5

<210> SEQ ID NO 64
<211> LENGTH: 107
<212> TYPE: PRT
<213> ORGANISM: artificial sequence
<220> FEATURE:
<223> OTHER INFORMATION: 2A4 light chain variable region

<400> SEQUENCE: 64

Met Glu Ile Glu Ile Thr Gln Thr Pro Ala Leu Met Ser Ala Ser Pro
1               5                   10                  15

Gly Glu Lys Val Thr Met Thr Cys Ser Ala Ser Ser Val Ser Tyr
                20                  25                  30

Met Tyr Trp Tyr Gln Gln Lys Pro Arg Ser Ser Pro Lys Pro Trp Ile
            35                  40                  45

Tyr Leu Thr Ser Asn Leu Ala Ser Gly Val Pro Ala Arg Phe Ser Gly
        50                  55                  60

Ser Gly Ser Gly Thr Ser Tyr Ser Leu Thr Ile Ser Ser Met Glu Ala
65                  70                  75                  80

Glu Asp Ala Ala Thr Tyr Tyr Cys Gln Gln Trp Ser Ser Asn Pro Tyr
                85                  90                  95

Thr Phe Gly Gly Gly Thr Arg Leu Glu Leu Lys
            100                 105

<210> SEQ ID NO 65
<211> LENGTH: 5
<212> TYPE: PRT
<213> ORGANISM: artificial sequence
<220> FEATURE:
<223> OTHER INFORMATION: CDR1 of 2A4 VL chain

<400> SEQUENCE: 65

Ser Ser Val Ser Tyr
1               5

<210> SEQ ID NO 66
<211> LENGTH: 3
<212> TYPE: PRT
<213> ORGANISM: artificial sequence
<220> FEATURE:
<223> OTHER INFORMATION: CDR2 of 2A4 VL chain

<400> SEQUENCE: 66

Leu Thr Ser
1
```

<210> SEQ ID NO 67
<211> LENGTH: 9
<212> TYPE: PRT
<213> ORGANISM: artificial sequence
<220> FEATURE:
<223> OTHER INFORMATION: CDR3 of 2A4 VL chain

<400> SEQUENCE: 67

Gln Gln Trp Ser Ser Asn Pro Tyr Thr
1               5

<210> SEQ ID NO 68
<211> LENGTH: 119
<212> TYPE: PRT
<213> ORGANISM: artificial sequence
<220> FEATURE:
<223> OTHER INFORMATION: 1C11 heavy chain variable region

<400> SEQUENCE: 68

Glu Val Lys Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Gly Asp Ser Ala Val Tyr Tyr Cys
                85                  90                  95

Ala Arg Arg Val Leu Trp Leu Arg Arg Gly Asp Tyr Trp Gly Gln Gly
            100                 105                 110

Thr Ile Leu Thr Val Ser Ala
        115

<210> SEQ ID NO 69
<211> LENGTH: 8
<212> TYPE: PRT
<213> ORGANISM: artificial sequence
<220> FEATURE:
<223> OTHER INFORMATION: CDR1 of 1C11 VH chain

<400> SEQUENCE: 69

Gly Tyr Thr Phe Thr Ser Tyr Thr
1               5

<210> SEQ ID NO 70
<211> LENGTH: 8
<212> TYPE: PRT
<213> ORGANISM: artificial sequence
<220> FEATURE:
<223> OTHER INFORMATION: CDR2 of 1C11 VH chain

<400> SEQUENCE: 70

Ile Asn Pro Ser Ser Gly Tyr Thr
1               5

<210> SEQ ID NO 71
<211> LENGTH: 12
<212> TYPE: PRT
<213> ORGANISM: artificial sequence
<220> FEATURE:
<223> OTHER INFORMATION: CDR3 of 1C11 VH chain

```
<400> SEQUENCE: 71

Ala Arg Arg Val Leu Trp Leu Arg Arg Gly Asp Tyr
1               5                   10

<210> SEQ ID NO 72
<211> LENGTH: 108
<212> TYPE: PRT
<213> ORGANISM: artificial sequence
<220> FEATURE:
<223> OTHER INFORMATION: 1C11 light chain variable region

<400> SEQUENCE: 72

Met Glu Val Leu Ile Thr Gln Thr Pro Ser Ser Leu Ser Ala Ser Leu
1               5                   10                  15

Gly Glu Arg Val Ser Leu Thr Cys Arg Ala Ser Gln Asp Ile Gly Ser
            20                  25                  30

Ser Leu Asn Trp Leu Gln Gln Glu Pro Asp Gly Thr Ile Lys Arg Leu
        35                  40                  45

Ile Tyr Ala Thr Ser Ser Leu Asp Ser Gly Val Pro Lys Arg Phe Ser
    50                  55                  60

Gly Ser Arg Ser Gly Ser Asp Tyr Ser Leu Thr Ile Ser Ser Leu Glu
65                  70                  75                  80

Ser Glu Asp Phe Val Asp Tyr Tyr Cys Leu Gln Tyr Ala Ser Ser Pro
                85                  90                  95

Tyr Thr Phe Gly Gly Gly Thr Lys Leu Glu Leu Lys
            100                 105

<210> SEQ ID NO 73
<211> LENGTH: 6
<212> TYPE: PRT
<213> ORGANISM: artificial sequence
<220> FEATURE:
<223> OTHER INFORMATION: CDR1 of 1C11 VL chain

<400> SEQUENCE: 73

Gln Asp Ile Gly Ser Ser
1               5

<210> SEQ ID NO 74
<211> LENGTH: 3
<212> TYPE: PRT
<213> ORGANISM: artificial sequence
<220> FEATURE:
<223> OTHER INFORMATION: CDR2 of 1C11 VL chain

<400> SEQUENCE: 74

Ala Thr Ser
1

<210> SEQ ID NO 75
<211> LENGTH: 7
<212> TYPE: PRT
<213> ORGANISM: artificial sequence
<220> FEATURE:
<223> OTHER INFORMATION: CDR3 of 1C11 VL chain

<400> SEQUENCE: 75

Leu Gln Tyr Ala Ser Ser Pro
1               5

<210> SEQ ID NO 76
<211> LENGTH: 835
```

<212> TYPE: PRT
<213> ORGANISM: artificial sequence
<220> FEATURE:
<223> OTHER INFORMATION: anti-ROR1 2A2 mcCAR

<400> SEQUENCE: 76

```
Met Ile Pro Ala Val Val Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
                35                  40                  45

Gln Val Arg Lys Ala Ala Ile Thr Ser Tyr Glu Lys Ser Arg Val Lys
    50                  55                  60

Phe Ser Arg Ser Ala Asp Ala Pro Ala Tyr Gln Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
            100                 105                 110

Lys Asn Pro Gln Glu Gly Leu Tyr Asn Glu Leu Gln Lys Asp Lys Met
        115                 120                 125

Ala Glu Ala Tyr Ser Glu Ile Gly Met Lys Gly Glu Arg Arg Arg Gly
130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg Gly Ser Gly
                165                 170                 175

Ala Thr Asn Phe Ser Leu Leu Lys Gln Ala Gly Asp Val Glu Glu Asn
            180                 185                 190

Pro Gly Pro Met Ala Pro Ala Met Glu Ser Pro Thr Leu Leu Cys Val
        195                 200                 205

Ala Leu Leu Phe Phe Ala Pro Asp Gly Val Leu Ala Gln Val Gln Leu
210                 215                 220

Gln Gln Ser Gly Ala Glu Leu Val Arg Pro Gly Ala Ser Val Thr Leu
225                 230                 235                 240

Ser Cys Lys Ala Ser Gly Tyr Thr Phe Ser Asp Tyr Glu Met His Trp
                245                 250                 255

Val Ile Gln Thr Pro Val His Gly Leu Glu Trp Ile Gly Ala Ile Asp
            260                 265                 270

Pro Glu Thr Gly Gly Thr Ala Tyr Asn Gln Lys Phe Lys Gly Lys Ala
        275                 280                 285

Ile Leu Thr Ala Asp Lys Ser Ser Ser Thr Ala Tyr Met Glu Leu Arg
290                 295                 300

Ser Leu Thr Ser Glu Asp Ser Ala Val Tyr Tyr Cys Thr Gly Tyr Tyr
305                 310                 315                 320

Asp Tyr Asp Ser Phe Thr Tyr Trp Gly Gln Gly Thr Leu Val Thr Val
                325                 330                 335

Ser Ala Gly Gly Gly Gly Ser Gly Gly Gly Gly Ser Gly Gly Gly Gly
            340                 345                 350

Ser Asp Ile Val Met Thr Gln Ser Gln Lys Ile Met Ser Thr Thr Val
        355                 360                 365

Gly Asp Arg Val Ser Ile Thr Cys Lys Ala Ser Gln Asn Val Asp Ala
370                 375                 380
```

```
Ala Val Ala Trp Tyr Gln Gln Lys Pro Gly Gln Ser Pro Lys Leu Leu
385                 390                 395                 400

Ile Tyr Ser Ala Ser Asn Arg Tyr Thr Gly Val Pro Asp Arg Phe Thr
            405                 410                 415

Gly Ser Gly Ser Gly Thr Asp Phe Thr Leu Thr Ile Ser Asn Met Gln
                420                 425                 430

Ser Glu Asp Leu Ala Asp Tyr Phe Cys Gln Gln Tyr Asp Ile Tyr Pro
            435                 440                 445

Tyr Thr Phe Gly Gly Gly Thr Lys Leu Glu Ile Lys Thr Thr Thr Pro
        450                 455                 460

Ala Pro Arg Pro Pro Thr Pro Ala Pro Thr Ile Ala Ser Gln Pro Leu
465                 470                 475                 480

Ser Leu Arg Pro Glu Ala Cys Arg Pro Ala Ala Gly Gly Ala Val His
            485                 490                 495

Thr Arg Gly Leu Asp Phe Ala Cys Asp Phe Phe Ile Pro Leu Leu Val
                500                 505                 510

Val Ile Leu Phe Ala Val Asp Thr Gly Leu Phe Ile Ser Thr Gln Gln
        515                 520                 525

Gln Val Thr Phe Leu Leu Lys Ile Lys Arg Thr Arg Lys Gly Phe Arg
530                 535                 540

Leu Leu Asn Pro His Pro Lys Pro Asn Pro Lys Asn Asn Gly Ser Gly
545                 550                 555                 560

Glu Gly Arg Gly Ser Leu Leu Thr Cys Gly Asp Val Glu Glu Asn Pro
            565                 570                 575

Gly Pro Met Asp Thr Glu Ser Asn Arg Arg Ala Asn Leu Ala Leu Pro
                580                 585                 590

Gln Glu Pro Ser Ser Val Pro Ala Phe Glu Val Leu Glu Ile Ser Pro
            595                 600                 605

Gln Glu Val Ser Ser Gly Arg Leu Leu Lys Ser Ala Ser Ser Pro Pro
        610                 615                 620

Leu His Thr Trp Leu Thr Val Leu Lys Lys Glu Gln Glu Phe Leu Gly
625                 630                 635                 640

Val Thr Gln Ile Leu Thr Ala Met Ile Cys Leu Cys Phe Gly Thr Val
            645                 650                 655

Val Cys Ser Val Leu Asp Ile Ser His Ile Glu Gly Asp Ile Phe Ser
                660                 665                 670

Ser Phe Lys Ala Gly Tyr Pro Phe Trp Gly Ala Ile Phe Phe Ser Ile
        675                 680                 685

Ser Gly Met Leu Ser Ile Ile Ser Glu Arg Arg Asn Ala Thr Tyr Leu
690                 695                 700

Val Arg Gly Ser Leu Gly Ala Asn Thr Ala Ser Ser Ile Ala Gly Gly
705                 710                 715                 720

Thr Gly Ile Thr Ile Leu Ile Ile Asn Leu Lys Lys Ser Leu Ala Tyr
            725                 730                 735

Ile His Ile His Ser Cys Gln Lys Phe Phe Gly Thr Lys Cys Phe Met
                740                 745                 750

Ala Ser Phe Ser Thr Glu Ile Val Val Met Met Leu Phe Leu Thr Ile
        755                 760                 765

Leu Gly Leu Gly Ser Ala Val Ser Leu Thr Ile Cys Gly Ala Gly Glu
770                 775                 780

Glu Leu Lys Gly Asn Lys Val Pro Glu Lys Arg Gly Arg Lys Lys Leu
785                 790                 795                 800

Leu Tyr Ile Phe Lys Gln Pro Phe Met Arg Pro Val Gln Thr Thr Gln
```

```
                805                 810                 815
Glu Glu Asp Gly Cys Ser Cys Arg Phe Pro Glu Glu Glu Gly Gly
            820                 825                 830

Cys Glu Leu
        835

<210> SEQ ID NO 77
<211> LENGTH: 836
<212> TYPE: PRT
<213> ORGANISM: artificial sequence
<220> FEATURE:
<223> OTHER INFORMATION: anti- ROR1   4A5  mcCAR

<400> SEQUENCE: 77

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Arg Val Lys
    50                  55                  60

Phe Ser Arg Ser Ala Asp Ala Pro Ala Tyr Gln Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
            100                 105                 110

Lys Asn Pro Gln Glu Gly Leu Tyr Asn Glu Leu Gln Lys Asp Lys Met
        115                 120                 125

Ala Glu Ala Tyr Ser Glu Ile Gly Met Lys Gly Glu Arg Arg Arg Gly
    130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg Gly Ser Gly
                165                 170                 175

Ala Thr Asn Phe Ser Leu Leu Lys Gln Ala Gly Asp Val Glu Glu Asn
            180                 185                 190

Pro Gly Pro Met Ala Pro Ala Met Glu Ser Pro Thr Leu Leu Cys Val
        195                 200                 205

Ala Leu Leu Phe Phe Ala Pro Asp Gly Val Leu Ala Glu Val Lys Leu
    210                 215                 220

Val Glu Ser Gly Gly Gly Leu Val Lys Pro Gly Gly Ser Leu Lys Leu
225                 230                 235                 240

Ser Cys Ala Ala Ser Gly Phe Thr Phe Ser Ser Tyr Ala Met Ser Trp
                245                 250                 255

Val Arg Gln Ile Pro Glu Lys Arg Leu Glu Trp Val Ala Ser Ile Ser
            260                 265                 270

Arg Gly Gly Thr Thr Tyr Tyr Pro Asp Ser Val Lys Gly Arg Phe Thr
        275                 280                 285

Ile Ser Arg Asp Asn Val Arg Asn Ile Leu Tyr Leu Gln Met Ser Ser
    290                 295                 300

Leu Arg Ser Glu Asp Thr Ala Met Tyr Tyr Cys Gly Arg Tyr Asp Tyr
305                 310                 315                 320

Asp Gly Tyr Tyr Ala Met Asp Tyr Trp Gly Gln Gly Thr Ser Val Thr
```

-continued

```
                325                 330                 335
Val Ser Ser Gly Gly Gly Ser Gly Gly Gly Ser Gly Gly
            340                 345                 350
Gly Ser Asp Ile Lys Met Thr Gln Ser Pro Ser Ser Met Tyr Ala Ser
            355                 360                 365
Leu Gly Glu Arg Val Thr Ile Thr Cys Lys Ala Ser Pro Asp Ile Asn
            370                 375                 380
Ser Tyr Leu Ser Trp Phe Gln Gln Lys Pro Gly Lys Ser Pro Lys Thr
385                 390                 395                 400
Leu Ile Tyr Arg Ala Asn Arg Leu Val Asp Gly Val Pro Ser Arg Phe
                    405                 410                 415
Ser Gly Gly Gly Ser Gly Gln Asp Tyr Ser Leu Thr Ile Asn Ser Leu
                    420                 425                 430
Glu Tyr Glu Asp Met Gly Ile Tyr Tyr Cys Leu Gln Tyr Asp Glu Phe
                    435                 440                 445
Pro Tyr Thr Phe Gly Gly Gly Thr Lys Leu Glu Met Lys Thr Thr Thr
            450                 455                 460
Pro Ala Pro Arg Pro Pro Thr Pro Ala Pro Thr Ile Ala Ser Gln Pro
465                 470                 475                 480
Leu Ser Leu Arg Pro Glu Ala Cys Arg Pro Ala Ala Gly Gly Ala Val
                    485                 490                 495
His Thr Arg Gly Leu Asp Phe Ala Cys Asp Phe Phe Ile Pro Leu Leu
            500                 505                 510
Val Val Ile Leu Phe Ala Val Asp Thr Gly Leu Phe Ile Ser Thr Gln
            515                 520                 525
Gln Gln Val Thr Phe Leu Leu Lys Ile Lys Arg Thr Arg Lys Gly Phe
            530                 535                 540
Arg Leu Leu Asn Pro His Pro Lys Pro Asn Pro Lys Asn Asn Gly Ser
545                 550                 555                 560
Gly Glu Gly Arg Gly Ser Leu Leu Thr Cys Gly Asp Val Glu Glu Asn
                    565                 570                 575
Pro Gly Pro Met Asp Thr Glu Ser Asn Arg Arg Ala Asn Leu Ala Leu
                    580                 585                 590
Pro Gln Glu Pro Ser Ser Val Pro Ala Phe Glu Val Leu Glu Ile Ser
                    595                 600                 605
Pro Gln Glu Val Ser Ser Gly Arg Leu Leu Lys Ser Ala Ser Ser Pro
            610                 615                 620
Pro Leu His Thr Trp Leu Thr Val Leu Lys Lys Glu Gln Glu Phe Leu
625                 630                 635                 640
Gly Val Thr Gln Ile Leu Thr Ala Met Ile Cys Leu Cys Phe Gly Thr
                    645                 650                 655
Val Val Cys Ser Val Leu Asp Ile Ser His Ile Glu Gly Asp Ile Phe
            660                 665                 670
Ser Ser Phe Lys Ala Gly Tyr Pro Phe Trp Gly Ala Ile Phe Phe Ser
            675                 680                 685
Ile Ser Gly Met Leu Ser Ile Ile Ser Glu Arg Arg Asn Ala Thr Tyr
            690                 695                 700
Leu Val Arg Gly Ser Leu Gly Ala Asn Thr Ala Ser Ser Ile Ala Gly
705                 710                 715                 720
Gly Thr Gly Ile Thr Ile Leu Ile Ile Asn Leu Lys Lys Ser Leu Ala
                    725                 730                 735
Tyr Ile His Ile His Ser Cys Gln Lys Phe Phe Glu Thr Lys Cys Phe
                    740                 745                 750
```

Met Ala Ser Phe Ser Thr Glu Ile Val Val Met Met Leu Phe Leu Thr
        755                 760                 765

Ile Leu Gly Leu Gly Ser Ala Val Ser Leu Thr Ile Cys Gly Ala Gly
770                 775                 780

Glu Glu Leu Lys Gly Asn Lys Val Pro Glu Lys Arg Gly Arg Lys Lys
785                 790                 795                 800

Leu Leu Tyr Ile Phe Lys Gln Pro Phe Met Arg Pro Val Gln Thr Thr
                805                 810                 815

Gln Glu Glu Asp Gly Cys Ser Cys Arg Phe Pro Glu Glu Glu Gly
                820                 825                 830

Gly Cys Glu Leu
        835

<210> SEQ ID NO 78
<211> LENGTH: 833
<212> TYPE: PRT
<213> ORGANISM: artificial sequence
<220> FEATURE:
<223> OTHER INFORMATION: anti- ROR1   D10 mcCAR

<400> SEQUENCE: 78

Met Ile Pro Ala Val Leu Leu Leu Leu Leu Val Glu Gln Ala
1               5                   10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Arg Val Lys
50                  55                  60

Phe Ser Arg Ser Ala Asp Ala Pro Ala Tyr Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
            100                 105                 110

Lys Asn Pro Gln Glu Gly Leu Tyr Asn Glu Leu Gln Lys Asp Lys Met
        115                 120                 125

Ala Glu Ala Tyr Ser Glu Ile Gly Met Lys Gly Glu Arg Arg Arg Gly
    130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg Gly Ser Gly
                165                 170                 175

Ala Thr Asn Phe Ser Leu Leu Lys Gln Ala Gly Asp Val Glu Glu Asn
            180                 185                 190

Pro Gly Pro Met Ala Pro Ala Met Glu Ser Pro Thr Leu Leu Cys Val
        195                 200                 205

Ala Leu Leu Phe Phe Ala Pro Asp Gly Val Leu Ala Gln Val Gln Leu
    210                 215                 220

Lys Glu Ser Gly Pro Gly Leu Val Ala Pro Ser Gln Thr Leu Ser Ile
225                 230                 235                 240

Thr Cys Thr Val Ser Gly Phe Ser Leu Thr Ser Tyr Gly Val His Trp
                245                 250                 255

Val Arg Gln Pro Pro Gly Lys Gly Leu Glu Trp Leu Gly Val Ile Trp
            260                 265                 270

```
Ala Gly Gly Phe Thr Asn Tyr Asn Ser Ala Leu Lys Ser Arg Leu Ser
            275                 280                 285

Ile Ser Lys Asp Asn Ser Lys Ser Gln Val Leu Leu Lys Met Thr Ser
        290                 295                 300

Leu Gln Thr Asp Asp Thr Ala Met Tyr Tyr Cys Ala Arg Arg Gly Ser
305                 310                 315                 320

Ser Tyr Ser Met Asp Tyr Trp Gly Gln Gly Thr Ser Val Thr Val Ser
                325                 330                 335

Ser Gly Gly Gly Gly Ser Gly Gly Gly Gly Ser Gly Gly Gly Gly Ser
            340                 345                 350

Glu Ile Val Leu Ser Gln Ser Pro Ala Ile Thr Ala Ala Ser Leu Gly
            355                 360                 365

Gln Lys Val Thr Ile Thr Cys Ser Ala Ser Ser Asn Val Ser Tyr Ile
    370                 375                 380

His Trp Tyr Gln Gln Arg Ser Gly Thr Ser Pro Arg Pro Trp Ile Tyr
385                 390                 395                 400

Glu Ile Ser Lys Leu Ala Ser Gly Val Pro Val Arg Phe Ser Gly Ser
                405                 410                 415

Gly Ser Gly Thr Ser Tyr Ser Leu Thr Ile Ser Ser Met Glu Ala Glu
            420                 425                 430

Asp Ala Ala Ile Tyr Tyr Cys Gln Gln Trp Asn Tyr Pro Leu Ile Thr
            435                 440                 445

Phe Gly Ser Gly Thr Lys Leu Glu Ile Gln Thr Thr Thr Pro Ala Pro
    450                 455                 460

Arg Pro Pro Thr Pro Ala Pro Thr Ile Ala Ser Gln Pro Leu Ser Leu
465                 470                 475                 480

Arg Pro Glu Ala Cys Arg Pro Ala Ala Gly Gly Ala Val His Thr Arg
                485                 490                 495

Gly Leu Asp Phe Ala Cys Asp Phe Phe Ile Pro Leu Leu Val Val Ile
            500                 505                 510

Leu Phe Ala Val Asp Thr Gly Leu Phe Ile Ser Thr Gln Gln Gln Val
    515                 520                 525

Thr Phe Leu Leu Lys Ile Lys Arg Thr Arg Lys Gly Phe Arg Leu Leu
            530                 535                 540

Asn Pro His Pro Lys Pro Asn Pro Lys Asn Asn Gly Ser Gly Glu Gly
545                 550                 555                 560

Arg Gly Ser Leu Leu Thr Cys Gly Asp Val Glu Glu Asn Pro Gly Pro
                565                 570                 575

Met Asp Thr Glu Ser Asn Arg Arg Ala Asn Leu Ala Leu Pro Gln Glu
            580                 585                 590

Pro Ser Ser Val Pro Ala Phe Glu Val Leu Glu Ile Ser Pro Gln Glu
            595                 600                 605

Val Ser Ser Gly Arg Leu Leu Lys Ser Ala Ser Ser Pro Pro Leu His
    610                 615                 620

Thr Trp Leu Thr Val Leu Lys Lys Glu Gln Glu Phe Leu Gly Val Thr
625                 630                 635                 640

Gln Ile Leu Thr Ala Met Ile Cys Leu Cys Phe Gly Thr Val Val Cys
                645                 650                 655

Ser Val Leu Asp Ile Ser His Ile Glu Gly Asp Ile Phe Ser Ser Phe
            660                 665                 670

Lys Ala Gly Tyr Pro Phe Trp Gly Ala Ile Phe Phe Ser Ile Ser Gly
            675                 680                 685
```

```
Met Leu Ser Ile Ile Ser Glu Arg Arg Asn Ala Thr Tyr Leu Val Arg
    690                 695                 700

Gly Ser Leu Gly Ala Asn Thr Ala Ser Ser Ile Ala Gly Gly Thr Gly
705                 710                 715                 720

Ile Thr Ile Leu Ile Ile Asn Leu Lys Lys Ser Leu Ala Tyr Ile His
                725                 730                 735

Ile His Ser Cys Gln Lys Phe Phe Glu Thr Lys Cys Phe Met Ala Ser
                740                 745                 750

Phe Ser Thr Glu Ile Val Val Met Met Leu Phe Leu Thr Ile Leu Gly
            755                 760                 765

Leu Gly Ser Ala Val Ser Leu Thr Ile Cys Gly Ala Gly Glu Glu Leu
770                 775                 780

Lys Gly Asn Lys Val Pro Glu Lys Arg Gly Arg Lys Lys Leu Leu Tyr
785                 790                 795                 800

Ile Phe Lys Gln Pro Phe Met Arg Pro Val Gln Thr Thr Gln Glu Glu
                805                 810                 815

Asp Gly Cys Ser Cys Arg Phe Pro Glu Glu Glu Gly Gly Cys Glu
                820                 825                 830

Leu
```

<210> SEQ ID NO 79
<211> LENGTH: 836
<212> TYPE: PRT
<213> ORGANISM: artificial sequence
<220> FEATURE:
<223> OTHER INFORMATION: anti- ROR1   G6 mcCAR

<400> SEQUENCE: 79

```
Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Arg Val Lys
    50                  55                  60

Phe Ser Arg Ser Ala Asp Ala Pro Ala Tyr Gln Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
            100                 105                 110

Lys Asn Pro Gln Glu Gly Leu Tyr Asn Glu Leu Gln Lys Asp Lys Met
        115                 120                 125

Ala Glu Ala Tyr Ser Glu Ile Gly Met Lys Gly Glu Arg Arg Arg Gly
    130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg Gly Ser Gly
                165                 170                 175

Ala Thr Asn Phe Ser Leu Leu Lys Gln Ala Gly Asp Val Glu Glu Asn
            180                 185                 190

Pro Gly Pro Met Ala Pro Ala Met Glu Ser Pro Thr Leu Leu Cys Val
        195                 200                 205

Ala Leu Leu Phe Phe Ala Pro Asp Gly Val Leu Ala Glu Val Gln Leu
```

```
            210                 215                 220
Gln Gln Ser Gly Pro Glu Leu Glu Lys Pro Gly Ala Ser Val Lys Ile
225                 230                 235                 240

Ser Cys Lys Ala Ser Gly Phe Ala Phe Thr Gly Tyr Asn Met Asn Trp
                245                 250                 255

Val Lys Gln Thr Asn Gly Lys Ser Leu Glu Trp Ile Gly Ser Ile Asp
                260                 265                 270

Pro Tyr Tyr Gly Gly Ser Thr Tyr Asn Gln Lys Phe Lys Asp Lys Ala
            275                 280                 285

Thr Leu Thr Val Asp Lys Ser Ser Ser Thr Ala Tyr Met Gln Leu Lys
        290                 295                 300

Ser Leu Thr Ser Asp Asp Ser Ala Val Tyr Tyr Cys Ala Arg Ser Pro
305                 310                 315                 320

Gly Gly Asp Tyr Ala Met Asp Tyr Trp Gly Gln Gly Thr Ser Val Thr
                325                 330                 335

Val Ser Ser Gly Gly Gly Gly Ser Gly Gly Gly Gly Ser Gly Gly Gly
                340                 345                 350

Gly Ser Asp Ile Lys Met Thr Gln Ser Pro Ser Ser Met Tyr Ala Ser
            355                 360                 365

Val Gly Glu Arg Val Thr Ile Thr Cys Lys Ala Ser Gln Gly Ile Asn
        370                 375                 380

Ser Tyr Ser Gly Trp Phe Gln Gln Lys Pro Gly Lys Ser Pro Lys Thr
385                 390                 395                 400

Leu Ile Tyr Arg Gly Asn Arg Leu Val Asp Gly Val Pro Ser Arg Phe
                405                 410                 415

Ser Gly Ser Gly Ser Gly Gln Asp Tyr Ser Leu Thr Ile Ser Ser Leu
                420                 425                 430

Glu Tyr Glu Asp Met Gly Ile Tyr Tyr Cys Leu Gln Tyr Asp Glu Phe
            435                 440                 445

Pro Tyr Thr Phe Gly Gly Gly Thr Lys Leu Glu Ile Lys Thr Thr Thr
        450                 455                 460

Pro Ala Pro Arg Pro Pro Thr Pro Ala Pro Thr Ile Ala Ser Gln Pro
465                 470                 475                 480

Leu Ser Leu Arg Pro Glu Ala Cys Arg Pro Ala Ala Gly Gly Ala Val
                485                 490                 495

His Thr Arg Gly Leu Asp Phe Ala Cys Asp Phe Phe Ile Pro Leu Leu
            500                 505                 510

Val Val Ile Leu Phe Ala Val Asp Thr Gly Leu Phe Ile Ser Thr Gln
        515                 520                 525

Gln Gln Val Thr Phe Leu Leu Lys Ile Lys Arg Thr Arg Lys Gly Phe
        530                 535                 540

Arg Leu Leu Asn Pro His Pro Lys Pro Asn Pro Lys Asn Asn Gly Ser
545                 550                 555                 560

Gly Glu Gly Arg Gly Ser Leu Leu Thr Cys Gly Asp Val Glu Glu Asn
                565                 570                 575

Pro Gly Pro Met Asp Thr Glu Ser Asn Arg Arg Ala Asn Leu Ala Leu
            580                 585                 590

Pro Gln Glu Pro Ser Ser Val Pro Ala Phe Glu Val Leu Glu Ile Ser
        595                 600                 605

Pro Gln Glu Val Ser Ser Gly Arg Leu Leu Lys Ser Ala Ser Ser Pro
        610                 615                 620

Pro Leu His Thr Trp Leu Thr Val Leu Lys Lys Glu Gln Glu Phe Leu
625                 630                 635                 640
```

-continued

```
Gly Val Thr Gln Ile Leu Thr Ala Met Ile Cys Leu Cys Phe Gly Thr
                645                 650                 655

Val Val Cys Ser Val Leu Asp Ile Ser His Ile Glu Gly Asp Ile Phe
            660                 665                 670

Ser Ser Phe Lys Ala Gly Tyr Pro Phe Trp Gly Ala Ile Phe Phe Ser
        675                 680                 685

Ile Ser Gly Met Leu Ser Ile Ile Ser Glu Arg Arg Asn Ala Thr Tyr
    690                 695                 700

Leu Val Arg Gly Ser Leu Gly Ala Asn Thr Ala Ser Ser Ile Ala Gly
705                 710                 715                 720

Gly Thr Gly Ile Thr Ile Leu Ile Ile Asn Leu Lys Lys Ser Leu Ala
                725                 730                 735

Tyr Ile His Ile His Ser Cys Gln Lys Phe Phe Glu Thr Lys Cys Phe
            740                 745                 750

Met Ala Ser Phe Ser Thr Glu Ile Val Val Met Met Leu Phe Leu Thr
        755                 760                 765

Ile Leu Gly Leu Gly Ser Ala Val Ser Leu Thr Ile Cys Gly Ala Gly
    770                 775                 780

Glu Glu Leu Lys Gly Asn Lys Val Pro Glu Lys Arg Gly Arg Lys Lys
785                 790                 795                 800

Leu Leu Tyr Ile Phe Lys Gln Pro Phe Met Arg Pro Val Gln Thr Thr
                805                 810                 815

Gln Glu Glu Asp Gly Cys Ser Cys Arg Phe Pro Glu Glu Glu Glu Gly
            820                 825                 830

Gly Cys Glu Leu
        835

<210> SEQ ID NO 80
<211> LENGTH: 836
<212> TYPE: PRT
<213> ORGANISM: artificial sequence
<220> FEATURE:
<223> OTHER INFORMATION: anti- ROR1   G3 mcCAR

<400> SEQUENCE: 80

Met Ile Pro Ala Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Arg Val Lys
    50                  55                  60

Phe Ser Arg Ser Ala Asp Ala Pro Ala Tyr Gln Gly Gln Asn Gln
65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
            100                 105                 110

Lys Asn Pro Gln Glu Gly Leu Tyr Asn Glu Leu Gln Lys Asp Lys Met
        115                 120                 125

Ala Glu Ala Tyr Ser Glu Ile Gly Met Lys Gly Glu Arg Arg Arg Gly
    130                 135                 140

Lys Gly His Asp Gly Leu Tyr Gln Gly Leu Ser Thr Ala Thr Lys Asp
145                 150                 155                 160
```

Thr Tyr Asp Ala Leu His Met Gln Ala Leu Pro Pro Arg Gly Ser Gly
                165                 170                 175

Ala Thr Asn Phe Ser Leu Leu Lys Gln Ala Gly Asp Val Glu Glu Asn
            180                 185                 190

Pro Gly Pro Met Ala Pro Ala Met Glu Ser Pro Thr Leu Leu Cys Val
        195                 200                 205

Ala Leu Leu Phe Phe Ala Pro Asp Gly Val Leu Ala Gln Val Gln Leu
    210                 215                 220

Gln Gln Pro Gly Ala Glu Leu Val Lys Pro Gly Thr Ser Val Lys Leu
225                 230                 235                 240

Ser Cys Lys Ala Ser Gly Tyr Asn Phe Thr Asn Tyr Trp Ile Asn Trp
                245                 250                 255

Val Lys Leu Arg Pro Gly Gln Gly Leu Glu Trp Ile Gly Glu Ile Tyr
            260                 265                 270

Pro Gly Ser Gly Ser Thr Asn Tyr Asn Glu Lys Phe Lys Ser Lys Ala
        275                 280                 285

Thr Leu Thr Ala Asp Thr Ser Ser Ser Thr Ala Tyr Met Gln Leu Ser
    290                 295                 300

Ser Leu Ala Ser Glu Asp Ser Ala Leu Tyr Tyr Cys Ala Arg Asp Gly
305                 310                 315                 320

Asn Tyr Tyr Ala Met Asp Tyr Trp Gly Gln Gly Thr Ser Val Thr Val
                325                 330                 335

Ser Ser Gly Gly Gly Gly Ser Gly Gly Gly Gly Ser Gly Gly Gly Gly
            340                 345                 350

Ser Asp Ile Gln Met Thr Gln Thr Thr Ser Ser Leu Ser Ala Ser Leu
        355                 360                 365

Gly Asp Arg Val Thr Ile Thr Cys Arg Ala Ser Gln Asp Ile Asn Asn
    370                 375                 380

Tyr Leu Asn Trp Tyr Gln Gln Lys Pro Asp Gly Thr Val Lys Leu Leu
385                 390                 395                 400

Ile Tyr Tyr Thr Ser Ala Leu His Ser Gly Val Pro Ser Arg Phe Ser
                405                 410                 415

Gly Ser Gly Ser Gly Thr Asp Tyr Ser Leu Thr Ile Ser Asn Leu Glu
            420                 425                 430

Gln Glu Asp Ile Ala Thr Tyr Phe Cys Gln Gln Gly Asn Thr Leu Pro
        435                 440                 445

Pro Tyr Thr Phe Gly Gly Gly Thr Lys Leu Glu Ile Lys Thr Thr Thr
    450                 455                 460

Pro Ala Pro Arg Pro Pro Thr Pro Ala Pro Thr Ile Ala Ser Gln Pro
465                 470                 475                 480

Leu Ser Leu Arg Pro Glu Ala Cys Arg Pro Ala Ala Gly Gly Ala Val
                485                 490                 495

His Thr Arg Gly Leu Asp Phe Ala Cys Asp Phe Phe Ile Pro Leu Leu
            500                 505                 510

Val Val Ile Leu Phe Ala Val Asp Thr Gly Leu Phe Ile Ser Thr Gln
        515                 520                 525

Gln Gln Val Thr Phe Leu Leu Lys Ile Lys Arg Thr Arg Lys Gly Phe
    530                 535                 540

Arg Leu Leu Asn Pro His Pro Lys Pro Asn Pro Lys Asn Asn Gly Ser
545                 550                 555                 560

Gly Glu Gly Arg Gly Ser Leu Leu Thr Cys Gly Asp Val Glu Glu Asn
                565                 570                 575

```
Pro Gly Pro Met Asp Thr Glu Ser Asn Arg Arg Ala Asn Leu Ala Leu
            580                 585                 590

Pro Gln Glu Pro Ser Ser Val Pro Ala Phe Glu Val Leu Glu Ile Ser
        595                 600                 605

Pro Gln Glu Val Ser Ser Gly Arg Leu Leu Lys Ser Ala Ser Ser Pro
    610                 615                 620

Pro Leu His Thr Trp Leu Thr Val Leu Lys Lys Gln Glu Phe Leu
625                 630                 635                 640

Gly Val Thr Gln Ile Leu Thr Ala Met Ile Cys Leu Cys Phe Gly Thr
                645                 650                 655

Val Val Cys Ser Val Leu Asp Ile Ser His Ile Glu Gly Asp Ile Phe
            660                 665                 670

Ser Ser Phe Lys Ala Gly Tyr Pro Phe Trp Gly Ala Ile Phe Phe Ser
        675                 680                 685

Ile Ser Gly Met Leu Ser Ile Ile Ser Glu Arg Arg Asn Ala Thr Tyr
    690                 695                 700

Leu Val Arg Gly Ser Leu Gly Ala Asn Thr Ala Ser Ser Ile Ala Gly
705                 710                 715                 720

Gly Thr Gly Ile Thr Ile Leu Ile Ile Asn Leu Lys Lys Ser Leu Ala
                725                 730                 735

Tyr Ile His Ile His Ser Cys Gln Lys Phe Phe Glu Thr Lys Cys Phe
            740                 745                 750

Met Ala Ser Phe Ser Thr Glu Ile Val Val Met Met Leu Phe Leu Thr
        755                 760                 765

Ile Leu Gly Leu Gly Ser Ala Val Ser Leu Thr Ile Cys Gly Ala Gly
    770                 775                 780

Glu Glu Leu Lys Gly Asn Lys Val Pro Glu Lys Arg Gly Arg Lys Lys
785                 790                 795                 800

Leu Leu Tyr Ile Phe Lys Gln Pro Phe Met Arg Pro Val Gln Thr Thr
                805                 810                 815

Gln Glu Glu Asp Gly Cys Ser Cys Arg Phe Pro Glu Glu Glu Glu Gly
            820                 825                 830

Gly Cys Glu Leu
        835

<210> SEQ ID NO 81
<211> LENGTH: 835
<212> TYPE: PRT
<213> ORGANISM: artificial sequence
<220> FEATURE:
<223> OTHER INFORMATION: anti- ROR1   H10 mcCAR

<400> SEQUENCE: 81

Met Ile Pro Ala Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Arg Val Lys
    50                  55                  60

Phe Ser Arg Ser Ala Asp Ala Pro Ala Tyr Gln Gln Gly Gln Asn Gln
65                  70                  75                  80

Leu Tyr Asn Glu Leu Asn Leu Gly Arg Arg Glu Glu Tyr Asp Val Leu
                85                  90                  95
```

-continued

```
Asp Lys Arg Arg Gly Arg Asp Pro Glu Met Gly Lys Pro Arg Arg
            100                 105                 110
Lys Asn Pro Gln Glu Gly Leu Tyr Asn Glu Leu Gln Lys Asp Lys Met
        115                 120                 125
Ala Glu Ala Tyr Ser Glu Ile Gly Met Lys Gly Glu Arg Arg Arg Gly
    130                 135                 140
Lys Gly His Asp Gly Leu Tyr Gln Gly Leu Ser Thr Ala Thr Lys Asp
145                 150                 155                 160
Thr Tyr Asp Ala Leu His Met Gln Ala Leu Pro Pro Arg Gly Ser Gly
                165                 170                 175
Ala Thr Asn Phe Ser Leu Leu Lys Gln Ala Gly Asp Val Glu Glu Asn
            180                 185                 190
Pro Gly Pro Met Ala Pro Ala Met Glu Ser Pro Thr Leu Leu Cys Val
        195                 200                 205
Ala Leu Leu Phe Phe Ala Pro Asp Gly Val Leu Ala Glu Val Lys Leu
    210                 215                 220
Val Glu Ser Gly Gly Gly Leu Val Lys Pro Gly Gly Ser Leu Lys Leu
225                 230                 235                 240
Ser Cys Ala Ala Ser Gly Phe Thr Phe Ser Ser Tyr Ala Met Ser Trp
                245                 250                 255
Val Arg Gln Thr Pro Glu Lys Arg Leu Glu Trp Val Ala Ser Ile Ser
            260                 265                 270
Thr Gly Ala Ser Ala Tyr Phe Pro Asp Ser Val Lys Gly Arg Phe Thr
        275                 280                 285
Ile Ser Arg Asp Asn Ala Arg Asn Ile Leu Tyr Leu Gln Met Ser Ser
    290                 295                 300
Leu Arg Ser Glu Asp Thr Ala Met Tyr Tyr Cys Ala Arg Ile Thr Thr
305                 310                 315                 320
Ser Thr Trp Tyr Phe Asp Val Trp Gly Ala Gly Thr Thr Val Thr Val
                325                 330                 335
Ser Ser Gly Gly Gly Gly Ser Gly Gly Gly Ser Gly Gly Gly Gly
            340                 345                 350
Ser Asp Ile Lys Met Thr Gln Ser Pro Ser Ser Met Tyr Ala Ser Leu
        355                 360                 365
Gly Glu Arg Val Thr Ile Thr Cys Lys Ala Ser Gln Asp Ile Asn Ser
    370                 375                 380
Tyr Leu Ser Trp Phe Gln Gln Lys Pro Gly Lys Ser Pro Lys Thr Leu
385                 390                 395                 400
Ile Tyr Arg Ala Asn Arg Leu Val Asp Gly Val Pro Ser Arg Phe Ser
                405                 410                 415
Gly Ser Gly Ser Gly Gln Asp Tyr Ser Leu Thr Ile Ser Ser Leu Glu
            420                 425                 430
Tyr Glu Asp Met Gly Ile Tyr Tyr Cys Leu Gln Tyr Asp Glu Phe Pro
        435                 440                 445
Tyr Thr Phe Gly Gly Gly Thr Lys Leu Glu Ile Lys Thr Thr Thr Pro
    450                 455                 460
Ala Pro Arg Pro Pro Thr Pro Ala Pro Thr Ile Ala Ser Gln Pro Leu
465                 470                 475                 480
Ser Leu Arg Pro Glu Ala Cys Arg Pro Ala Ala Gly Gly Ala Val His
                485                 490                 495
Thr Arg Gly Leu Asp Phe Ala Cys Asp Phe Phe Ile Pro Leu Leu Val
            500                 505                 510
Val Ile Leu Phe Ala Val Asp Thr Gly Leu Phe Ile Ser Thr Gln Gln
```

515                 520                 525
Gln Val Thr Phe Leu Leu Lys Ile Lys Arg Thr Arg Lys Gly Phe Arg
    530                 535                 540

Leu Leu Asn Pro His Pro Lys Pro Asn Pro Lys Asn Gly Ser Gly
545                 550                 555                 560

Glu Gly Arg Gly Ser Leu Leu Thr Cys Gly Asp Val Glu Glu Asn Pro
                565                 570                 575

Gly Pro Met Asp Thr Glu Ser Asn Arg Arg Ala Asn Leu Ala Leu Pro
            580                 585                 590

Gln Glu Pro Ser Ser Val Pro Ala Phe Glu Val Leu Glu Ile Ser Pro
        595                 600                 605

Gln Glu Val Ser Ser Gly Arg Leu Leu Lys Ser Ala Ser Ser Pro Pro
    610                 615                 620

Leu His Thr Trp Leu Thr Val Leu Lys Lys Glu Gln Glu Phe Leu Gly
625                 630                 635                 640

Val Thr Gln Ile Leu Thr Ala Met Ile Cys Leu Cys Phe Gly Thr Val
                645                 650                 655

Val Cys Ser Val Leu Asp Ile Ser His Ile Glu Gly Asp Ile Phe Ser
            660                 665                 670

Ser Phe Lys Ala Gly Tyr Pro Phe Trp Gly Ala Ile Phe Phe Ser Ile
        675                 680                 685

Ser Gly Met Leu Ser Ile Ile Ser Glu Arg Arg Asn Ala Thr Tyr Leu
    690                 695                 700

Val Arg Gly Ser Leu Gly Ala Asn Thr Ala Ser Ser Ile Ala Gly Gly
705                 710                 715                 720

Thr Gly Ile Thr Ile Leu Ile Ile Asn Leu Lys Lys Ser Leu Ala Tyr
                725                 730                 735

Ile His Ile His Ser Cys Gln Lys Phe Phe Glu Thr Lys Cys Phe Met
            740                 745                 750

Ala Ser Phe Ser Thr Glu Ile Val Val Met Met Leu Phe Leu Thr Ile
        755                 760                 765

Leu Gly Leu Gly Ser Ala Val Ser Leu Thr Ile Cys Gly Ala Gly Glu
    770                 775                 780

Glu Leu Lys Gly Asn Lys Val Pro Glu Lys Arg Gly Arg Lys Lys Leu
785                 790                 795                 800

Leu Tyr Ile Phe Lys Gln Pro Phe Met Arg Pro Val Gln Thr Thr Gln
                805                 810                 815

Glu Glu Asp Gly Cys Ser Cys Arg Phe Pro Glu Glu Glu Glu Gly Gly
            820                 825                 830

Cys Glu Leu
    835

<210> SEQ ID NO 82
<211> LENGTH: 831
<212> TYPE: PRT
<213> ORGANISM: artificial sequence
<220> FEATURE:
<223> OTHER INFORMATION: anti- ROR1  2A4  mcCAR

<400> SEQUENCE: 82

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile

-continued

```
                35                  40                  45
Gln Val Arg Lys Ala Ala Ile Thr Ser Tyr Glu Lys Ser Arg Val Lys
             50                  55                  60
Phe Ser Arg Ser Ala Asp Ala Pro Ala Tyr Gln Gln Gly Gln Asn Gln
 65                  70                  75                  80
Leu Tyr Asn Glu Leu Asn Leu Gly Arg Arg Glu Tyr Asp Val Leu
                 85                  90                  95
Asp Lys Arg Arg Gly Arg Asp Pro Glu Met Gly Gly Lys Pro Arg Arg
                100                 105                 110
Lys Asn Pro Gln Glu Gly Leu Tyr Asn Glu Leu Gln Lys Asp Lys Met
            115                 120                 125
Ala Glu Ala Tyr Ser Glu Ile Gly Met Lys Gly Glu Arg Arg Arg Gly
            130                 135                 140
Lys Gly His Asp Gly Leu Tyr Gln Gly Leu Ser Thr Ala Thr Lys Asp
145                 150                 155                 160
Thr Tyr Asp Ala Leu His Met Gln Ala Leu Pro Pro Arg Gly Ser Gly
                165                 170                 175
Ala Thr Asn Phe Ser Leu Leu Lys Gln Ala Gly Asp Val Glu Glu Asn
                180                 185                 190
Pro Gly Pro Met Ala Pro Ala Met Glu Ser Pro Thr Leu Leu Cys Val
            195                 200                 205
Ala Leu Leu Phe Phe Ala Pro Asp Gly Val Leu Ala Glu Val Lys Leu
            210                 215                 220
Gln Gln Ser Gly Pro Glu Leu Val Lys Pro Gly Ala Ser Val Lys Ile
225                 230                 235                 240
Ser Cys Lys Thr Ser Gly Tyr Thr Phe Thr Glu Tyr Thr Met His Trp
                245                 250                 255
Val Lys Gln Ser His Gly Lys Ser Leu Glu Trp Ile Gly Gly Ile Asn
                260                 265                 270
Pro Asn Asn Gly Gly Thr Ser Tyr Asn Gln Lys Phe Lys Gly Lys Ala
            275                 280                 285
Thr Leu Thr Val Asp Lys Ser Ser Thr Ala Tyr Met Glu Leu Arg
            290                 295                 300
Ser Leu Thr Ser Glu Asp Ser Ala Val Tyr Tyr Cys Ala Leu Gln Gly
305                 310                 315                 320
Phe Ala Tyr Trp Gly Gln Gly Thr Pro Leu Thr Val Ser Ser Gly Gly
                325                 330                 335
Gly Gly Ser Gly Gly Gly Gly Ser Gly Gly Gly Gly Ser Met Glu Ile
            340                 345                 350
Glu Ile Thr Gln Thr Pro Ala Leu Met Ser Ala Ser Pro Gly Glu Lys
            355                 360                 365
Val Thr Met Thr Cys Ser Ala Ser Ser Ser Val Ser Tyr Met Tyr Trp
            370                 375                 380
Tyr Gln Gln Lys Pro Arg Ser Ser Pro Lys Pro Trp Ile Tyr Leu Thr
385                 390                 395                 400
Ser Asn Leu Ala Ser Gly Val Pro Ala Arg Phe Ser Gly Ser Gly Ser
                405                 410                 415
Gly Thr Ser Tyr Ser Leu Thr Ile Ser Ser Met Glu Ala Glu Asp Ala
                420                 425                 430
Ala Thr Tyr Tyr Cys Gln Gln Trp Ser Ser Asn Pro Tyr Thr Phe Gly
            435                 440                 445
Gly Gly Thr Arg Leu Glu Leu Lys Thr Thr Thr Pro Ala Pro Arg Pro
450                 455                 460
```

Pro Thr Pro Ala Pro Thr Ile Ala Ser Gln Pro Leu Ser Leu Arg Pro
465                 470                 475                 480

Glu Ala Cys Arg Pro Ala Ala Gly Gly Ala Val His Thr Arg Gly Leu
            485                 490                 495

Asp Phe Ala Cys Asp Phe Phe Ile Pro Leu Leu Val Val Ile Leu Phe
        500                 505                 510

Ala Val Asp Thr Gly Leu Phe Ile Ser Thr Gln Gln Val Thr Phe
    515                 520                 525

Leu Leu Lys Ile Lys Arg Thr Arg Lys Gly Phe Arg Leu Leu Asn Pro
530                 535                 540

His Pro Lys Pro Asn Pro Lys Asn Asn Gly Ser Gly Glu Gly Arg Gly
545                 550                 555                 560

Ser Leu Leu Thr Cys Gly Asp Val Glu Glu Asn Pro Gly Pro Met Asp
                565                 570                 575

Thr Glu Ser Asn Arg Arg Ala Asn Leu Ala Leu Pro Gln Glu Pro Ser
                580                 585                 590

Ser Val Pro Ala Phe Glu Val Leu Glu Ile Ser Pro Gln Glu Val Ser
            595                 600                 605

Ser Gly Arg Leu Leu Lys Ser Ala Ser Ser Pro Pro Leu His Thr Trp
610                 615                 620

Leu Thr Val Leu Lys Lys Glu Gln Glu Phe Leu Gly Val Thr Gln Ile
625                 630                 635                 640

Leu Thr Ala Met Ile Cys Leu Cys Phe Gly Thr Val Val Cys Ser Val
                645                 650                 655

Leu Asp Ile Ser His Ile Glu Gly Asp Ile Phe Ser Ser Phe Lys Ala
                660                 665                 670

Gly Tyr Pro Phe Trp Gly Ala Ile Phe Phe Ser Ile Ser Gly Met Leu
            675                 680                 685

Ser Ile Ile Ser Glu Arg Arg Asn Ala Thr Tyr Leu Val Arg Gly Ser
690                 695                 700

Leu Gly Ala Asn Thr Ala Ser Ser Ile Ala Gly Gly Thr Gly Ile Thr
705                 710                 715                 720

Ile Leu Ile Ile Asn Leu Lys Lys Ser Leu Ala Tyr Ile His Ile His
                725                 730                 735

Ser Cys Gln Lys Phe Phe Glu Thr Lys Cys Phe Met Ala Ser Phe Ser
                740                 745                 750

Thr Glu Ile Val Val Met Met Leu Phe Leu Thr Ile Leu Gly Leu Gly
            755                 760                 765

Ser Ala Val Ser Leu Thr Ile Cys Gly Ala Gly Glu Glu Leu Lys Gly
            770                 775                 780

Asn Lys Val Pro Glu Lys Arg Gly Arg Lys Lys Leu Leu Tyr Ile Phe
785                 790                 795                 800

Lys Gln Pro Phe Met Arg Pro Val Gln Thr Thr Gln Glu Glu Asp Gly
                805                 810                 815

Cys Ser Cys Arg Phe Pro Glu Glu Glu Glu Gly Gly Cys Glu Leu
            820                 825                 830

<210> SEQ ID NO 83
<211> LENGTH: 837
<212> TYPE: PRT
<213> ORGANISM: artificial sequence
<220> FEATURE:
<223> OTHER INFORMATION: anti- ROR1   1C11   mcCAR

<400> SEQUENCE: 83

```
Met Ile Pro Ala Val Leu Leu Leu Leu Val Glu Gln Ala
 1               5              10              15

Ala Ala Leu Gly Glu Pro Gln Leu Cys Tyr Ile Leu Asp Ala Ile Leu
            20              25              30

Phe Leu Tyr Gly Ile Val Leu Thr Leu Leu Tyr Cys Arg Leu Lys Ile
            35              40              45

Gln Val Arg Lys Ala Ala Ile Thr Ser Tyr Glu Lys Ser Arg Val Lys
 50              55                      60

Phe Ser Arg Ser Ala Asp Ala Pro Ala Tyr Gln Gln Gly Gln Asn Gln
 65              70              75              80

Leu Tyr Asn Glu Leu Asn Leu Gly Arg Arg Glu Glu Tyr Asp Val Leu
            85              90              95

Asp Lys Arg Arg Gly Arg Asp Pro Glu Met Gly Gly Lys Pro Arg Arg
            100             105             110

Lys Asn Pro Gln Glu Gly Leu Tyr Asn Glu Leu Gln Lys Asp Lys Met
            115             120             125

Ala Glu Ala Tyr Ser Glu Ile Gly Met Lys Gly Glu Arg Arg Arg Gly
            130             135             140

Lys Gly His Asp Gly Leu Tyr Gln Gly Leu Ser Thr Ala Thr Lys Asp
145             150             155             160

Thr Tyr Asp Ala Leu His Met Gln Ala Leu Pro Pro Arg Gly Ser Gly
            165             170             175

Ala Thr Asn Phe Ser Leu Leu Lys Gln Ala Gly Asp Val Glu Glu Asn
            180             185             190

Pro Gly Pro Met Ala Pro Ala Met Glu Ser Pro Thr Leu Leu Cys Val
            195             200             205

Ala Leu Leu Phe Phe Ala Pro Asp Gly Val Leu Ala Glu Val Lys Leu
            210             215             220

Gln Glu Ser Gly Ala Glu Leu Ala Arg Pro Gly Ala Ser Val Lys Met
225             230             235             240

Ser Cys Lys Ala Ser Gly Tyr Thr Phe Thr Ser Tyr Thr Met His Trp
            245             250             255

Val Lys Gln Arg Pro Gly Gln Gly Leu Glu Trp Ile Gly Tyr Ile Asn
            260             265             270

Pro Ser Ser Gly Tyr Thr Glu Tyr Asn Gln Lys Phe Lys Asp Lys Thr
            275             280             285

Thr Leu Thr Ala Asp Lys Ser Ser Thr Ala Tyr Met Gln Leu Ser
            290             295             300

Ser Leu Thr Ser Gly Asp Ser Ala Val Tyr Tyr Cys Ala Arg Arg Val
305             310             315             320

Leu Trp Leu Arg Arg Gly Asp Tyr Trp Gly Gln Gly Thr Ile Leu Thr
            325             330             335

Val Ser Ala Gly Gly Gly Gly Ser Gly Gly Gly Ser Gly Gly Gly
            340             345             350

Gly Ser Met Glu Val Leu Ile Thr Gln Thr Pro Ser Ser Leu Ser Ala
            355             360             365

Ser Leu Gly Glu Arg Val Ser Leu Thr Cys Arg Ala Ser Gln Asp Ile
            370             375             380

Gly Ser Ser Leu Asn Trp Leu Gln Gln Glu Pro Asp Gly Thr Ile Lys
385             390             395             400

Arg Leu Ile Tyr Ala Thr Ser Ser Leu Asp Ser Gly Val Pro Lys Arg
            405             410             415
```

```
Phe Ser Gly Ser Arg Ser Gly Ser Asp Tyr Ser Leu Thr Ile Ser Ser
                420                 425                 430

Leu Glu Ser Glu Asp Phe Val Asp Tyr Tyr Cys Leu Gln Tyr Ala Ser
            435                 440                 445

Ser Pro Tyr Thr Phe Gly Gly Gly Thr Lys Leu Glu Leu Lys Thr Thr
        450                 455                 460

Thr Pro Ala Pro Arg Pro Pro Thr Pro Ala Pro Thr Ile Ala Ser Gln
465                 470                 475                 480

Pro Leu Ser Leu Arg Pro Glu Ala Cys Arg Pro Ala Ala Gly Gly Ala
                485                 490                 495

Val His Thr Arg Gly Leu Asp Phe Ala Cys Asp Phe Phe Ile Pro Leu
            500                 505                 510

Leu Val Val Ile Leu Phe Ala Val Asp Thr Gly Leu Phe Ile Ser Thr
        515                 520                 525

Gln Gln Gln Val Thr Phe Leu Leu Lys Ile Lys Arg Thr Arg Lys Gly
530                 535                 540

Phe Arg Leu Leu Asn Pro His Pro Lys Pro Asn Pro Lys Asn Asn Gly
545                 550                 555                 560

Ser Gly Glu Gly Arg Gly Ser Leu Leu Thr Cys Gly Asp Val Glu Glu
                565                 570                 575

Asn Pro Gly Pro Met Asp Thr Glu Ser Asn Arg Arg Ala Asn Leu Ala
            580                 585                 590

Leu Pro Gln Glu Pro Ser Ser Val Pro Ala Phe Glu Val Leu Glu Ile
        595                 600                 605

Ser Pro Gln Glu Val Ser Ser Gly Arg Leu Leu Lys Ser Ala Ser Ser
610                 615                 620

Pro Pro Leu His Thr Trp Leu Thr Val Leu Lys Lys Glu Gln Glu Phe
625                 630                 635                 640

Leu Gly Val Thr Gln Ile Leu Thr Ala Met Ile Cys Leu Cys Phe Gly
                645                 650                 655

Thr Val Val Cys Ser Val Leu Asp Ile Ser His Ile Glu Gly Asp Ile
            660                 665                 670

Phe Ser Ser Phe Lys Ala Gly Tyr Pro Phe Trp Gly Ala Ile Phe Phe
        675                 680                 685

Ser Ile Ser Gly Met Leu Ser Ile Ile Ser Glu Arg Arg Asn Ala Thr
690                 695                 700

Tyr Leu Val Arg Gly Ser Leu Gly Ala Asn Thr Ala Ser Ser Ile Ala
705                 710                 715                 720

Gly Gly Thr Gly Ile Thr Ile Leu Ile Ile Asn Leu Lys Lys Ser Leu
                725                 730                 735

Ala Tyr Ile His Ile His Ser Cys Gln Lys Phe Phe Glu Thr Lys Cys
            740                 745                 750

Phe Met Ala Ser Phe Ser Thr Glu Ile Val Val Met Met Leu Phe Leu
        755                 760                 765

Thr Ile Leu Gly Leu Gly Ser Ala Val Ser Leu Thr Ile Cys Gly Ala
770                 775                 780

Gly Glu Glu Leu Lys Gly Asn Lys Val Pro Glu Lys Arg Gly Arg Lys
785                 790                 795                 800

Lys Leu Leu Tyr Ile Phe Lys Gln Pro Phe Met Arg Pro Val Gln Thr
                805                 810                 815

Thr Gln Glu Glu Asp Gly Cys Ser Cys Arg Phe Pro Glu Glu Glu Glu
            820                 825                 830

Gly Gly Cys Glu Leu
```

<210> SEQ ID NO 84
<211> LENGTH: 49
<212> TYPE: DNA
<213> ORGANISM: homo sapiens
<220> FEATURE:
<223> OTHER INFORMATION: TRAC T01 target sequence

<400> SEQUENCE: 84
ttgtcccaca gatatccaga accctgaccc tgccgtgtac cagctgaga                49

<210> SEQ ID NO 85
<211> LENGTH: 530
<212> TYPE: PRT
<213> ORGANISM: artificial sequence
<220> FEATURE:
<223> OTHER INFORMATION: TAL binding domain  TRAC_T01-L

<400> SEQUENCE: 85

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala

```
            290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
                340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Val Ala Ile Ala
        370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Gln Gln Val
            435                 440                 445

Val Ala Ile Ala Ser Asn Gly Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Arg Pro Ala
            515                 520                 525

Leu Glu
    530

<210> SEQ ID NO 86
<211> LENGTH: 530
<212> TYPE: PRT
<213> ORGANISM: artificial sequence
<220> FEATURE:
<223> OTHER INFORMATION: TAL binding domain TRAC_T01-R

<400> SEQUENCE: 86

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser Asn Ile Gly Gly Lys Gln Ala Leu Glu Thr Val Gln Ala Leu Leu
```

```
            115                 120                 125
Pro Val Leu Cys Gln Ala His Gly Leu Thr Pro Gln Gln Val Val Ala
        130                 135                 140
Ile Ala Ser Asn Asn Gly Gly Lys Gln Ala Leu Glu Thr Val Gln Arg
145                 150                 155                 160
Leu Leu Pro Val Leu Cys Gln Ala His Gly Leu Thr Pro Glu Gln Val
                165                 170                 175
Val Ala Ile Ala Ser His Asp Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Gly Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
Leu Thr Pro Gln Gln Val Val Ala Ile Ala Ser Asn Asn Gly Gly Lys
        275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Glu Gln Val Val Ala Ile Ala
    370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530
```

<210> SEQ ID NO 87
<211> LENGTH: 2814
<212> TYPE: DNA
<213> ORGANISM: artificial sequence
<220> FEATURE:
<223> OTHER INFORMATION: polynucleotide encoding TRAC_T01-L TALEN

<400> SEQUENCE: 87

| | | | | | | |
|---|---|---|---|---|---|---|
| atgggcgatc | ctaaaaagaa | acgtaaggtc | atcgattacc | catacgatgt | tccagattac | 60 |
| gctatcgata | tcgccgatct | acgcacgctc | ggctacagcc | agcagcaaca | ggagaagatc | 120 |
| aaaccgaagg | ttcgttcgac | agtggcgcag | caccacgagg | cactggtcgg | ccacgggttt | 180 |
| acacacgcgc | acatcgttgc | gttaagccaa | cacccggcag | cgttagggac | cgtcgctgtc | 240 |
| aagtatcagg | acatgatcgc | agcgttgcca | gaggcgacac | acgaagcgat | cgttggcgtc | 300 |
| ggcaaacagt | ggtccggcgc | acgcgctctg | gaggccttgc | tcacggtggc | gggagagttg | 360 |
| agaggtccac | cgttacagtt | ggacacaggc | caacttctca | agattgcaaa | acgtggcggc | 420 |
| gtgaccgcag | tggaggcagt | gcatgcatgg | cgcaatgcac | tgacgggtgc | cccgctcaac | 480 |
| ttgacccccc | agcaggtggt | ggccatcgcc | agcaatggcg | gtggcaagca | ggcgctggag | 540 |
| acggtccagc | ggctgttgcc | ggtgctgtgc | caggcccacg | gcttgacccc | ccagcaggtg | 600 |
| gtggccatcg | ccagcaataa | tggtggcaag | caggcgctgg | agacggtcca | gcggctgttg | 660 |
| ccggtgctgt | gccaggccca | cggcttgacc | cccagcagg | tggtggccat | cgccagcaat | 720 |
| ggcggtggca | agcaggcgct | ggagacggtc | agcggctgt | tgccggtgct | gtgccaggcc | 780 |
| cacggcttga | ccccggagca | ggtggtggcc | atcgccagcc | acgatggcgg | caagcaggcg | 840 |
| ctggagacgg | tccagcggct | gttgccggtc | tgtgccagg | cccacggctt | gaccccggag | 900 |
| caggtggtgg | ccatcgccag | ccacgatggc | ggcaagcagg | cgctggagac | ggtccagcgg | 960 |
| ctgttgccgg | tgctgtgcca | ggcccacggc | ttgaccccgg | agcaggtggt | ggccatcgcc | 1020 |
| agccacgatg | gcggcaagca | ggcgctggag | acggtccagc | ggctgttgcc | ggtgctgtgc | 1080 |
| caggcccacg | gcttgacccc | ggagcaggtg | gtggccatcg | ccagcaatat | tggtggcaag | 1140 |
| caggcgctgg | agacggtgca | ggcgctgttg | ccggtgctgt | gccaggccca | cggcttgacc | 1200 |
| ccggagcagg | tggtggccat | cgccagccac | gatggcggca | agcaggcgct | ggagacggtc | 1260 |
| cagcggctgt | tgccggtgct | gtgccaggcc | cacggcttga | ccccggagca | ggtggtggcc | 1320 |
| atcgccagca | atattggtgg | caagcaggcg | ctggagacgg | tgcaggcgct | gttgccggtg | 1380 |
| ctgtgccagg | cccacggctt | gaccccccag | caggtggtgg | ccatcgccag | caataatggt | 1440 |
| ggcaagcagg | cgctggagac | ggtccagcgg | ctgttgccgg | tgctgtgcca | ggcccacggc | 1500 |
| ttgaccccgg | agcaggtggt | ggccatcgcc | agcaatattg | gtggcaagca | ggcgctggag | 1560 |
| acggtgcagg | cgctgttgcc | ggtgctgtgc | caggcccacg | gcttgacccc | ccagcaggtg | 1620 |
| gtggccatcg | ccagcaatgg | cggtggcaag | caggcgctgg | agacggtcca | gcggctgttg | 1680 |
| ccggtgctgt | gccaggccca | cggcttgacc | ccggagcagg | tggtggccat | cgccagcaat | 1740 |
| attggtggca | agcaggcgct | ggagacggtc | agcggctgt | tgccggtgct | gtgccaggcc | 1800 |
| cacggcttga | ccccccagca | ggtggtggcc | atcgccagca | atggcggtgg | caagcaggcg | 1860 |
| ctggagacgg | tccagcggct | gttgccggtg | ctgtgccagg | cccacggctt | gaccccggag | 1920 |
| caggtggtgg | ccatcgccag | ccacgatggc | ggcaagcagg | cgctggagac | ggtccagcgg | 1980 |
| ctgttgccgg | tgctgtgcca | ggcccacggc | ttgacccctc | agcaggtggt | ggccatcgcc | 2040 |

| | |
|---|---:|
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca cccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgaggg ggaagttcaa caacggcgag atcaacttcg cggccgactg ataa | 2814 |

<210> SEQ ID NO 88
<211> LENGTH: 2832
<212> TYPE: DNA
<213> ORGANISM: artificial sequence
<220> FEATURE:
<223> OTHER INFORMATION: polynucleotide encoding TRAC_T01-R TALEN

<400> SEQUENCE: 88

| | |
|---|---:|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccc tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccgag caggtggtgg ccatcgccag ccacgatggc | 540 |
| ggcaagcagg cgctggagac ggtccagcgg ctgttgccgg tgctgtgcca ggcccacggc | 600 |
| ttgacccccc agcaggtggt ggccatcgcc agcaatggcg gtggcaagca ggcgctggag | 660 |
| acggtccagc ggctgttgcc ggtgctgtgc caggcccacg gcttgacccc ggagcaggtg | 720 |
| gtggccatcg ccagccacga tggcggcaag caggcgctgg agacggtcca gcggctgttg | 780 |
| ccggtgctgt gccaggccca cggcttgacc ccggagcagg tggtggccat cgccagcaat | 840 |
| attggtggca agcaggcgct ggagacggtc aggcgctgt tgccggtgct gtgccaggcc | 900 |
| cacggcttga ccccccagca ggtggtggcc atcgccagca taatggtgg caagcaggcg | 960 |
| ctggagacgg tccagcggct gttgccggtg ctgtgccagg cccacggctt gaccccggag | 1020 |
| caggtggtgg ccatcgccag ccacgatggc ggcaagcagg cgctggagac ggtccagcgg | 1080 |
| ctgttgccgg tgctgtgcca ggcccacggc ttgaccccc agcaggtggt ggccatcgcc | 1140 |
| agcaatggcg gtggcaagca ggcgctggag acggtccagc ggctgttgcc ggtgctgtgc | 1200 |
| caggcccacg gcttgacccc cagcaggtg gtggccatcg ccagcaataa tggtggcaag | 1260 |
| caggcgctgg agacggtcca gcggctgttg ccggtgctgt gccaggccca cggcttgacc | 1320 |

-continued

```
cccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg cggcaagca ggcgctggag    1680 acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860 gatgcggca agcaggcgct ggagacggtc agcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gaccccctcag    2040 caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga aatccgagtt gaggcacaag    2280
ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca cggcgagat caacttcgcg    2820 gccgactgat aa                                                       2832
```

ROR1 SPECIFIC MULTI-CHAIN CHIMERIC ANTIGEN RECEPTOR

CROSS REFERENCE TO RELATED APPLICATION

This application is a 35 U.S.C. § 371 National Phase of PCT Application No. PCT/EP2015/067441 filed Jul. 29, 2015, which claims priority to Danish Patent Application No. PA201470469 filed Jul. 31, 2014. The disclosure of these prior applications are hereby incorporated in their entirety by reference.

FIELD OF THE INVENTION

The present invention relates to a new generation of chimeric antigen receptors (CAR) referred to as multi-chain CARs, which are made specific to the antigen ROR1. Such CARs aim to redirect immune cell specificity and reactivity toward malignant cells expressing the tumor antigen ROR1. The alpha, beta and gamma polypeptides composing these CARs are designed to assemble in juxtamembrane position, which forms flexible architecture closer to natural receptors, that confers optimal signal transduction. The invention encompasses the polynucleotides, vectors encoding said multi-chain CAR and the isolated cells expressing them at their surface, in particularly for their use in immunotherapy. The invention opens the way to efficient adoptive immunotherapy strategies for treating cancer, especially chronic lymphocytic leukemia (CLL) or solid tumors such as breast, colon, lung, and kidney tumors.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. (2011) Treating Cancer with Genetically Engineered T Cells. *Trends Biotechnol.* 29(11): 550-557) Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. (2010) Redirecting T-cell specificity by introducing a tumor-specific chimeric antigen receptor. Blood. 116(7): 1035-1044). CARs are synthetic receptors consisting of a targeting moiety that is associated with one or more signaling domains to form a single-chain fusion molecule. However, this approach has so far proven efficiency only with respect to patients with acute lymphoblastic leukemia (ALL) by targeting malignant B cells bearing the antigen CD19 (Porter, D. L. et al. (2011) Chimeric Antigen Receptor—Modified T Cells in Chronic Lymphoid Leukemia. N. Engl. J. Med. 365:725-733). Chronic lymphocytic leukemia (CLL) is one of the most commonly diagnosed leukemias managed by practicing hematologists. For many years patients with CLL have been viewed as similar, with a long natural history and only marginally effective therapies that rarely yielded complete responses. Recently, several important observations related to the biologic significance of $V_H$ mutational status and associated ZAP-70 overexpression, disrupted p53 function, and chromosomal aberrations have led to the ability to identify patients at high risk for early disease progression and inferior survival. Concurrent with these investigations, several treatments including the nucleoside analogues, monoclonal antibodies rituximab and alemtuzumab have been introduced. Combination of these therapies in clinical trials has led to high complete and overall response rates when applied as initial therapy for symptomatic CLL. Thus, the complexity of initial risk stratification of CLL and treatment has increased significantly. Furthermore, when these initial therapies do not work, approach of the CLL patient with fludarabine-refractory disease can be quite challenging (Byrd J. C et al, 2014).

One candidate antigen of immunotherapies for chronic lymphocytic leukemia (CLL) is Tyrosine-protein kinase transmembrane receptor ROR1 (also called NTRKR1; UniProtKB/TrEMBL) entries: Q01973). ROR1 (The receptor tyrosine kinase-like orphan receptor 1) is a 120-kDa glycoprotein containing an extracellular immunoglobulin (Ig)-like, Kringle, and Frizzled-like cysteine rich domain (FIG. 1). The protein encoded by this gene is a receptor tyrosine kinase that modulates neurite growth in the central nervous system. It is a type I membrane protein and belongs to the ROR subfamily of cell surface receptors (Reddy et al, 1997). The Ror1 protein expression in patients with CLL but not in normal leukocytes merits further studies of its role in the pathobiology of CLL, which may provide a basis for development of Ror1 directed targeted therapy (Daneshmanesh et al; 2008). ROR1 is expressed on a variety of B-cell malignancies, and subsets of some solid tumors, including breast, colon, lung, and kidney tumors. ROR1 functions in oncogenic signaling to promote tumor cell survival in epithelial tumors. Importantly, ROR1 is not expressed on vital organs, except adipose and pancreatic tissue, which reduces potential toxicities from killing of normal cells (Hudecek et al, 2013). ROR1 is expressed during embryogenesis but absent from normal adult tissues, apart from a subset of immature B-cell precursors, and low-level expression on adipocytes (Hudecek et al., 2010; Matsuda et al., 2001). ROR1 was first shown to be expressed in B-cell chronic lymphocytic leukemia (B-CLL) by transcriptional profiling (Klein et al., 2001; Rosenwald et al., 2001) and was subsequently identified on the surface of many cancers including mantle cell lymphoma (MCL), acute lymphoblastic leukemia (ALL) with a t(1;19) chromosome translocation, and a subset of lung, breast, colon, pancreas, renal, and ovarian cancers (Baskar et al., 2008; Bicocca et al., 2012; Daneshmanesh et al., 2008; Dave et al., 2012; Fukuda et al., 2008; Yamaguchi et al., 2012; Zhang et al., 2012a, 2012b). In both lung adenocarcinoma and t(1;19) ALL, ROR1 cooperates in oncogenic signaling and knockdown of ROR1 with siRNA exposed a critical role for this molecule in maintaining tumor cell survival (Bicocca et al., 2012; Choudhury et al., 2010; Gentile et al., 2011; Yamaguchi et al., 2012). Thus, ROR1 loss may not be readily tolerated by tumors making it an attractive candidate for CAR directed T-cell therapy that could be broadly applied. It thus represents an appropriate target antigen for treating CLL or solid tumors, especially using CAR-expressing T cells.

The laboratories of Dr. Stanley Riddell and Dr. Laurence Cooper have previously engineered and validated anti-ROR1 scCARs containing the 4A5 and the 2A2 scFvs, respectively (Cooper et al 2010; Hudecek et al., 2013). In particular, Hudecek et al discloses anti-ROR1 scCARs which contain an IgG4 hinge of diverse length and a CD28 transmembrane domain.

There is still the need for the improvement of CAR functionality by designing CAR architecture and using suitable components since these parameters play a role important and a fine tuning is necessary.

In the context of developing therapeutic grade engineered immune cells that can target malignant or infected cells, the inventors have sought for improved CAR architectures, which would be closer to natural ones and likely to behave accordingly using any extracellular mono or multi-specific ligand binding domains. In WO2014039523, they described a new generation of CARs involving separate polypeptide sub-units according to the present invention, referred to as "multi-chain CARs". According to this architecture, the signaling domains and co-stimulatory domains are located on different polypeptide chains (FIG. 2). Such multi-chain CARs can be derived from FcɛRI, by replacing the high affinity IgE binding domain of FcɛRI alpha chain by an extracellular ligand-binding domain such as scFv, whereas the N and/or C-termini tails of FcɛRI beta and/or gamma chains are fused to signal transducing domains and co-stimulatory domains respectively. The extracellular ligand binding domain has the role of redirecting T-cell specificity towards cell targets, while the signal transducing domains activate the immune cell response. The fact that the different polypeptides derived from the alpha, beta and gamma polypeptides from FcɛRI are transmembrane polypeptides sitting in juxtamembrane position, provides a more flexible architecture to CARs and reduces background activation of immune cells. However, this flexibility provides more variability from one binding sequence to another, so that it is difficult to predict which binding domain and optimal architecture provide with an appropriate specificity towards ROR1.

It can be noted that single and multichain CAR architectures bearing the same scFvs may not perform the same way, depending of parameters which are not always controlled by the skilled man of the art. This remark may apply also to the type of expression used (transient or stable by using respectively, for instance, mRNA or lentivirus delivery).

Another aspect to be considered is the potential adverse effects linked to the infusion of engineered T cells to the patient, and in particular the cytokine-release syndrome (CRS). Thus, there is the need for designing the right CAR architecture and their specific components which can reduce the occurrence of such adverse events.

The invention provides with optimally designed multi-chain CAR bearing scFv extracellular domain, which are particularly suited to target malignant cells bearing ROR1 as a surface protein. It has been shown in the present invention that a particular architecture of multichain CAR with well-defined components can allow the engineered immune cells to be cytotoxic towards ROR1 antigen-bearing tumor cells. From those mcCARs, 2 of them csm13 and csm14 appear to be performant in terms of specific lysis while the immune cells keep their innate function.

This achievement opens the way to new immunotherapy treatments of malignant cells diagnosed to be ROR1 positive, such as those found in CLL and solid tumors in particular breast, colon, lung, and kidney tumors.

SUMMARY OF THE INVENTION

The inventors have generated ROR1 specific multichain CARs different scFV derived from ROR1 specific antibodies.

Following non-specific activation in vitro (e.g. with anti CD3/CD28 coated beads and recombinant IL2), T-cells from donors have been transformed with polynucleotides expressing these CARs using viral transduction. In certain instances, the T-cells may be further engineered to create non-alloreactive T-cells, more especially by disruption of a component of TCR ($\alpha\beta$-T-Cell receptors) to prevent Graft versus host reaction. The resulting engineered T-cells displayed reactivity in-vitro against ROR1 positive cells to various extend, showing that the CARs of the present invention contribute to antigen dependent activation, proliferation of the T-cells, and also could be cytotoxic towards cells expressing ROR1, making them useful for immunotherapy.

The polypeptides and polynucleotide sequences encoding the CARs of the present invention are detailed in the present specification. Two anti-ROR1 multi-chain CARs (mcCARs)-csm13 and csm14-bearing scFvs from D10 and 2A2 monoclonal antibodies respectively, have shown remarkably their highly expression on the cell surface which could remain over a 2-weeks period. Moreover, csm13 and csm14 have shown their cytotoxic effect towards ROR1-expressing cells, while retaining their innate function.

The engineered immune cells of the present invention are particularly useful for treating haematological cancer conditions or for treating solid tumor.

Figure 1:
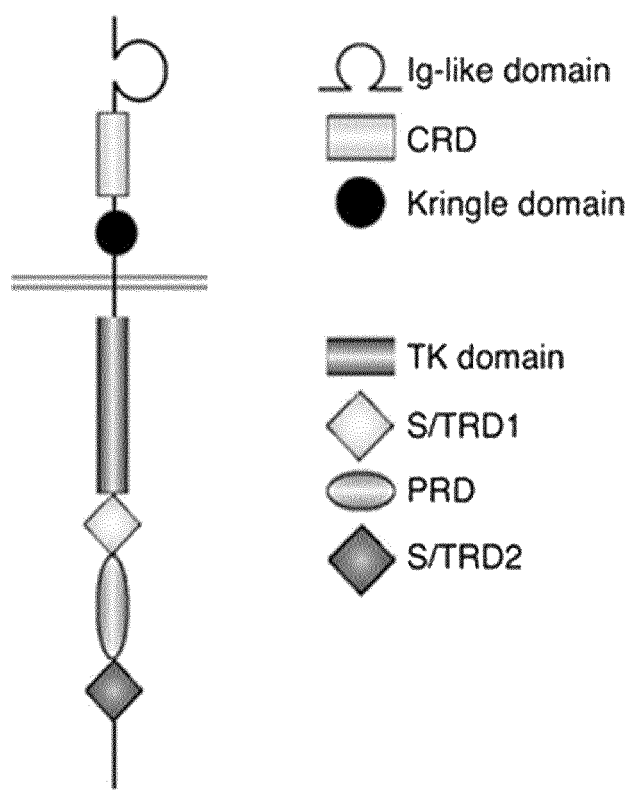
FIG. 1: Structure of the ROR1 protein with its ecto- and endo-domain parts. Type 1 receptor tyrosine kinase evolutionarily conserved, co-receptor with Frizzled-2/4, with immunoglobulin (Ig) domain, cysteine-rich domain (CRD), and Kringle domain. The intracellular portion contains tyrosine kinase (TK) domain, proline-rich domain (PRD) flanked by Ser/Thr rich domains (S/TRD1 and 2.
Figure 2:
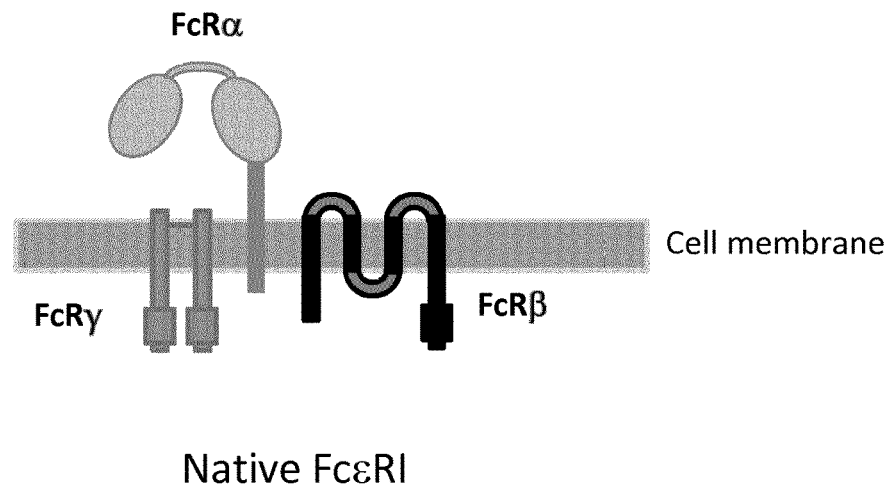
FIG. 2: Schematic representation of FcɛRI from which derivate the multi-chain CAR architecture according to the invention. FcɛRI is composed of 3 transmembrane chains $\alpha$, $\beta$ and $\gamma$.

The following Tables 1 to 6 show the components and their sequences which are used to assemble the multi-chain CARs of the present invention, as well as their architectures (assembly). Table 7 shows the polypeptide sequences of ROR1 multi-chain CARs.

TABLE 1

Exemplary sequences of the alpha polypeptide component of ROR1 muti-chain CAR

| Functional domains | description | SEQ ID # | Raw amino acid sequence |
|---|---|---|---|
| FcεRI-SP | signal peptide | SEQ ID NO. 1 | MAPAMESPTLLCVALLFFAPDGVLA |
| CD8αhinge | hinge | SEQ ID NO. 2 | TTTPAPRPPTPAPTIASQPLSLRPEACRPAAGGAVHTRGLDFACD |
| VH | | | See Table 5 |
| G4SX3Linker | Linker VH-VL | SEQ ID NO. 3 | GGGGSGGGGSGGGGS |
| VL | | | See Table 5 |
| FcεRI α-TM-IC | Fc Receptor for IgE, alpha chain, transmembrane and intracellular domain | SEQ ID NO. 4 | FFIPLLVVILFAVDTGLFISTQQQVTFLLKIKRTRKGFRLLNPHPKPNPKNN |

TABLE 2

Exemplary sequences of the beta polypeptide component of ROR1 muti-chain CAR

| Functional domains | description | SEQ ID # | Raw amino acid sequence |
|---|---|---|---|
| FcεR1β-ΔITAM | Fc Receptor for IgE, beta chain, without ITAM | SEQ ID NO. 5 | MDTESNRRANLALPQEPSSVPAFEVLEISPQEVSSGRLLKSASSPPLHTWLTVLKKEQEFLGVTQILTAMICLCFGTVVCSVLDISHIEGDIFSSFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNKVPE |
| 41BB-IC | 41BB co-stimulatory domain | SEQ ID NO. 6 | KRGRKKLLYIFKQPFMRPVQTTQEEDGCSCRFPEEEEGGCEL |

TABLE 3

Exemplary sequences of the gamma polypeptide component of ROR1 muti-chain CAR

| Functional domains | description | SEQ ID # | Raw amino acid sequence |
|---|---|---|---|
| FcεRI γ-SP | signal peptide | SEQ ID NO. 7 | MIPAVVLLLLLLVEQAAA |
| FcεRI γ-ΔITAM | Fc Receptor for IgE, gamma chain, without ITAM | SEQ ID NO. 8 | LGEPQLCYILDAILFLYGIVLTLLYCRLKIQVRKAAITSYEKSRVKFSRSADAPAYQQGQNQLYN |
| CDζ0C | CD3zeta intracellular domain comprising ITAM | SEQ ID NO. 9 | ELNLGRREEYDVLDKRRGRDPEMGGKPRRKNPQEGLYNELQKDKMAEAYSEIGMKGERRRGKGHDGLYQGLSTATKDTYDALHMQALPPR |

TABLE 4 skip peptides linking the polypeptides forming the mutli-subunit CAR

| Functional domains | description | SEQ ID # | Raw amino acid sequence |
|---|---|---|---|
| GSG-P2A | GSG-P2A ribosomal skip peptide | SEQ ID NO. 10 | GSGATNFSLLKQAGDVEENPGP |
| GSG-T2A | GSG-T2 ribosomal skip peptide | SEQ ID NO. 11 | GSGEGRGSLLTCGDVEENPGP |

TABLE 5

Sequence of the 8 pairs of anti-ROR1 scFvs from murine origin, their CDRs of the scFv

| ScFv sequences | SEQ ID # | Raw amino acid sequence |
|---|---|---|
| MURINE ORIGIN | | |
| 2A2 heavy chain variable region | SEQ ID NO. 12 | QVQLQQSGAELVRPGASVTLSCKASGYTFSDYEMHWVIQTPVHGLEWI GAIDPETGGTAYNQKFKGKAILTADKSSSTAYMELRSLTSEDSAVYYCTGY YDYDSFTYWGQGTLVTVSA |
| | SEQ ID NO. 13 | CDR1: GYTFSDYE |
| | SEQ ID NO. 14 | CDR2: IDPETGGT |
| | SEQ ID NO. 15 | CDR3: TGYYDYDSFTY |
| 2A2 light chain variable region | SEQ ID NO. 16 | DIVMTQSQKIMSTTVGDRVSITCKASQNVDAAVAWYQQKPGQSPKLLI YSASNRYTGVPDRFTGSGSGTDFTLTISNMQSEDLADYFCQQYDIYPYTF GGGTKLEIK |
| | SEQ ID NO. 17 | CDR1: QNVDAA |
| | SEQ ID NO. 18 | CDR2: SAS |
| | SEQ ID NO. 19 | CDR3: QQYDIYPYT |
| 4A5 heavy chain variable region | SEQ ID NO. 20 | EVKLVESGGGLVKPGGSLKLSCAASGFTFSSYAMSWVRQIPEKRLEWVA SISRGGTTYYPDSVKGRFTISRDNVRNILYLQMSSLRSEDTAMYYCGRYD YDGYYAMDYWGQGTSVTVSS |
| | SEQ ID NO. 21 | CDR1: GFTFSSYA |
| | SEQ ID NO. 22 | CDR2: ISRGGTT |
| | SEQ ID NO. 23 | CDR3: GRYDYDGYYAMDY |
| 4A5 light chain variable region | SEQ ID NO. 24 | DIKMTQSPSSMYASLGERVTITCKASPDINSYLSWFQQKPGKSPKTLIYRA NRLVDGVPSRFSGGGSGQDYSLTINSLEYEDMGIYYCLQYDEFPYTFGGG TKLEMK |
| | SEQ ID NO. 25 | CDR1: PDINSY |
| | SEQ ID NO. 26 | CDR2: RAN |
| | SEQ ID NO. 27 | CDR3: LQYDEFPYT |
| D10 heavy chain variable region | SEQ ID NO. 28 | QVQLKESGPGLVAPSQTLSITCTVSGFSLTSYGVHWVRQPPGKGLEWLG VIWAGGFTNYNSALKSRLSISKDNSKSQVLLKMTSLQTDDTAMYYCARR GSSYSMDYWGQGTSVTVSS |
| | SEQ ID NO. 29 | CDR-H1: GFSLTSYG |
| | SEQ ID NO. 30 | CDR-H2: IWAGGFT |
| | SEQ ID NO. 31 | CDR-H3: ARRGSSYSMDY |
| D10 light chain variable region | SEQ ID NO. 32 | EIVLSQSPAITAASLGQKVTITCSASSNVSYIHWYQQRSGTSPRPWIYEISK LASGVPVRFSGSGSGTSYSLTISSMEAEDAAIYYCQQWNYPLITFGSGTKL EIQ |
| | SEQ ID NO. 33 | CDR-L1: SNVSY |
| | SEQ ID NO. 34 | CDR-L2: EIS |
| | SEQ ID NO. 35 | CDR-L3: QQWNYPLIT |
| G6 heavy chain variable region | SEQ ID NO. 36 | EVQLQQSGPELEKPGASVKISCKASGFAFTGYNMNWVKQTNGKSLEWI GSIDPYYGGSTYNQKFKDKATLTVDKSSSTAYMQLKSLTSDDSAVYYCAR SPGGDYAMDYWGQGTSVTVSS |
| | SEQ ID NO. 37 | CDR1: GFAFTGYN |
| | SEQ ID NO. 38 | CDR2: IDPYYGGS |
| | SEQ ID NO. 39 | CDR3: ARSPGGDYAMDY |
| G6 light chain variable region | SEQ ID NO. 40 | DIKMTQSPSSMYASVGERVTITCKASQGINSYSGWFQQKPGKSPKTLIYR GNRLVDGVPSRFSGSGSGQDYSLTISSLEYEDMGIYYCLQYDEFPYTFGG GTKLEIK |
| | SEQ ID NO. 41 | CDR1: QGINSY |
| | SEQ ID NO. 42 | CDR2: RGN |
| | SEQ ID NO. 43 | CDR3: LQYDEFPYT |

TABLE 5-continued

Sequence of the 8 pairs of anti-ROR1 scFvs from murine origin, their CDRs of the scFv

| ScFv sequences | SEQ ID # | Raw amino acid sequence |
|---|---|---|
| G3 heavy chain variable region | SEQ ID NO. 44 | QVQLQQPGAELVKPGTSVKLSCKASGYNFTNYWINWVKLRPGQGLEWI GEIYPGSGSTNYNEKFKSKATLTADTSSSTAYMQLSSLASEDSALYYCARD GNYYAMDYWGQGTSVTVSS |
| | SEQ ID NO. 45 | CDR1: GYNFTNYW |
| | SEQ ID NO. 46 | CDR2: IYPGSGST |
| | SEQ ID NO. 47 | CDR3: ARDGNYYAMDY |
| G3 light chain variable region | SEQ ID NO. 48 | DIQMTQTTSSLSASLGDRVTITCRASQDINNYLNWYQQKPDGTVKLLIYY TSALHSGVPSRFSGSGSGTDYSLTISNLEQEDIATYFCQQGNTLPPYTFGG GTKLEIK |
| | SEQ ID NO. 49 | CDR1: QDINNY |
| | SEQ ID NO. 50 | CDR2: YTS |
| | SEQ ID NO. 51 | CDR3: QQGNTLPPYT |
| H10 heavy chain variable region | SEQ ID NO. 52 | EVKLVESGGGLVKPGGSLKLSCAASGFTFSSYAMSWVRQTPEKRLEWVA SISTGASAYFPDSVKGRFTISRDNARNILYLQMSSLRSEDTAMYYCARITT STWYFDVWGAGTTVTVSS |
| | SEQ ID NO. 53 | CDR1-H1: GFTFSSYA |
| | SEQ ID NO. 54 | CDR-H2: ISTGASA |
| | SEQ ID NO. 55 | CDR-H3: ARITTSTWYFDV |
| H10 light chain variable region | SEQ ID NO. 56 | DIKMTQSPSSMYASLGERVTITCKASQDINSYLSWFQQKPGKSPKTLIYR ANRLVDGVPSRFSGSGSGQDYSLTISSLEYEDMGIYYCLQYDEFPYTFGG GTKLEIK |
| | SEQ ID NO. 57 | CDR-L1: QDINSY |
| | SEQ ID NO. 58 | CDR-L2: RAN |
| | SEQ ID NO. 59 | CDR-L3: LQYDEFPYT |
| 2A4 heavy chain variable region | SEQ ID NO. 60 | EVKLQQSGPELVKPGASVKISCKTSGYTFTEYTMHWVKQSHGKSLEWIG GINPNNGGTSYNQKFKGKATLTVDKSSSTAYMELRSLTSEDSAVYYCALQ GFAYWGQGTPLTVSS |
| | SEQ ID NO. 61 | CDR1: GYTFTEYT |
| | SEQ ID NO. 62 | CDR2: INPNNGGT |
| | SEQ ID NO. 63 | CDR3: ALQGFAY |
| 2A4 light chain variable region | SEQ ID NO. 64 | MEIEITQTPALMSASPGEKVTMTCSASSSVSYMYWYQQKPRSSPKPWIY LTSNLASGVPARFSGSGSGTSYSLTISSMEAEDAATYYCQQWSSNPYTFG GGTRLELK |
| | SEQ ID NO. 65 | CDR1: SSVSY |
| | SEQ ID NO. 66 | CDR2: LTS |
| | SEQ ID NO. 67 | CDR3: QQWSSNPYT |
| 1C11 heavy chain variable region | SEQ ID NO. 68 | EVKLQESGAELARPGASVKMSCKASGYTFTSYTMHWVKQRPGQGLEWI GYINPSSGYTEYNQKFKDKTTLTADKSSSTAYMQLSSLTSGDSAVYYCAR RVLWLRRGDYWGQGTILTVSA |
| | SEQ ID NO. 69 | CDR1: GYTFTSYT |
| | SEQ ID NO. 70 | CDR2: INPSSGYT |
| | SEQ ID NO. 71 | CDR3: ARRVLWLRRGDY |
| 1C11 light chain variable region | SEQ ID NO. 72 | MEVLITQTPSSLSASLGERVSLTCRASQDIGSSLNWLQQEPDGTIKRLIYA TSSLDSGVPKRFSGSRSGSDYSLTISSLESEDFVDYYCLQYASSPYTFGGGT KLELK |
| | SEQ ID NO. 73 | CDR1: QDIGSS |
| | SEQ ID NO. 74 | CDR2: ATS |
| | SEQ ID NO. 75 | CDR3: LQYASSP |

TABLE 6

Exemplary Polypeptides forming anti-ROR1 multi-chain CAR

Precursor ROR1 muti-chain CAR polypeptide structure

| Multi chain CAR Designation | Gamma polypeptide | | | | Alpha polypeptide | | | | | | | | Beta polypeptide | |
|---|---|---|---|---|---|---|---|---|---|---|---|---|---|---|
| | FcεRI γ-SP | FcεRI γ ΔTAM | CD3ζ-IC | P2A | FcεRI -SP | CD8α hinge | VH | G4SX3 Linker | VL | FcεRIα-TM-IC | T2A | FcεRIβ- ΔTAM | Costimu-lation. domain |
| anti-ROR1 2A2 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 12 | SEQ ID NO. 3 | SEQ ID NO. 16 | SEQ ID NO. 4 | SEQ ID NO. 11 | SEQ ID NO. 5 | SEQ ID NO. 6 |

TABLE 6-continued

Exemplary Polypeptides forming anti-ROR1 multi-chain CAR

Precursor ROR1 muti-chain CAR polypeptide structure

| Multi chain CAR Designation | Gamma polypeptide | | | | Alpha polypeptide | | | | | | | Beta polypeptide | |
|---|---|---|---|---|---|---|---|---|---|---|---|---|---|
| | FcεRI γ-SP | FcεRI γ ΔTAM | CD3ζ-IC | P2A | FcεRI-SP | CD8α hinge | VH | G4SX3 Linker | VL | FcεRIα-TM-IC | T2A | FcεRIβ-ΔTAM | Costimulation. domain |
| anti-ROR1 4A5 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 20 | SEQ ID NO. 3 | SEQ ID NO. 24 | SEQ ID NO. 4 | SEQ ID NO. 11 | SEQ ID NO. 5 | SEQ ID NO. 6 |
| anti-ROR1 D10 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 28 | SEQ ID NO. 3 | SEQ ID NO. 32 | SEQ ID NO. 4 | SEQ ID NO. 11 | SEQ ID NO. 5 | SEQ ID NO. 6 |
| anti-ROR1 G6 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 36 | SEQ ID NO. 3 | SEQ ID NO. 40 | SEQ ID NO. 4 | SEQ ID NO. 11 | SEQ ID NO. 5 | SEQ ID NO. 6 |
| anti-ROR1 G3 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 44 | SEQ ID NO. 3 | SEQ ID NO. 48 | SEQ ID NO. 4 | SEQ ID NO. 11 | SEQ ID NO. 5 | SEQ ID NO. 6 |
| anti-ROR1 H10 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 52 | SEQ ID NO. 3 | SEQ ID NO. 56 | SEQ ID NO. 4 | SEQ ID NO. 11 | SEQ ID NO. 5 | SEQ ID NO. 6 |
| anti-ROR1 2A4 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 60 | SEQ ID NO. 3 | SEQ ID NO. 64 | SEQ ID NO. 4 | SEQ ID NO. 11 | SEQ ID NO. 5 | SEQ ID NO. 6 |
| anti-ROR1 1C11 (41BB) | SEQ ID NO. 7 | SEQ ID NO. 8 | SEQ ID NO. 9 | SEQ ID NO. 10 | SEQ ID NO. 1 | SEQ ID NO. 2 | SEQ ID NO. 68 | SEQ ID NO. 3 | SEQ ID NO. 72 | SEQ ID NO. 4 | SEQ ID NO. 11 | SEQ ID NO. 5 | SEQ ID NO. 6 |

TABLE 7

Polypeptide sequences of exemplary anti-ROR1 multi-chain CARs

| Name of mc CAR | SEQ ID NO. | Polypeptide sequence |
|---|---|---|
| anti-ROR1 2A2 mcCAR (4-1BB) | SEQ ID NO. 76 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAQV QLQQSGAELVRPGASVTLSCKASGYTFSDYEMHVIQTPVHGLEWIGAIDPETGGTAYNQKFKGKALLTADKSSSTAYMELRSLTSEDSAVYYCTGYYDYDSFTYWGQGT LVTVSAGGGSGGGGSGGGGSDIVMTQSQKIMSTTVGDRVSITCKASQNVDAAVAWYQQKPGQSPKLLIYSASNRYTGVPDRFTGSGSGTDFTLTISNMQSEDLADYFC QQYDIYPYTFGGGTKLEIKTTTPAPRPPTPAPTIASQPLSLRPEACRPAAGGAVHTRGLDFACDFFIPLLVVILFAVDTGLFISTQQQVTFLLKIKRTRKGPRLLNPHPKPNPKN NGSGEGRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEGDI FSSFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKG NKVPEKRGRKKLLYIFKQPFMRPVQTTQEEDGCSCRFPEEEEGGCEL |
| anti-ROR1 4A5 mcCAR (4-1BB) | SEQ ID NO. 77 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAEV KLVESGGGLIVKPGGSLKLSCAASGFTFSSYAMSWVRQIPEKRLEWVASISRGGTTYYPDSVKGRFTISRDNVRNILYIQMSLRSEDTAMYCGRYDYDGYYAMDYWGQG TSVTVSSGGGGSGGGGSGGGGSDIKMTQSPSSMYASLGERVTITCKASPDINSYLSWFQQKPGKSPKTLIYRANRLVDGVPSRFSGSGGQDYSLTINSLEYEDMGIYYCL QYDEFPYTFGGGTKLEMKTTTPAPRPPTPAPTIASQPLSLRPEACRPAAGGAVHTRGLDFACDFFIPLLVVILFAVDTGLFISTQQQVTFLLKIKRTRKGFRLLNPHPKPNPKN NGSGEGRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEGDI FSSFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKG NKVPEKRGRKKLLYIFKQPFMRPVQTTQEEDGCSCRFPEEEEGGCEL |
| anti-ROR1 D10 mcCAR (4-1BB) | SEQ ID NO. 78 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAQV QLKESGPGIVAPSQTLSITCTVSGFSLTSYGVHWRQPPGKGLEWLGVIWAGGFTNVNSALKRSLSISKDNSKSQVLLKMTSLQTDDTAMYCARRGSSYSMDYWGQGT SVTVSSGGGGSGGGGSGGGGSQPAITAASLGQKVTITCSASSNVSYIHWYQQRSGTSPRPWIYEISKLASGVPVRFSGSGSGTSYSLTISSMEAEDAAIYYCQQWN YPLITFGSGTKLEIQTTTPAPRPPTPAPTIASQPLSLRPEACRPAAGGAVHTRGLDFACDFFIPLLVVILFAVDTGLFISTQQQVTFLLKIKRTRKGFRLLNPHPKPNPKNNGSGE GRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEGDIFSSFKA GYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNKVPEK RGRKKLLYIFKQPFMRPVQTTQEEDGCSCRFPEEEEGGCEL |
| anti-ROR1 G6 mcCAR (4-1BB) | SEQ ID NO. 79 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAEV QLQQSGPELEKPGASVKISCKASGFAFTGYNMMWVKQINGKSLEWIGSIDPYYGGSTNQKFKDKATLTVDKSSSTAYMQLKSLTSDDSAVYYCARSPGGDYAMDYWG QGTSVTVSSGGGGSGGGGSGGGGSDIKMTQSPSSMYASVGERVTITCKASQGINSYSGWFQQKPGKSPKTLIYRGNRLVDGVPSRFSGSGSGQDYSLTISSLEYEDMGIY YCLQLYQDEFPYTFGGGTKLEIKTTTPAPRPPTPAPTIASQPLSLRPEACRPAAGGAVHTRGLDFACDFFIPLLVVILFAVDTGLFISTQQQVTFLLKIKRTRKGFRLLNPHPKPNPK NNGSGEGRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEG DIFSSFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELK GNKVPEKRGRKKLLYIFKQPFMRPVQTTQEEDGCSCRFPEEEEGGCEL |
| anti-ROR1 G3 mcCAR (4-1BB) | SEQ ID NO. 80 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAQV QLQQPGAELVKPGTSVKLSGGDLQMTQTTSSLSASLGDRVTITCRASQDINNYLNWYQQKPDGTVKLLIYTSALHSGVPSRFSGSGSGTDYSLTISNLEQEDIATYFCQQ GNTLPPYTFGGGTKLEIKTTTPAPRPPTPAPTIASQPLSLRPEACRPAAGGAVHTRGLDFACDFFIPLLVVILFAVDTGLFISTQQQVTFLLKIKRTRKGFRLLNPHPKPNPKNN GSGEGRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEGDIFS SFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNK VPEKRGRKKLLYIFKQPFMRPVQTTQEEDGCSCRFPEEEEGGCEL |

TABLE 7-continued

Polypeptide sequences of exemplary anti-ROR1 multi-chain CARs

| Name of mc CAR | SEQ ID NO. | Polypeptide sequence |
|---|---|---|
| anti-ROR1 H10 mcCAR (4-1BB) | SEQ ID NO. 81 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAEV KLVESGGGLVKPGGSLKLSCAASGFTFSSYAMSWVRQTPEKRLEWVASISTGASAYFPDSVKGRFTISRDNARNILYLQMSLRSEDTAMYYCARITTSTWYFDVWGAGTT VTVSSGGGGSGGGGSGGGGSDIKMTQSPSSMYASLGERVTITCKASQDINSYLSWFQQKPGKSPKTLIYRANRLVDGVPSRFSGSGSGQDYSLTISSLEYEDMGIYYCLQY DERPYTFGGGTKLEIKTTTPAPRPPTPAPTIASQPLSLRPEACRPAAGGAVHTRGLDFRACDFFIPLLVVILFAVDTGLFISTQQQVTFLLKIKRTRKGFRLLNPHPKPNPKNNGS GEGRGSLLTCGDVEENPGPMDTESNRRANLALPQEPSSVPAFVEISPQEVSSGRLLKSASSPPLHTWLTVLKKEQEFLGVTQILTAMICLCFGTVVCSVLDISHIEGDIFSSF KAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNKVP ERRGRKKLLYIFKQPFMRPVQTTQEEDGCSCRFPEEEGGCEL |
| anti-ROR1 2A4 mcCAR (4-1BB) | SEQ ID NO. 82 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAEV KLQQSGPELVKPGASVKISCKTSGYTFTEYTMHWVKQSHGKSLEWIGGINPNNGGTSYNQKFKGKATLTVDKSSSTAYMELRSLTSEDSAVYYCALQGFAYWGQGTPLTV SSGGGGSGGGGSGGGGSMEIEITQTPALMSASPGEKVTMTCSASSSVSYMYWYQQKPRSSPKPWIYLTSNLASGVPARFSGSGSGTSYSLTISSMEABDAATYYCQQWS SNPYTFGGGTRLELKTTTPAPRPPTPAPTIASQPLSLRPEACRPAAGGAVHTRGLDFACDFFIPLLVVILFAVDTGLFISTQQQVTFLLKIKRTRKGFRLLNPHPKPNKNNGSG EGRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEGDIFSSFK AGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNKVPE KRGRKKLLYIFKQPFMRPVQTTQEEDGCSCRFPEEEGGCEL |
| anti-ROR1 1C11 mcCAR (4-1BB) | SEQ ID NO. 83 | MIPAVVLLLLLVEQAAALGEPQLCYILDAILFLYGIVLTLLYCRLKIQVRKAAITSYEKSRVKFSRSADAPAYQQGQNQLYNELNLGRREEYDVLDKRRGRDPEMGGKPRRKN PQEGLYNELQKDKMAEAYSEIGMKGERRRGKGHDGLYQGLSTATKDTYDALHMQALPPRGSGATNFSLLKQAGDVEENPGPMAPAMESPTLLCVALLFFAPDGVLAEV KLQESGAELARPGASVKMSCKASGYTFTFTSYTMHWVKQRPGQGLEWIGYINPSSGYTEYNQKFKDKTTLTADKSSSTAYMQLSSLTSGDSAVYYCARRVLWLRRGDYWG QGTILTVSAGGGSGGGGSGGGGSMEVLITQTPSSLASLGERVSLICRASQDIGSSLNWLQQEPDGTIKRLIYATSSLDSGVPKRFSGSRSGSDYSLTISSLESEDFVDYYCL QYASSPYITFGGGTKLELKTTTPAPRPPTPAPTIASQPLSLRPEACRPAAGGAVHTRGLDFACDFFIPLLVVILFAVDTGLFISTQQQVTFLLKIKRTRKGFRLLNPHPKPNPKNN GSGEGRGSLLTCGDVEENPGPMDTESNRRANLALPQEPSSVPAFEVLEISPQEVSSGRLLKSASSPPLHTWLTVLKKEQEFLGVTQILTAMICLCFGTVVCSVLDISHIEGDIFS SFKAGYPFWGAIFFSISGMLSIISERRNATYLVRGSLGANTASSIAGTGTITILIINLKKSLAYIHIHSCQKFFETKCFMASFSTEIVVMMLFLTILGLGSAVSLTICGAGEELKGNK VPEKRGRKKLLYIFKQPFMRPVQTTQEEDGCSCRFPEEEGGCEL |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Multi-Chain Chimeric Antigen Receptor (CAR)

The present invention relates to a multi-chain chimeric antigen receptor (CAR) particularly adapted to immune cells used in immunotherapy.

The multi-chain CAR according to the invention generally comprises at least:
one transmembrane polypeptide comprising at least one extracellular ligand-biding domain and;
one transmembrane polypeptide comprising at least one signal-transducing domain;
such that said polypeptides assemble together to form a multi-chain Chimeric Antigen Receptor.

The term "extracellular ligand-binding domain" as used herein is defined as an oligo- or polypeptide that is capable of binding a ligand. Preferably, the domain will be capable of interacting with a cell surface molecule.

In a preferred embodiment, said extracellular ligand-binding domain is a single chain antibody fragment (scFv) comprising the light ($V_L$) and the heavy ($V_H$) variable fragment of a target antigen specific monoclonal antibody specific to ROR1 joined by a flexible linker. In a preferred embodiment, said scFv is an anti-ROR1 scFV, preferably provided in Table 5 as SEQ ID NO.12, 16, 20, 24, 28 and 32. Binding domain specific to ROR1 other than scFv can also be used for predefined targeting of lymphocytes, such as camelid or shark (VNAR) single-domain antibody fragments or receptor ligands like a vascular endothelial growth factor polypeptide, an integrin-binding peptide, heregulin or an IL-13 mutein, antibody binding domains, antibody hypervariable loops or CDRs as non-limiting examples.

As other examples provided in Table 5 are the anti-ROR1 scFV of sequences SEQ ID NO.36, 40, 44, 48, 52, 56, 60, 64, 68 and 72.

The present invention relates more particularly to a ROR1 specific multi-chain Chimeric Antigen Receptor (mc CAR) comprising:
a transmembrane polypeptide from the alpha chain of high-affinity IgE receptor (FcεRI) fused to an extracellular ROR1 ligand binding domain;
a second transmembrane polypeptide from the gamma chain of FcεRI fused to a signal transducing domain;
a third transmembrane polypeptide from the beta chain of FcεRI comprising a co-stimulatory domain.
wherein said ROR1 ligand binding domain fused to said alpha chain of FcεRI is a single-chain variable fragment (scFv) comprising heavy ($V_H$) and light ($V_L$) chains conferring specificity to ROR1,
wherein said $V_H$ comprises a polypeptide sequence displaying at least 90%, at least 95%, at least 98% or at least 99% identity to one selected from SEQ ID NO. 28 (D10), SEQ ID NO. 12 (2A2), SEQ ID NO. 20 (4A5), SEQ ID NO. 36 (G6), SEQ ID NO. 44 (G3), SEQ ID NO. 52 (H10), SEQ ID NO. 60 (2A4) and SEQ ID NO. 68 (1C11), and,
wherein said $V_L$ comprises a polypeptide displaying at least 90%, at least 95%, at least 98% or at least 99% sequence identity to one selected from SEQ ID NO. 32 (D10), SEQ ID NO. 16 (2A2), SEQ ID NO. 24 (4A5), SEQ ID NO. 40 (G6), SEQ ID NO. 48 (G3), SEQ ID NO. 56 (H10), SEQ ID NO. 64 (2A4) and SEQ ID NO. 72 (1C11).
It is understood that the previously cited VH and VL chains function as pairs, i.e. for instance, the VH chain of F10 antibody is to be used in combination avec the VL chain of the same antibody (F10).

According to a more preferred embodiment, said $V_H$ and VL comprises a polypeptide sequence displaying at least 90%, at least 95%, at least 98% or at least 99% sequence identity respectively to SEQ ID NO. 28 and SEQ ID NO. 32 (D10), or respectively to SEQ ID.12 or SEQ ID NO. 16 (2A2).

According to another embodiment, wherein said extra cellular ligand binding-domain comprises:
a VH chain comprising the CDRs from the mouse monoclonal antibody D10 of SEQ
ID NO. 29 (CDR-H1), SEQ ID NO.30 (CDR-H2) and SEQ ID NO.31 (CDR-H3), and a VL chain comprising the CDRs from the mouse monoclonal antibody D10 of NO. 33 (CDR-L1), SEQ ID NO.34 (CDR-L2) and SEQ ID NO:35 (CDR-L3)
or;
a VH chain comprising the CDRs from the mouse monoclonal antibody 2A2 of SEQ ID NO. 13 (CDR-H1), SEQ ID NO.14 (CDR-H2) and SEQ ID NO.15 (CDR-H3) and a VL chain comprising the CDRs from the mouse monoclonal antibody 2A2 of SEQ ID NO. 17 (CDR-L1), SEQ ID NO:18 (CDR-L2) and SEQ ID NO:19 (CDR-L3).

In a preferred embodiment, said extracellular ligand-binding domain is a single chain antibody fragment (scFv) comprising the light ($V_L$) and the heavy ($V_H$) variable fragment of a target antigen specific monoclonal antibody specific to ROR1 joined by a flexible linker.

In a preferred embodiment, said scFv is an anti-ROR1 scFV, or parts of them such as CDRs preferably provided in Table 5 as SEQ ID NO.12 to 75. From all scFvs cited in Table 5, the preferred pairs of scFvs correspond to the VH and VL chains of D10 (SEQ ID NO.28 and 32) and 2A2 (SEQ ID NO.12 and 16), as well as their respective CDRs (SEQ ID NO.29-31 and 33-35 corresponding respectively to VH and VL chains for D10; SEQ ID NO.13-15 and 17-19 corresponding respectively to VH and VL chains for 2A2).

Binding domain specific to ROR1 other than scFv can also be used for predefined targeting of lymphocytes, such as camelid or shark (VNAR) single-domain antibody fragments or receptor ligands like a vascular endothelial growth factor polypeptide, an integrin-binding peptide, heregulin or an IL-13 mutein, antibody binding domains, antibody hypervariable loops or CDRs as non-limiting examples.

In a preferred embodiment said first transmembrane polypeptide further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain (e.g. NP_001139345.1) (SEQ ID NO: 2).

Thus, the expression of multi-chain CAR in immune cells results in modified cells that selectively and eliminate defined targets, including but not limited to malignant cells carrying a respective tumor-associated surface antigen or virus infected cells carrying a virus-specific surface antigen, or target cells carrying a lineage-specific or tissue-specific surface antigen.

Downregulation or mutation of target antigens is commonly observed in cancer cells, creating antigen-loss escape variants. Thus, to offset tumor escape and render immune cell more specific to target, the multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FcεRI beta and/or gamma chain fused to a signal-transducing domain and several part of FcεRI alpha chains fused to different extracellular ligand binding domains. In a more particular embodiment, said method comprises introducing into said cell at least one polynucleotide which encodes a part of FcεRI beta and/or gamma chain fused to a signal-transducing domain and several FcεRI alpha chains fused to different extracellular ligand biniding domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

According to a preferred embodiment, the polypeptide encoding a ROR1 specific multi-chain Chimeric Antigen Receptor, comprises a polypeptide sequence displaying at least 80%, at least 90%, at least 95%, at least 98% or at least 99% identity to the full amino acid sequence of SEQ ID NO. 78 (anti-ROR1 mcCAR D10), SEQ ID NO.76 (anti-ROR1 mcCAR 2A2), SEQ ID NO.77 (anti-ROR1 mcCAR 4A5), SEQ ID NO.79 (anti-ROR1 mcCAR G6), SEQ ID NO.80 (anti-ROR1 mcCAR G3), SEQ ID NO.81 (anti-ROR1 mcCAR H10), SEQ ID NO.82 (anti-ROR1 mcCAR 2A4) and SEQ ID NO.83 (anti-ROR1 mcCAR 1C11) as referred to in Table 7.

According to a more preferred embodiment, the polypeptide encoding a ROR1 specific multi-chain Chimeric Antigen Receptor comprises a polypeptide sequence displaying at least 80%, at least 90%, at least 95%, at least 98% or at least 99% identity to the full amino acid sequence of SEQ ID NO. 78 (anti-ROR1 mcCAR D10), SEQ ID NO.76 (anti-ROR1 mcCAR 2A2) as referred to in Table 7.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In another particular embodiment, said signal transducing domain is a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

In a preferred embodiment, the signal transduction domain of the multi-chain CAR of the present invention comprises a part of co-stimulatory signal molecule which is 4-1BB (GenBank: AAA53133.).

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the multi-chain CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein. As non limiting examples, the transmembrane polypeptide can be a subunit of the T cell receptor such as α, β, γ or ?, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine.

The term "derived from" means a polypeptide having an amino acid sequence which is equivalent to that an FcE receptor which include one or more amino acid modification(s) of the sequence of the FcE receptor. Such amino acid modification(s) may include amino acid substitution(s), deletion(s), addition(s) or a combination of any of those modifications, and may alter the biological activity of the Fc binding region relative to that of an Fc receptor. On the other hand, Fc binding regions derived from a particular Fc receptor may include one or more amino acid modification(s) which do not substantially alter the biological activity of the Fc binding region relative to that of an Fc receptor. Amino acid modification(s) of this kind will typically comprise conservative amino acid substitution(s).

In a particular embodiment, the multi-chain CAR comprises a transmembrane polypeptide derived from a FcεRI chain. In more particular embodiment FcεRI chain is a FcεRI α chain, in which the extracellular domain is replaced by an extracellular ligand-binding domain, preferably by a scFV directed against ROR1.

In more particular embodiment, said multi-chain CAR can comprise a part of FcεRI alpha chain and a part of FcεRI beta chain or variant thereof such that said FcεRI chains spontaneously dimerize together to form a dimeric Chimeric Antigen Receptor. In another embodiment, the multi-chain Chimeric Antigen can comprise a part of FcεRI alpha chain and a part of a FcεRI gamma chain or variant thereof such that said FcεRI chains spontaneously trimerize together to form a trimeric Chimeric Antigen Receptor, and in another embodiment the multi-chain Chimeric Antigen Receptor can comprise a part of FcεRI alpha chain, a part of FcεRI beta chain and a part of FcεRI gamma chain or variants thereof such that said FcεRI chains spontaneously tetramerize together to form a tetrameric Chimeric Antigen Receptor.

Figure 4:
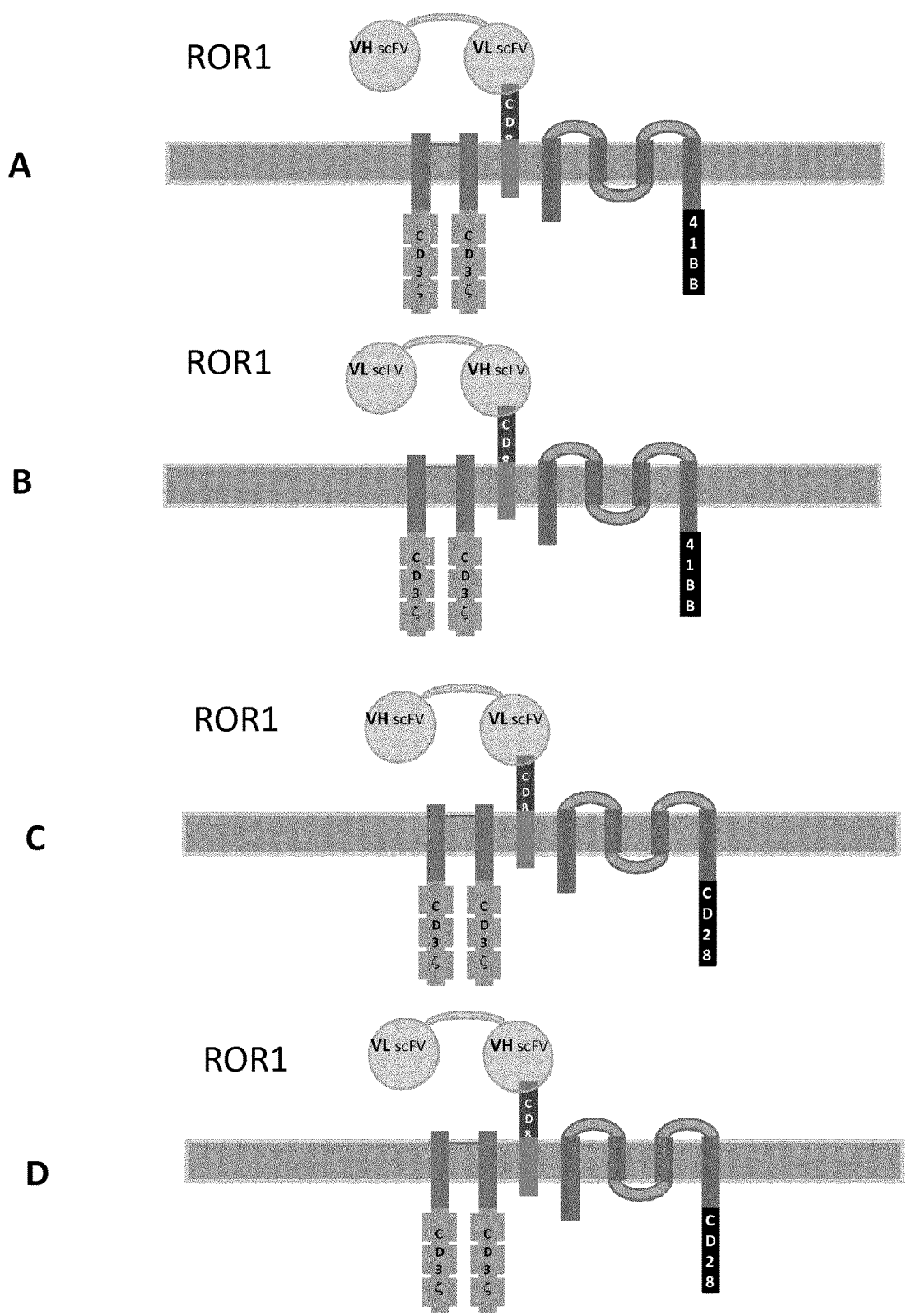
FIG. 4: Different architectures of the ROR1 specific muti-chain CAR according to the invention. From left to right: polypeptide gamma (fused to ITAM of CD3zeta), polypeptide alpha (fused to ScFv), polypeptide beta (fused to co-stimulatory domain from 41BB in A and B, and CD28 in C and D). A and B: polypeptide beta is fused to co-stimulatory domain from 41BB, VL and VH fragments being in opposite orders.

As non-limiting example, different versions (architectures) of multi-chain CAR are illustrated in FIG. 4. In a more preferred embodiment, the multi-chain CARs of the present invention comprises a polypeptide comprising amino acid sequences as set forth in Table 6. In a preferred embodiment the multi-chain CAR comprise a polypeptide with amino acid sequence that has at least 70%, preferably at least 80%, more preferably at least 90%, 95% 97% or 99% sequence identity with such amino amino acid sequences or with the polynucleotide sequence encoding one two or three of the polypeptides constitutive of the multi-chain polypeptide structure.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

Polynucleotides, Vectors:

The present invention also relates to polynucleotides, vectors encoding the above described multi-chain CAR according to the invention. The present invention provides polynucleotides, including DNA and RNA molecules that encode the transmembrane polypeptides disclosed herein that can be included in the multi-chain CAR. In particular, the invention relates to a polynucleotide comprising a nucleic acid sequence encoding at least one transmembrane polypeptide composing the multi-chain CAR as described above. More particularly the invention relates to a polynucleotide comprising two or more nucleic acid sequences encoding transmembrane polypeptides composing the multi-chain CAR as described above.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the different polypeptides of the multi-chain CAR.

To direct, transmembrane polypeptide such as FcER into the secretory pathway of a host cell, a secretory signal sequence (also known as a leader sequence, prepro sequence or pre sequence) is provided in polynucleotide sequence or vector sequence. The secretory signal sequence may be that of FcER, or may be derived from another secreted protein (e.g., t-PA) or synthesized de novo. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the residues 1 to 25 of the FcεRI alpha chain (NP_001992.1).

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering an Immune Cell:

In encompassed particular embodiment, the invention relates to a method of preparing immune cells for immunotherapy comprising introducing into said immune cells the polypeptides composing said multi-chain CAR and expanding said cells. In particular embodiment, the invention relates to a method of engineering an immune cell comprising providing a cell and expressing at the surface of said cell at least one multi-chain CAR as described above. In particular embodiment, the method comprises transforming the cell with at least one polynucleotide encoding polypeptides composing at least one multi-chain CAR as described above, and expressing said polynucleotides into said cell.

In another embodiment, the present invention relates to a method of preparing cells for immunotherapy comprising introducing into said cells the different polypeptides composing said multi-chain CAR and expanding said cells. In a preferred embodiment, said polynucleotides are included in lentiviral vectors in view of being stably expressed in the cells.

Delivery Methods

The different methods described above involve introducing multi-chain CAR, pTalpha or functional variants thereof, rare cutting endonuclease, TALE-nuclease, CAR optionally with DNA-end processing enzyme or exogenous nucleic acid into a cell.

As non-limiting example, said multi-chain CAR can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme or the different polypeptides of the multi-chain CAR.

Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into animal cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Electroporation

In particular embodiment of the invention, polynucleotides encoding polypeptides according to the present invention can be mRNA which is introduced directly into the cells, for example by electroporation. The inventors determined the optimal condition for mRNA electroporation in T-cell.

The inventor used the cytoPulse technology which allows, by the use of pulsed electric fields, to transiently permeabilize living cells for delivery of material into the cells. The technology, based on the use of PulseAgile (Cellectis property) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

In particular embodiments, as non-limiting examples, said RNA encodes a rare-cutting endonuclase, one monomer of the rare-cutting endonuclease such as Half-TALE-nuclease, a Chimeric Antigen Receptor, at least one component of the multi-chain chimeric antigen receptor, a pTalpha or functional variant thereof, an exogenous nucleic acid, one additional catalytic domain.

Engineered T-Cells

The present invention also relates to isolated cells or cell lines susceptible to be obtained by said method to engineer cells. In particular said isolated cell comprises at least one multi-chain CAR as described above. In another embodiment, said isolated cell comprises a population of multi-chain CARs each one comprising different extracellular ligand binding domains. In particular, said isolated cell comprises exogenous polynucleotide sequences encoding polypeptides composing at least one multi-chain CAR.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As mentioned previously, such cells can be also genetically engineered to inactivate one or several genes selected, for instance, from the group consisting of CD52, GR, TCR alpha, TCR beta, HLA gene, immune check point genes such as PD1 and CTLA-4, or can express a pTalpha transgene.

In another embodiment, TCR is rendered not functional in the cells according to the invention by inactivating TCR alpha gene and/or TCR beta gene(s). The above strategies are used more particularly to avoid GvHD. In a particular aspect of the present invention is a method to obtain modified cells derived from an individual, wherein said cells can proliferate independently of the Major Histocompatibility Complex signaling pathway. Said method comprises the following steps:

(a) Recovering cells from said individual;
(b) Genetically modifying said cells ex-vivo by inactivating TCR alpha or TCR beta genes;
(c) Cultivating genetically modified T-cells in vitro in appropriate conditions to amplify said cells.

Figure 9:
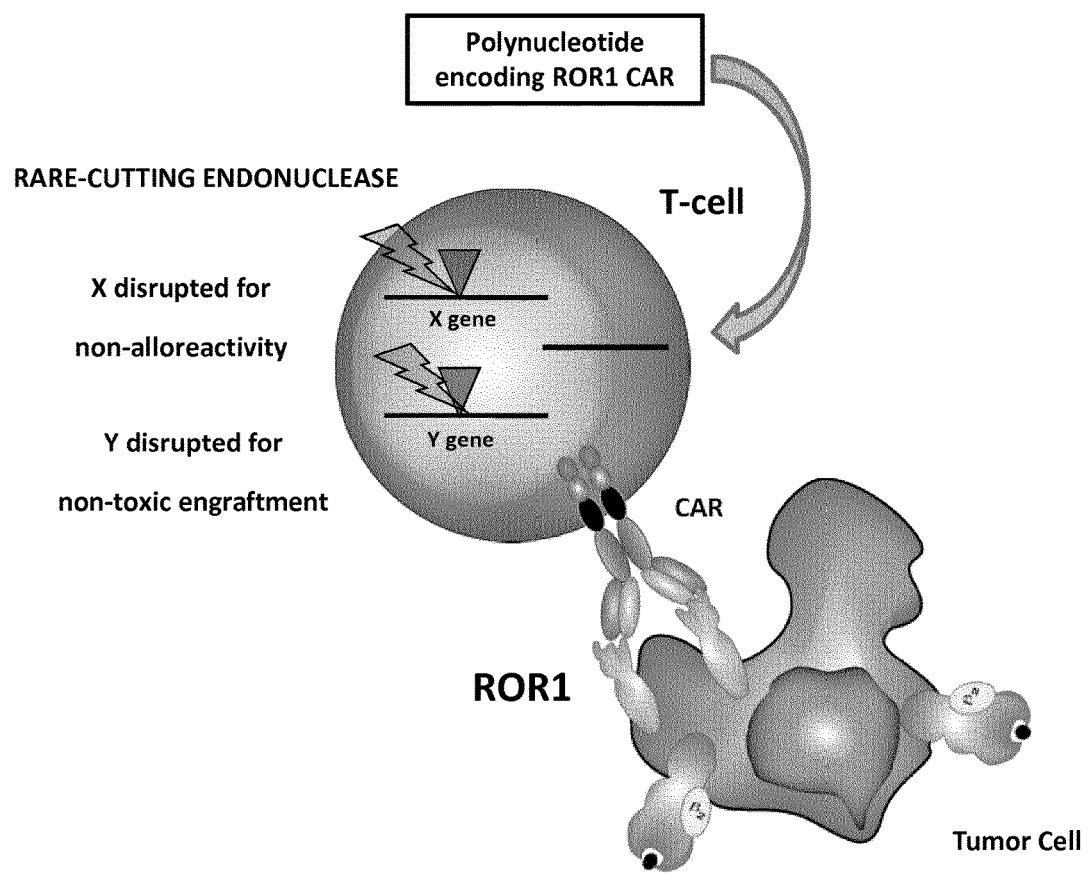
FIG. 9: Schematic representation of the inactivation of TCR gene(s) in anti-ROR1 CAR T cells to render these allogeneic and therefore to minimize Host versus Graft (HvG) rejection and Graft versus Host Disease (GvHD).

Modified cells, which can proliferate independently of the Major Histocompatibility Complex signaling pathway, susceptible to be obtained by this method are encompassed in the scope of the present invention. Said modified cells can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes (FIG. 9 for a schematic representation).

For instance, heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in the following Table 8.

TABLE 8

TAL-nucleases targeting TCRalpha gene

| Target | Target sequence | Repeat sequence | Half TALE-nuclease |
|---|---|---|---|
| TRAC_T01 | TTGTCCCACAGATATCCAgaaccctgaccctg CCGTGTACCAGCTGAGA (SEQ ID NO: 84) | Repeat TRAC_T01-L (SEQ ID NO: 85) Repeat TRAC_T01-R (SEQ ID NO: 86) | TRAC_T01-L TALEN (SEQ ID NO: 87) TRAC_T01-R TALEN (SEQ ID NO: 88) |

In a more preferred embodiment, said method comprises:

(a) Providing a T-cell, preferably from a cell culture or from a blood sample;
(b) Transforming said T cell with nucleic acid encoding a rare-cutting endonuclease able to selectively inactivate by DNA cleavage, preferably by double-strand break at least one gene encoding a component of the T-cell receptor (TCR);
(c) Expressing said rare-cutting endonucleases into said T-cells;
(d) Sorting the transformed T-cells, which do not express TCR on their cell surface;
(e) Expanding said cells.

In another embodiment, said rare-cutting endonuclease can be a meganuclease, a Zinc finger nuclease or a TALE-nuclease. In a preferred embodiment, said rare-cutting endonuclease is a TALE-nuclease. Preferred methods and relevant TALE-nucleases have been described in WO2013176915

Anti-ROR1 T-Cells Made Resistant to Chemotherapy

According to a preferred embodiment of the invention, the T-cells endowed with anti ROR1 multi-chain CAR are engineered to be resistant to chemotherapy drugs, in particular to purine nucleotide analogues (PNAs), making them suitable for cancer treatments combining adoptive immunotherapy and chemotherapy.

Purine nucleotide analogues enter chemotherapy compositions for many cancer treatments and are used as a standard of care in CLL. The most widely used PNAs are clofarabine, fludarabine and cytarabine, alone or in combination.

PNAs are metabolized by deoxycytidine kinase (dCK) into mono, -di and tri-phosphate PNA. Their tri-phosphate forms and particularly clorofarabine triphosphate compete with ATP for DNA synthesis, acts as pro-apotptotic agent and are potent inhibitors of ribonucleotide reductase (RNR), which is involved in trinucleotide production.

The present inventors have successfully created anti-ROR1 T-cells resistant to purine nucleotide analogues, more particularly clorofarabine and fludarabine, by mediating the inactivation of dcK gene expression into said cells. Transfection of the T-cells using polynucleotides encoding specific TAL-nuclease directed against dck genes, preferably by using electroporation of mRNA, induced a significant resistance to the drugs, while maintaining T-cells cytotoxic activity towards ROR1 bearing cells.

The present application thus provides with anti-ROR1 T-cells, which expression of deoxycytidine kinase has been repressed or inactivated for the treatment of leukemia.

Activation and Expansion of T Cells

Whether prior to or after genetic modification of the T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell.

For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, INFγ, 1L-4, 1L-7, GM-CSF, −10, −2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer or infections in a patient diagnosed with a pathology linked to ROR1 positive cells. In another embodiment, said isolated cell according to the invention or cell line derived from said isolated cell can be used in the manufacture of a medicament for treatment of a cancer, especially CLL or solid tumors such as breast, colon, lung or kidney tumors In another aspect, the present invention relies on methods for treating patients in need thereof, said method comprising at least one of the following steps:

(a) providing an immune-cell obtainable by any one of the methods previously described;

(b) Administrating said transformed immune cells to said patient,

On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the multi-chain CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Cells that can be used with the disclosed methods are described in the previous section. Said treatment can be used to treat patients diagnosed wherein a pre-malignant or malignant cancer condition characterized by ROR1-expressing cells, especially by an overabundance of ROR1-expressing cells. Such conditions are found in hematologic cancers, such as leukemia or malignant lymphoproliferative disorders.

Leukemia can be acute myelogenous leukemia, chronic myelogenous leukemia, melodysplastic syndrome, acute lymphoid leukemia, chronic lymphoid leukemia, and myelodysplastic syndrome.

Lymphoproliferative disorder can be lymphoma, in particular chronic lymphocytic leukemia, non-Hodgkin's lymphoma, Burkitt's lymphoma, and follicular lymphoma (small cell and large cell).

According to one preferred embodiment, said engineered T cells are provided for the treatment of the Chronic Lymphocytic Leukemia (CLL) or the Small Lymphocytic Lymphoma (SLL).

According to another preferred embodiment, said treatment of CLL or SLL is administered to patients who have been lympho-depleted before the ROR1-CAR-T cell infusion. Said lympho-depletion is performed usually by chemotherapy, and preferably by using drugs as fludarabine (F), cyclophosphamide (C), bendamustine (B) or rituximab (R) or a combination thereof. Typically, the combination of FCR or FBR can be used for lympho-depletion prior to CAR-T administration.

According to another preferred embodiment, said engineered T cells are provided for the treatment of Mantle Cell Lymphoma (MCL, Acute Lymphoblastic Leukemia (ALL) with a t(1;19) chromosome translocation.

Also, solid tumors such as breast, colon, lung, and kidney tumors can be treated by the CARs of the invention. Also, the engineered T cells of the invention can be used as a treatment of pancreas or ovarian cancers.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

General Methods

Primary Cells

Peripheral blood mononuclear cells were isolated by density gradient centrifugation from buffy coats from healthy volunteer donors (Etablissement Francais du Sang). T lymphocytes were then purified using the EasySep human T cell enrichment kit (Stemcell Technologies), and activated with Dynabeads Human T-Activator CD3/CD28 (Life Technologies) in X-vivo 15 medium (Lonza) supplemented with 20 ng/ml IL-2 (Miltenyi) and 5% human AB serum (Seralab).

Cell Lines

The Jeko-1 and SupT1 cell lines were obtained from the American Type Culture Collection. Jeko-1 cells were cultured in RPMI 1640 supplemented with 20% heat-inactivated FCS, 2 mmol/L L-glutamine and 100 units/ml penicillin, and 100 µg/mL streptomycin. SupT1 cells were cultured in RPMI 1640 supplemented with 10% heat-inactivated FCS, 2 mmol/L L-glutamine and 100 units/ml penicillin, and 100 µg/mL streptomycin.

Synthesis of DNA Encoding mcCARs

The DNA encoding the mcCARs was synthesized by GenScript.

Construction of Polycistronic Lentiviral Vectors

The DNA encoding the mcCARs was cloned in the pSEW lentiviral vector backbone between the SFFV promoter and the WPRE sequence.

Lentiviral Vectors Production

Concentrated lentiviral vectors were produced by Vectalys (Toulouse, France).

T Cells Transduction

After 3 days of activation, T cells were transduced on retronectin coated plates at an MOI of 5.

Detection of mcCAR mcCARs detection at the surface of T cells was done using a recombinant protein consisting of the fusion of the extracellular domain of ROR1 protein together with a murine IgG1 Fc fragment (produced by LakePharma). Binding of this protein to the CAR molecule was detected with a PE-conjugated secondary antibody (Jackson Immunoresearch) targeting the mouse Fc portion of the protein, and analysed by flow cytoùmetry.

Degranulation Assay $5 \times 10^4$ T cells were co-cultured with $5 \times 10^4$ ROR1-positive or ROR1-negative cells in 0.1 ml per well in a 96-well plate. APC-labeled anti-CD107a (BD Biosciences) was added at the beginning of the co-culture in addition to 1 µg/ml of anti-CD49d (BD Biosciences), 1 µg/ml of anti-CD28 (Miltenyi), and 1× Monensin solution (eBioscience). After a 6 h incubation, the cells were stained with a fixable viability dye (eBioscience) and vioblue-labeled anti-CD8 (Miltenyi) and analyzed using the MACSQuant flow cytometer (Miltenyi). Of note: degranulating cytotoxic T cells correspond to CD8+CD107a+ cells.

Cytokine Release Assay $5 \times 10^4$ T cells were co-cultured with $5 \times 10^4$ ROR1-positive or ROR1-negative cells in 0.1 ml per well in a 96-well plate. After a 24 hours incubation, the culture supernatants were collected and analysed for INFγ NFγ sed for e or ROR1-negative cells Cytotoxicity Assay ROR1-positive and ROR1-negative cells were respectively labeled with CellTrace CFSE and CellTrace Violet. A batch of $1 \times 10^4$ ROR1-positive cells were co-cultured with $1 \times 10^4$ ROR1negative cells with $1 \times 10^5$ T cells in 0.1 ml per well in a 96-well plate. After a 4 hours incubation, the cells were harvested and stained with a fixable viability dye (eBioscience) and analyzed using the MACSQuant flow cytometer (Miltenyi).

The percentage of specific lysis was calculated using the following formula:

$$\% \text{ cell lysis} = 100\% - \frac{\frac{\% \text{ viable target cells upon coculture with } CAR \text{ modified } T \text{ cells}}{\% \text{ viable control cells upon coculture with } CAR \text{ modified } T \text{ cells}}}{\frac{\% \text{ viable target cells upon coculture with non modified } T \text{ cells}}{\% \text{ viable control cells upon coculture with non modified } T \text{ cells}}}$$

Example of ROR1 Specific Multi-Chain CARs

A. Design of Multi-Chain CARs

Ten multi-chain CARs targeting the ROR1 antigen were designed based on the high affinity receptor for IgE (FcεRI). The FcεRI expressed on mast cells and basophiles triggers allergic reactions. It is a tetrameric complex composed of a single α subunit, a single β subunit and two disulfide-linked γ subunits. The α subunit contains the IgE-binding domain. The β and γ subunits contain ITAMs that mediate signal transduction. In every multi-chain CAR, the extracellular domain of the FcRα chain was deleted and replaced by the respective scFv referred to µ ln Table 5 respectively and the CD8α hinge (SEQ ID NO: 2) and the ITAM of the FcRβ chain and/or the FcRγ chain was deleted. The resulting constructions had the structure detailed in table 6.

Architecture of ROR1-Specific Multi-Chain CAR (csm13 and csm14)

The 2 mcCARs specific for ROR1 developed and tested in the present invention have a CAR architecture as depicted in FIG. 4A and with components of α, β and γ chains as shown in Tables 1-3. These 2 receptors differ from each other only by their antigen-binding domain. The csm13 CAR contains the D10 scFv whereas csm14 CAR contains the 2A2 scFv as shown in Table 5. Both csm13 and csm14 contain the 41-BB costimulatory domain and the CD3zeta ITAMs as signaling domains.

Figure 3:
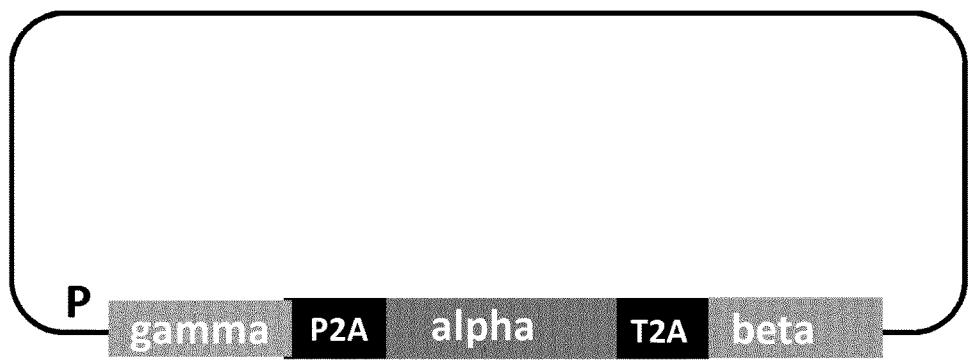
FIG. 3: General structure of the polycistronic construct encoding the ROR1 muti-chain CAR according to the invention. The one described in the examples of the present invention is based on a polycistronic lentiviral vector such as pSEW.

The polycistronic expression cassettes in lentiviral vector encoding ROR1-specific mcCAR cms13 and cms14 are realized as in FIG. 3.

The polypeptide sequence of cms13 and cms14 correspond to SEQ ID NO:78 and SEQ ID NO:76 as shown in Table 7.

B. Transiently Expression in T Cells

Multi-chain CARs are expressed in human T cells after electroporation of polycistronic mRNA. T cells were electroporated with capped and polyadenylated polycistronic mRNA that were produced using the mMESSAGE mMACHINE kit and linearized plasmids as template. The plasmids used as template contained the T7 RNA polymerase promoter followed by a polycistronic DNA sequence encoding the different CAR variants.

The electroporation of the polycistronic mRNAs into the human T cells was done using the CytoLVT-S device (Cellectis), according to the following protocol: $5 \times 10^6$ T cells preactivated several days (3-5) with anti CD3/CD28 coated beads and IL2 were resuspended in cytoporation buffer T, and electroporated with 45 µg of mRNA. Twenty-four hours after electroporation, human T cells engineered using polycistronic mRNAs encoding the multi-chain CARs were labeled with a fixable viability dye eFluor-780 and a PE-conjugated goat anti mouse IgG F(ab')2 fragment specific, and analysed by flow cytometry.

The live T cells engineered using polycistronic mRNAs expressed the multi-chain CARs on their surface.

C. Lenviral Expression in T Cells

In Vitro Screening of ROR1-Specific mcCAR

Figure 5:
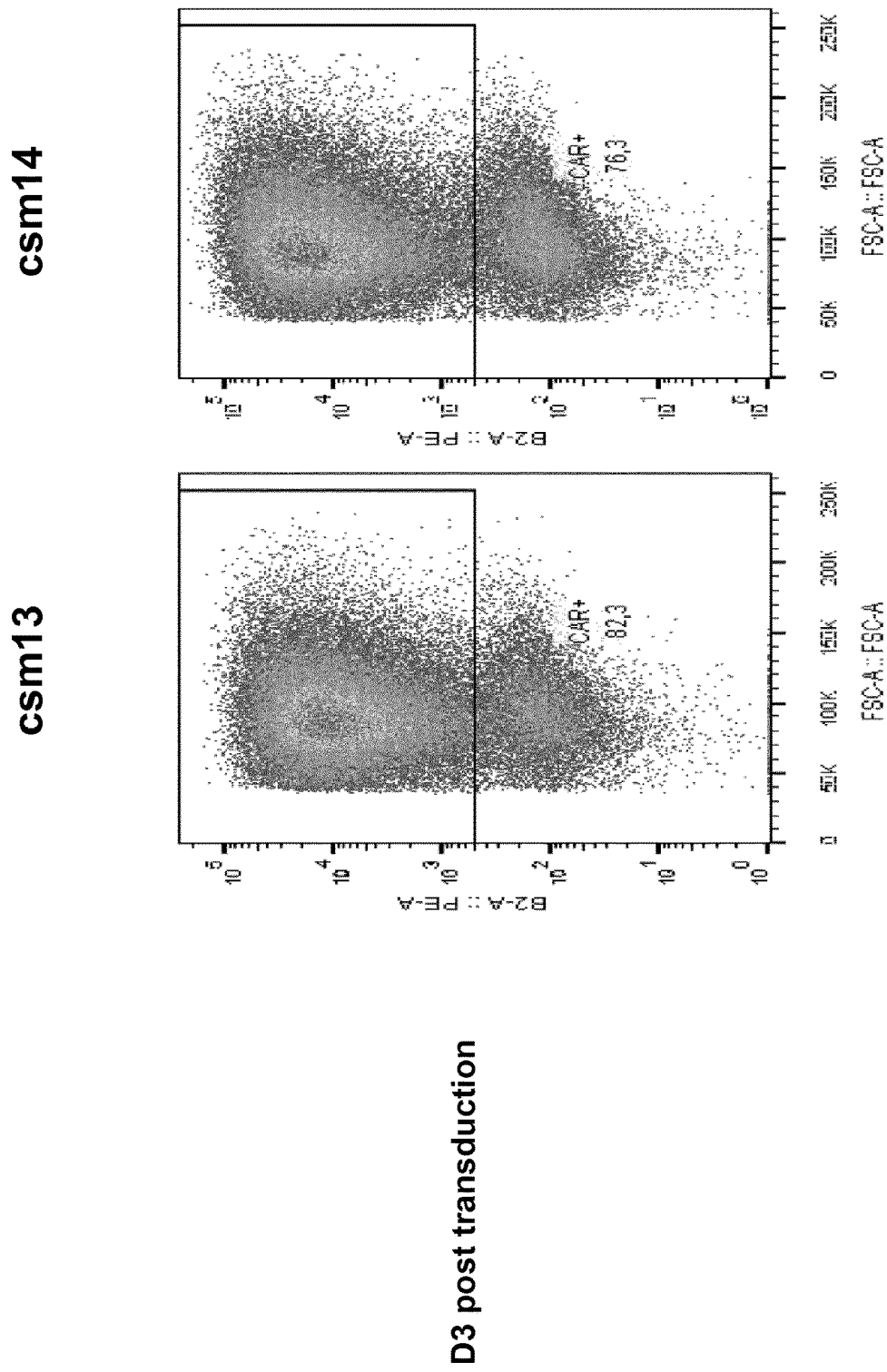
FIG. 5: FACS analysis showing cell surface expression of the multi-chain CARs mc13 and mc14 in transduced T cells. Data are presented as mean+/−SD of 3 independent experiments.
Figure 5:
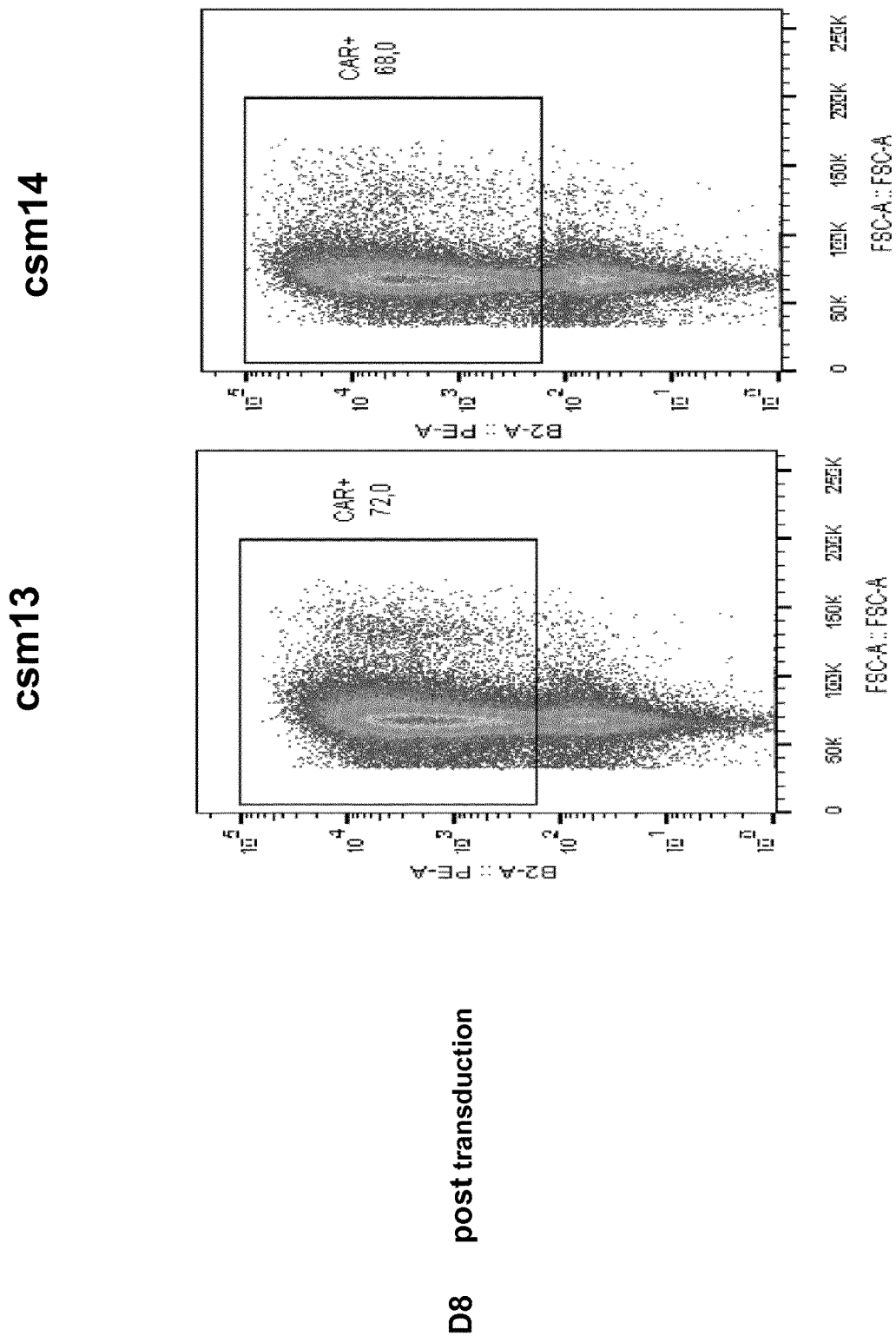
Figure 5:
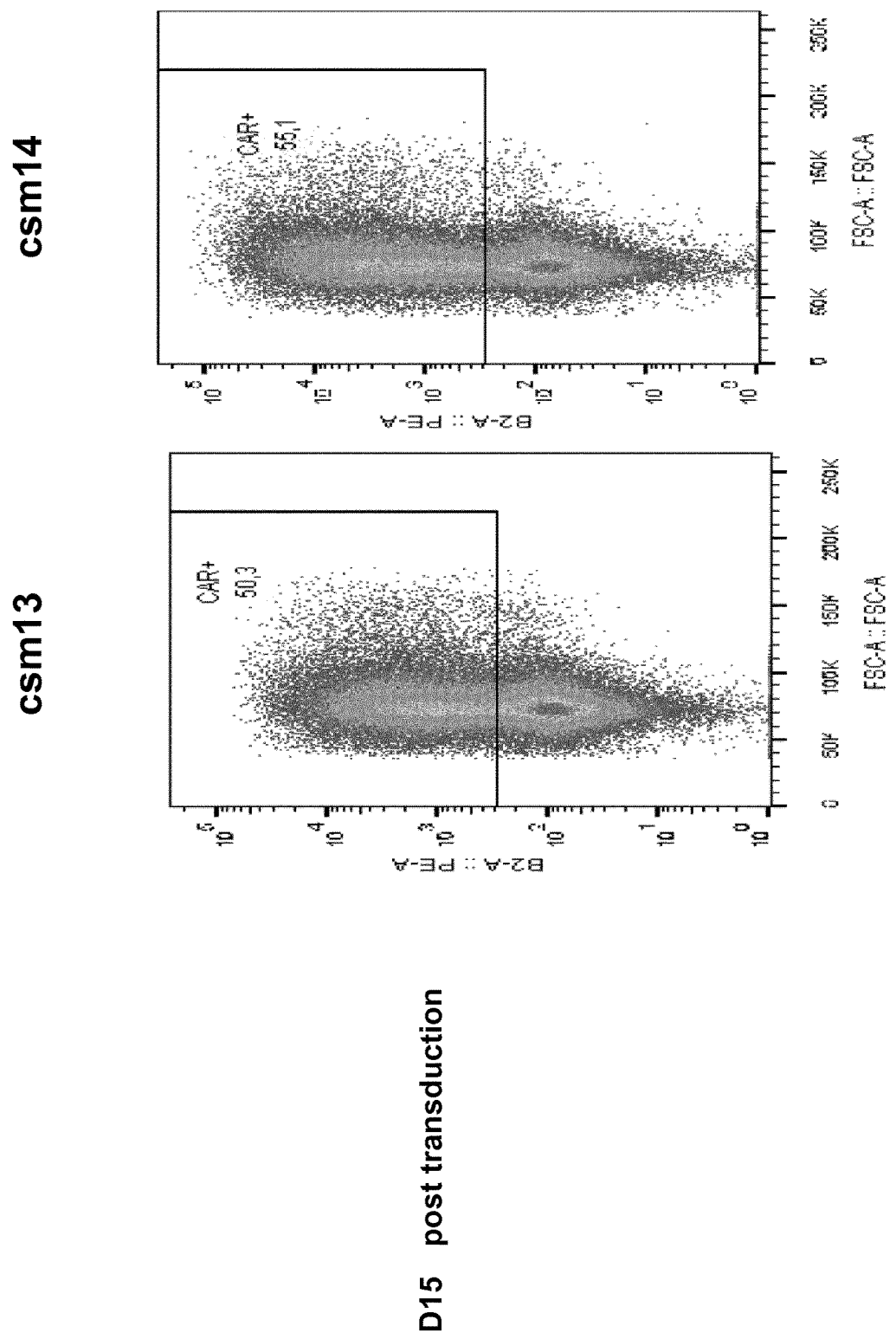
Figure 6:
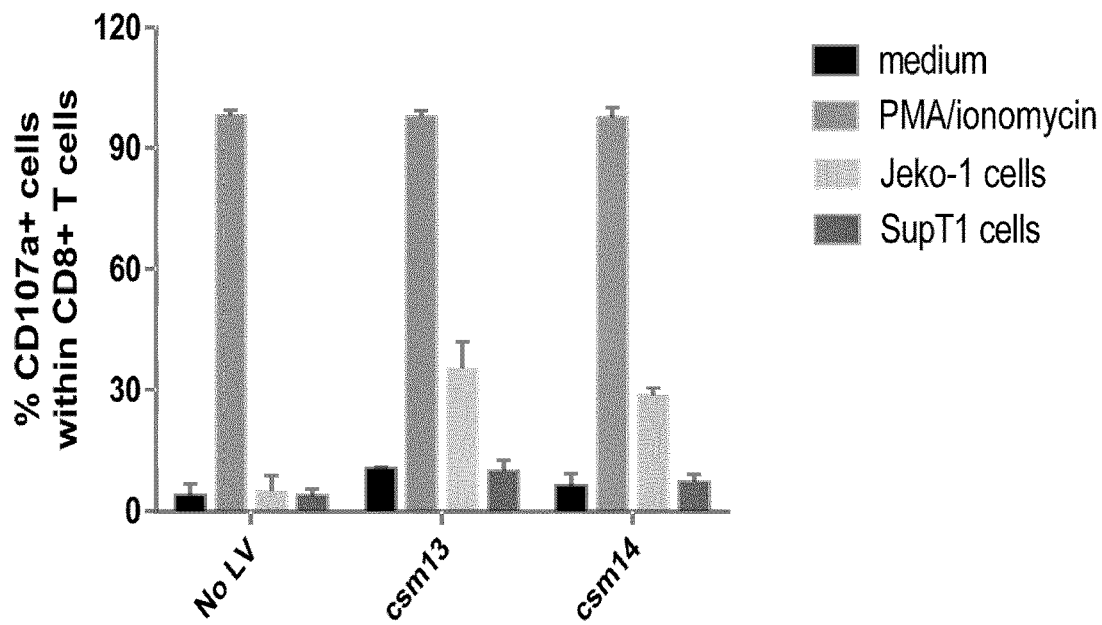
FIG. 6: Degranulation assay performed on multi-chain CARs mc13 and mc14 in the presence of ROR1-positive cell line (Jeko-1), or ROR1-negative cell line (SupT1) or in absence of cell line (medium), or in PMA/ionomycin (positive control for T cell activation). A control was done for untransduced T cells (No LV). Data are presented as mean+/−SD of 3 independent experiments.)
Figure 7:
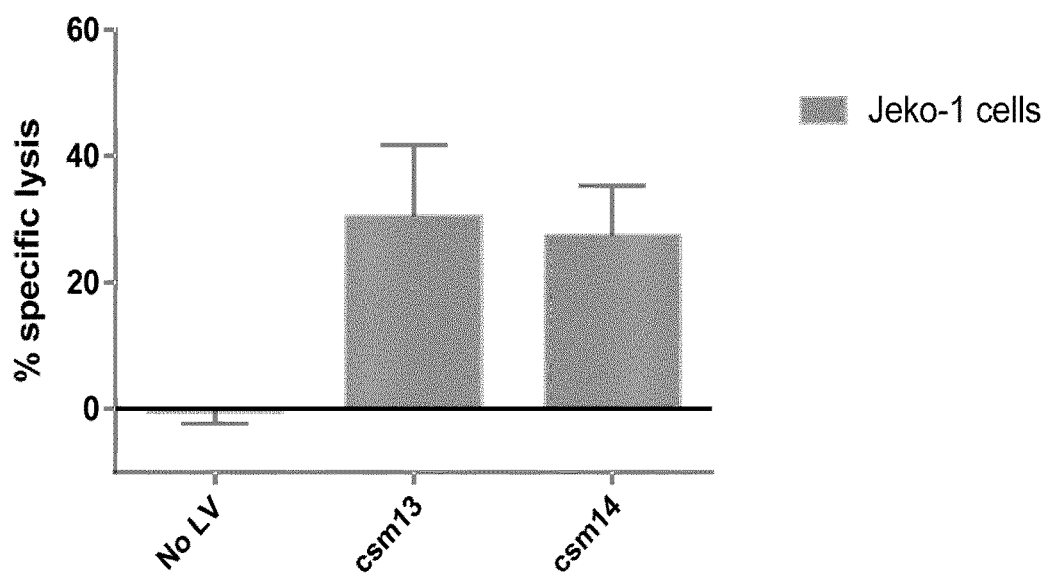
FIG. 7: Cytotoxicity assay performed for multi-chain CARs mc13 and mc14 in the presence of ROR1-positive cell line (Jeko-1). A control was done for untransduced T cells (No LV). Data are presented as mean+/−SD of 3 independent experiments.
Figure 8:
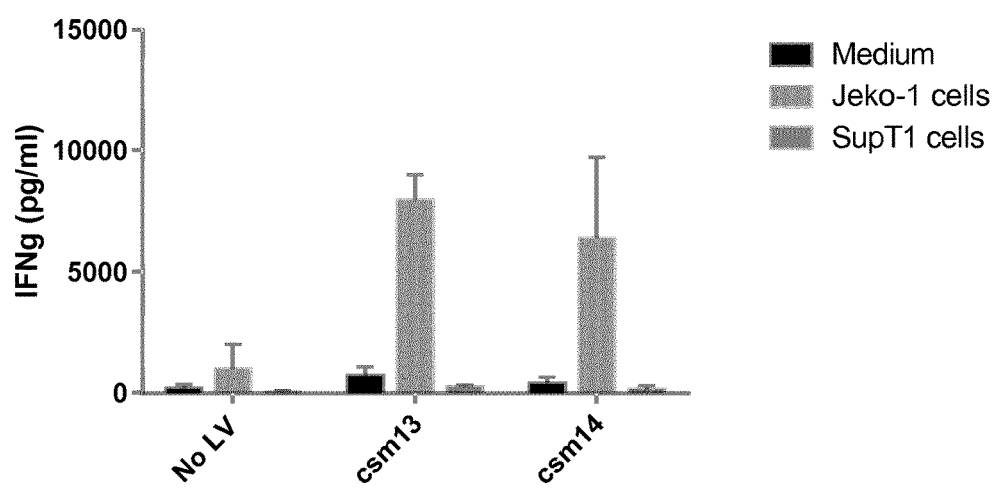
FIG. 8: INFγ secretion assay for multi-chain CARs mc13 and mc14 in the presence of ROR1-positive cell line (Jeko-1). A control was done for untransduced T cells (No LV). Data are presented as mean+/−SD of 3 independent experiments.

The polycistronic genes encoding csm13 and csm14 were vectorized in human T cells using lentiviral vectors as reported previously. Firstly the cell surface expression profile was assessed over time of csm13 and csm14 in transduced T cells. For that purpose, the ROR1/Fc fusion protein was used. As shown in FIG. 5, it was observed that csm13 and csm14 were highly expressed on the cell surface 3 days post transduction and remained relatively highly expressed over a 2 weeks period. The capacity of csm13 and csm14 was then assessed to mediate antigen-dependent T cells activation. To address this issue, activity assays was performed using a ROR1-positive cell line (Jeko-1), and a ROR1-negative cell line (SupT1). It was observed that csm13 and csm14 were able to activate T cells in the presence of Jeko-1 but not in the presence of SupT1 as shown with the results of the degranulation assay, the cytotoxicity assay and the IFNγ secretion assay shown in FIGS. 6, 7 and 8 respectively.

D. The Human T Cells Transiently Expressing the Multi-Chain CARs Degranulate Following Coculture with Target Cells Twenty-four hours after electroporation, human T cells engineered using polycistronic mRNAs encoding the multi-chain CARs were co-cultured with target (Daudi) or control (K562) cells for 6 hours. The CD8+ T cells were then analyzed by flow cytometry to detect the expression of the degranulation marker CD107a at their surface. This experiment aims to check that the human CD8+ T cells expressing the ROR1 multi-chain CARs degranulate in coculture with ROR1 expressing target cells but not in coculture with control cells.

E. The Human T Cells Transiently Expressing the Multi-chain CARs Secrete Cytokines Following Coculture with Target Cells Twenty-four hours after electroporation, human T cells engineered using polycistronic mRNAs encoding the multi-chain CARs were co-cultured with target (Daudi) or control (K562) cells for 24 hours. The supernatants were then harvested and analysed using the TH1/TH2 cytokine cytometric bead array kit to quantify the cytokines produced by the T cells. The assay aims to show that the human T cells expressing the multi-chain CARs produce IFNγ, IL8 and IL5 in coculture with ROR1 expressing target cells but not in coculture with control cells.

F. The Human T Cells Transiently Expressing the Multi-Chain CARs Lyse Target Cells Twenty-four hours after electroporation, human T cells engineered using polycistronic mRNAs encoding the multi-chain CARs were co-cultured with target (Daudi) or control (K562) cells for 4 hours. The target cells were then analysed by flow cytometry to analyse their viability. This assay aims to show that the different cells expressing the ROR1 multi-chain CARs lyse the ROR1 expressing target cells but not the control cells.

The invention claimed is:

1. A ROR1 specific multi-chain Chimeric Antigen Receptor (mcCAR) comprising:
   (a) a transmembrane polypeptide from the alpha chain of high-affinity IgE receptor (FcεRI) fused to an extracellular ROR1 ligand binding domain;
   (b) a second transmembrane polypeptide from the gamma chain of FcεRI fused to a signal transducing domain of CD3zeta; and
   (c) a third transmembrane polypeptide from the beta chain of FcεRI comprising a costimulatory domain of 4-1BB,
   wherein said ROR1 ligand binding domain fused to said alpha chain of FcεRI is a single-chain variable fragment (scFv) comprising variable heavy ($V_H$) and variable light ($V_L$) chains conferring specificity to ROR1, wherein:
   (i) said $V_H$ chain comprises a polypeptide sequence displaying at least 90% identity to SEQ ID NO: 28, and said $V_L$ chain comprises a polypeptide displaying at least 90% sequence identity to SEQ ID NO:32, wherein said $V_H$ chain comprises SEQ ID NO:29, SEQ ID NO:30, and SEQ ID NO:31, and wherein said $V_L$ chain comprises SEQ ID NO:33, SEQ ID NO:34, and SEQ ID NO:35;
   (ii) said $V_H$ chain comprises a polypeptide sequence displaying at least 90% identity to SEQ ID NO: 12, and said $V_L$ chain comprises a polypeptide displaying at least 90% sequence identity to SEQ ID NO:16, wherein said $V_H$ chain comprises SEQ ID NO:13, SEQ ID NO:14, and SEQ ID NO:15, and wherein said $V_L$ chain comprises SEQ ID NO:17, SEQ ID NO:18, and SEQ ID NO:19;
   (iii) said $V_H$ chain comprises a polypeptide sequence displaying at least 90% identity to SEQ ID NO: 20, and said $V_L$ chain comprises a polypeptide displaying at least 90% sequence identity to SEQ ID NO:24, wherein said $V_H$ chain comprises SEQ ID NO:21, SEQ ID NO:22, and SEQ ID NO:23, and wherein said $V_L$ chain comprises SEQ ID NO:25, SEQ ID NO:26, and SEQ ID NO:27;
   (iv) said $V_H$ chain comprises a polypeptide sequence displaying at least 90% identity to SEQ ID NO: 36, and said V_L chain comprises a polypeptide displaying at least 90% sequence identity to SEQ ID NO:40, wherein said V_H chain comprises SEQ ID NO:37, SEQ ID NO:38, and SEQ ID NO:39, and wherein said V_L chain comprises SEQ ID NO:41, SEQ ID NO:42, and SEQ ID NO:43;

(v) said V_H chain comprises a polypeptide sequence displaying at least 90% identity to SEQ ID NO:44, and said V_L chain comprises a polypeptide displaying at least 90% sequence identity to SEQ ID NO:48, wherein said V_H chain comprises SEQ ID NO:45, SEQ ID NO:46, and SEQ ID NO:47, and wherein said V_L chain comprises SEQ ID NO:49, SEQ ID NO:50, and SEQ ID NO:51;

(vi) said V_H chain comprises a polypeptide sequence displaying at least 90% identity to SEQ ID NO: 52, and said V_L chain comprises a polypeptide displaying at least 90% sequence identity to SEQ ID NO:56, wherein said V_H chain comprises SEQ ID NO:53, SEQ ID NO:54, and SEQ ID NO:55, and wherein said V_L chain comprises SEQ ID NO:57, SEQ ID NO:58, and SEQ ID NO:59;

(vii) said V_H chain comprises a polypeptide sequence displaying at least 90% identity to SEQ ID NO: 60, and said V_L chain comprises a polypeptide displaying at least 90% sequence identity to SEQ ID NO:64, wherein said V_H chain comprises SEQ ID NO:61, SEQ ID NO:62, and SEQ ID NO:63, and wherein said V_L chain comprises SEQ ID NO:65, SEQ ID NO:66, and SEQ ID NO:67; or (viii) said V_H chain comprises a polypeptide sequence displaying at least 90% identity to SEQ ID NO:68, and said V_L chain comprises a polypeptide displaying at least 90% sequence identity to SEQ ID NO:72, wherein said V_H chain comprises SEQ ID NO:69, SEQ ID NO:70, and SEQ ID NO:71, and wherein said V_L chain comprises SEQ ID NO:73, SEQ ID NO:74, and SEQ ID NO:75.

2. The ROR1 specific mcCAR of claim 1, wherein said V_H chain comprises a polypeptide sequence displaying at least 90% identity to SEQ ID NO:28, and said V_L chain comprises a polypeptide displaying at least 90% sequence identity to SEQ ID NO:32, wherein said V_H chain comprises SEQ ID NO:29, SEQ ID NO:30, and SEQ ID NO:31, and wherein said V_L chain comprises SEQ ID NO:33, SEQ ID NO:34, and SEQ ID NO:35.

3. The ROR1 specific mcCAR of claim 1, wherein said V_H chain comprises a polypeptide sequence displaying at least 90% identity to SEQ ID NO:12, and said V_L chain comprises a polypeptide displaying at least 90% sequence identity to SEQ ID NO:16, wherein said V_H chain comprises SEQ ID NO:13, SEQ ID NO:14, and SEQ ID NO:15, and wherein said V_L chain comprises SEQ ID NO:17, SEQ ID NO:18, and SEQ ID NO:19.

4. The ROR1 specific mcCAR of claim 1, wherein said alpha chain of FcεRI is fused to said extracellular ligand-binding domain by a hinge from CD8a, IgG1 or FcγRIIIa proteins.

5. The ROR1 specific mcCAR of claim 4, wherein said hinge comprises a polypeptide sequence displaying at least 90% identity to SEQ ID NO: 2.

6. The ROR1 specific mcCAR according to claim 1, wherein said signal transducing domain comprises a polypeptide sequence displaying at least 90% identity to SEQ ID NO:79.

7. The ROR1 specific mcCAR according to claim 1, wherein said co-stimulatory domain comprises a polypeptide sequence displaying at least 90% identity to SEQ ID NO: 6.

8. The ROR1 specific mcCAR of claim 1, wherein said ROR1 specific mcCAR comprises a polypeptide sequence displaying at least 80% identity to any one of SEQ ID NOs:76-83.

9. The ROR1 specific mcCAR of claim 8, wherein said ROR1 specific mcCAR comprises a polypeptide sequence displaying at least 80% identity to SEQ ID NO: 78 or SEQ ID NO: 76.

10. A polynucleotide comprising a nucleic acid sequence encoding a ROR1 specific mcCAR of claim 1.

11. A method of engineering an immune cell, wherein said method comprises introducing a polynucleotide of claim 10 into an immune cell, wherein said an immune cell expresses said ROR1 specific mcCAR.

12. An isolated immune cell comprising at least one ROR1 specific mcCAR of claim 1.

13. The isolated immune cell according to claim 12 formulated as a medicament.

14. A method of treating a disease or condition in a human subject comprising administering to said subject a therapeutically effective amount of an isolated immune cell according to claim 12.

15. The method of claim 14, wherein the disease or condition is a pre-malignant or malignant cancer comprising ROR1-expressing cells.

16. The method of claim 15, wherein the pre-malignant or malignant cancer is chronic lymphocytic leukemia (CLL), Small Lymphocytic Lymphoma (SLL), acute myelogenous leukemia, chronic myelogenous leukemia, myelodysplastic syndrome, Mantle Cell Lymphoma (MCL), or an Acute Lymphoblastic Leukemia (ALL) with a t(1;19) chromosome translocation.

17. The immune isolated cell of claim 12, wherein the immune cell is a NK cell, inflammatory T-lymphocyte, cytotoxic T-lymphocyte, regulatory T-lymphocyteor helper T-lymphocyte.

18. A method for treating a disease or condition in a patient in need thereof comprising administering to said patient the immune cell of claim 12.

19. The method of claim 18, wherein said immune cells are recovered from a donor.

20. The method of claim 18, wherein said immune cells are recovered from a patient.

* * * * *

UNITED STATES PATENT AND TRADEMARK OFFICE
CERTIFICATE OF CORRECTION

PATENT NO. : 10,544,201 B2
APPLICATION NO. : 15/329530
DATED : January 28, 2020
INVENTOR(S) : Cecile Schiffer-Mannioui Page 1 of 1

It is certified that error appears in the above-identified patent and that said Letters Patent is hereby corrected as shown below:

In the Claims

Column 118, Line 7 (Claim 6), please delete "NO:79." and insert -- NO:9. --, therefor;

Column 118, Line 25 (Claim 11), after "said", please delete "an";

Column 118, Line 47 (Claim 17), please delete "T-lymphocyteor" and insert -- T-lymphocyte, or --, therefor.

Signed and Sealed this
Thirtieth Day of June, 2020

Andrei Iancu
*Director of the United States Patent and Trademark Office*